(12) United States Patent
Shitara et al.

(10) Patent No.: US 7,498,415 B2
(45) Date of Patent: Mar. 3, 2009

(54) RECOMBINANT ANTIBODY AGAINST HUMAN INSULIN-LIKE GROWTH FACTOR

(75) Inventors: Kenya Shitara, Fujisawa (JP); Kazuyasu Nakamura, Tokyo (JP); Yuji Ohki, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/573,378

(22) PCT Filed: Sep. 24, 2004

(86) PCT No.: PCT/JP2004/014453

§ 371 (c)(1),
(2), (4) Date: Mar. 24, 2006

(87) PCT Pub. No.: WO2005/028515

PCT Pub. Date: Mar. 31, 2005

(65) Prior Publication Data

US 2006/0240015 A1    Oct. 26, 2006

(30) Foreign Application Priority Data

Sep. 24, 2003    (JP)    ............... 2003-331509

(51) Int. Cl.
*C07K 16/00* (2006.01)
*C07K 16/28* (2006.01)

(52) U.S. Cl. ................. 530/387.1; 530/300; 530/387.3; 530/387.9; 530/388.22

(58) Field of Classification Search ........................ None
See application file for complete search history.

(56) References Cited

U.S. PATENT DOCUMENTS

2006/0165695 A1    7/2006    Shitara et al.
2006/0263362 A1    11/2006   Ochiai et al.

FOREIGN PATENT DOCUMENTS

| EP | 0 292 656 | 11/1988 |
| EP | 0 492 552 | 7/1992 |
| EP | 1 505 075 | 2/2005 |
| EP | 1 661 582 | 5/2006 |
| WO | 94/04569 | 3/1994 |
| WO | WO 02/053596 A2 * | 7/2002 |

OTHER PUBLICATIONS

Russell, et al., "Inhibition of the mitogenic effects of plasma by a . . . ", *Proc. Natl. Acad. Sci.*, vol. 81, No. 8 (1984), pp. 2389-2392.
Mohan, "A simple and efficient scheme for the purification of insulin-like Growth Factor II from human bone matrix extract", Growth Factors, vol. 2, No. 4 (1990) 267-71.
Scheven, et al., "Effects of recombinant human insulin-like Growth Factor I and II (IGF-I/-II) and Growth Hormone (GH) on the . . . ", Growth Regulation, vol. 1, No. 4 (1991) 160-67.
Manes, et al., "Functional Epitope Mapping of insulin-like Growth Factor I (IGF-I) by Anti-IGF-I monoclonal antibodies", Endocrinology, vol. 138, No. 3 (1997) 905-15.
Manes, et al., "Physical mapping of human insulin-like growth factor-I using specific monoclonal antibodies", Journal of Endocrinology, vol. 154, No. 2 (1997) 293-302.
Tanaka, et al., "Identification of a family of insulin-like growth factor II secreted by cultured rat . . . ", Endocrinology, vol. 124, No. 2 (1989) 870-77.
Enjoh, et al., "Characterization of new monoclonal antibodies to human insulin-like growth factor-II and their application in Western immunoblot analysis", Journal of Clinical Endocrinology and Metabolism, vol. 77, No. 2 (1993) 510-17.

* cited by examiner

*Primary Examiner*—Robert Landsman
*Assistant Examiner*—Ian Dang
(74) *Attorney, Agent, or Firm*—Fitzpatrick, Cella, Harper & Scinto

(57) ABSTRACT

It is demanded that pharmaceutical agents for therapeutic treatment of diseases such as cancer, acromegaly and diabetic complications, of which IGF is involved in the progress of the conditions.

The present invention provides a recombinant antibody or an antibody fragment thereof which specifically binds to human insulin-like growth factor-I (hereinafter referred to as hIGF-I) and human insulin-like growth factor-II (hereinafter referred to as hIGF-II) to inhibit the biological activities of human IGF-I and human IGF-II, a transformant producing the antibody or the antibody fragment thereof, a process for producing the antibody or the antibody fragment thereof, and a medicament comprising the antibody or the antibody fragment thereof as the active ingredient therein.

11 Claims, 19 Drawing Sheets

```
                             SEQUENCE LISTING

<160> NUMBER OF SEQ ID NOS: 71

<210> SEQ ID NO 1
<211> LENGTH: 411
<212> TYPE: DNA
<213> ORGANISM: Rattus norvegics
<220> FEATURE:
<221> NAME/KEY: CDS
<222> LOCATION: (1)..(411)

<400> SEQUENCE: 1 atg gac atc agg ctc agc ttg gtt ttc ctt gtc ctt ttc ata aaa ggt      48
Met Asp Ile Arg Leu Ser Leu Val Phe Leu Val Leu Phe Ile Lys Gly
 1               5                  10                  15 gtc cag tgt gag gta cac ctg gtg gaa tct ggg gga ggc tta gtg cag      96
Val Gln Cys Glu Val His Leu Val Glu Ser Gly Gly Gly Leu Val Gln
             20                  25                  30 cct gga agg tcc ctg aaa ctc tcc tgt gca gcc tca gga ttc act ttc     144
Pro Gly Arg Ser Leu Lys Leu Ser Cys Ala Ala Ser Gly Phe Thr Phe
         35                  40                  45 agt aac tat tac atg acc tgg gtc cgc cag gct cca acg aag ggt ctg     192
Ser Asn Tyr Tyr Met Thr Trp Val Arg Gln Ala Pro Thr Lys Gly Leu
     50                  55                  60 gag tgg gtc gca tac att agt agt ggt ggt ggt agc act tac tat cga     240
Glu Trp Val Ala Tyr Ile Ser Ser Gly Gly Gly Ser Thr Tyr Tyr Arg
 65                  70                  75                  80 gac tcc gtg aag ggc cga ttc act atc tcc aga gat aat gca aaa agc     288
Asp Ser Val Lys Gly Arg Phe Thr Ile Ser Arg Asp Asn Ala Lys Ser
                 85                  90                  95 acc ctg tac ctg caa atg gac agt ctg agg tct gag gac acg gcc act     336
Thr Leu Tyr Leu Gln Met Asp Ser Leu Arg Ser Glu Asp Thr Ala Thr
            100                 105                 110 tat tac tgt aca aca gag gac tat ggg tat tgg ttt gct tac tgg ggc     384
Tyr Tyr Cys Thr Thr Glu Asp Tyr Gly Tyr Trp Phe Ala Tyr Trp Gly
        115                 120                 125 caa ggc act ctg gtc act gtc tct tca                                 411
Gln Gly Thr Leu Val Thr Val Ser Ser
    130                 135

<210> SEQ ID NO 2
<211> LENGTH: 137
<212> TYPE: PRT
<213> ORGANISM: Rattus norvegics

<400> SEQUENCE: 2

Met Asp Ile Arg Leu Ser Leu Val Phe Leu Val Leu Phe Ile Lys Gly
 1               5                  10                  15

Val Gln Cys Glu Val His Leu Val Glu Ser Gly Gly Gly Leu Val Gln
             20                  25                  30

Pro Gly Arg Ser Leu Lys Leu Ser Cys Ala Ala Ser Gly Phe Thr Phe
         35                  40                  45

Ser Asn Tyr Tyr Met Thr Trp Val Arg Gln Ala Pro Thr Lys Gly Leu
     50                  55                  60
```

```
Glu Trp Val Ala Tyr Ile Ser Ser Gly Gly Ser Thr Tyr Tyr Arg
 65                  70                  75                  80

Asp Ser Val Lys Gly Arg Phe Thr Ile Ser Arg Asp Asn Ala Lys Ser
                 85                  90                  95

Thr Leu Tyr Leu Gln Met Asp Ser Leu Arg Ser Glu Asp Thr Ala Thr
            100                 105                 110

Tyr Tyr Cys Thr Thr Glu Asp Tyr Gly Tyr Trp Phe Ala Tyr Trp Gly
        115                 120                 125

Gln Gly Thr Leu Val Thr Val Ser Ser
    130                 135

<210> SEQ ID NO 3
<211> LENGTH: 384
<212> TYPE: DNA
<213> ORGANISM: Rattus norvegics
<220> FEATURE:
<221> NAME/KEY: CDS
<222> LOCATION: (1)..(384)

<400> SEQUENCE: 3 atg gat ttt cag gtg cag agt ttc agc ctc ctg cta atc agt atc aca      48
Met Asp Phe Gln Val Gln Ser Phe Ser Leu Leu Leu Ile Ser Ile Thr
  1               5                  10                  15 gtc ata gtg tcc agt gga gaa att gtg ctc acc cag tct cca aca acc      96
Val Ile Val Ser Ser Gly Glu Ile Val Leu Thr Gln Ser Pro Thr Thr
             20                  25                  30 atg gct gca tct cca gga gag aag gtc acc atc acc tgc cgt gcc agc     144
Met Ala Ala Ser Pro Gly Glu Lys Val Thr Ile Thr Cys Arg Ala Ser
         35                  40                  45 tca agt gta agc tac atg cac tgg ttc cag cag aag tca ggc acc tcc     192
Ser Ser Val Ser Tyr Met His Trp Phe Gln Gln Lys Ser Gly Thr Ser
     50                  55                  60 ccc aaa ccc tgg att tat ggc aca tcc aag ctg gct tct gga gtc cca     240
Pro Lys Pro Trp Ile Tyr Gly Thr Ser Lys Leu Ala Ser Gly Val Pro
 65                  70                  75                  80 gat cgc ttc agt ggc agt ggg tct ggg acc tct tat tct ctc aca atc     288
Asp Arg Phe Ser Gly Ser Gly Ser Gly Thr Ser Tyr Ser Leu Thr Ile
                 85                  90                  95 agc tcc atg gag gct gaa gat gct gct act tat tac tgt ctg cag agg     336
Ser Ser Met Glu Ala Glu Asp Ala Ala Thr Tyr Tyr Cys Leu Gln Arg
            100                 105                 110 agt agt tac cca ccc acg ttt gga gct ggg acc aag ctg gaa ctg aaa     384
Ser Ser Tyr Pro Pro Thr Phe Gly Ala Gly Thr Lys Leu Glu Leu Lys
        115                 120                 125

<210> SEQ ID NO 4
<211> LENGTH: 128
<212> TYPE: PRT
<213> ORGANISM: Rattus norvegics

<400> SEQUENCE: 4

Met Asp Phe Gln Val Gln Ser Phe Ser Leu Leu Leu Ile Ser Ile Thr
  1               5                  10                  15

Val Ile Val Ser Ser Gly Glu Ile Val Leu Thr Gln Ser Pro Thr Thr
             20                  25                  30

Met Ala Ala Ser Pro Gly Glu Lys Val Thr Ile Thr Cys Arg Ala Ser
         35                  40                  45

Ser Ser Val Ser Tyr Met His Trp Phe Gln Gln Lys Ser Gly Thr Ser
     50                  55                  60
```

```
Pro Lys Pro Trp Ile Tyr Gly Thr Ser Lys Leu Ala Ser Gly Val Pro
 65                  70                  75                  80

Asp Arg Phe Ser Gly Ser Gly Ser Gly Thr Ser Tyr Ser Leu Thr Ile
             85                  90                  95

Ser Ser Met Glu Ala Glu Asp Ala Ala Thr Tyr Tyr Cys Leu Gln Arg
        100                 105                 110

Ser Ser Tyr Pro Pro Thr Phe Gly Ala Gly Thr Lys Leu Glu Leu Lys
    115                 120                 125
```

<210> SEQ ID NO 5
<211> LENGTH: 5
<212> TYPE: PRT
<213> ORGANISM: Rattus norvegics

<400> SEQUENCE: 5

```
Asn Tyr Tyr Met Thr
 1               5
```

<210> SEQ ID NO 6
<211> LENGTH: 17
<212> TYPE: PRT
<213> ORGANISM: Rattus norvegics

<400> SEQUENCE: 6

```
Tyr Ile Ser Ser Gly Gly Gly Ser Thr Tyr Tyr Arg Asp Ser Val Lys
 1               5                  10                  15

Gly
```

<210> SEQ ID NO 7
<211> LENGTH: 9
<212> TYPE: PRT
<213> ORGANISM: Rattus norvegics

<400> SEQUENCE: 7

```
Glu Asp Tyr Gly Tyr Trp Phe Ala Tyr
 1               5
```

<210> SEQ ID NO 8
<211> LENGTH: 10
<212> TYPE: PRT
<213> ORGANISM: Rattus norvegics

<400> SEQUENCE: 8

```
Arg Ala Ser Ser Val Ser Tyr Met His
 1               5                  10
```

<210> SEQ ID NO 9
<211> LENGTH: 7
<212> TYPE: PRT
<213> ORGANISM: Rattus norvegics

<400> SEQUENCE: 9

```
Gly Thr Ser Lys Leu Ala Ser
 1               5
```

<210> SEQ ID NO 10
<211> LENGTH: 9
<212> TYPE: PRT
<213> ORGANISM: Rattus norvegics

<400> SEQUENCE: 10

```
Leu Gln Arg Ser Ser Tyr Pro Pro Thr
 1               5
```

```
<210> SEQ ID NO 11
<211> LENGTH: 118
<212> TYPE: PRT
<213> ORGANISM: Artificial Sequence
<220> FEATURE:
<221> NAME/KEY: gene
<222> LOCATION: (1)..(118)
<223> OTHER INFORMATION: Description of Artificial Sequence: synthetic
      protein

<400> SEQUENCE: 11

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
             20                  25                  30

Tyr Met Thr Trp Val Arg Gln Ala Pro Gly Lys Gly Leu Glu Trp Val
         35                  40                  45

Ala Tyr Ile Ser Ser Gly Gly Ser Thr Tyr Tyr Arg Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Tyr Gly Tyr Trp Phe Ala Tyr Trp Gly Gln Gly Thr
            100                 105                 110

Leu Val Thr Val Ser Ser
        115

<210> SEQ ID NO 12
<211> LENGTH: 137
<212> TYPE: PRT
<213> ORGANISM: Artificial Sequence
<220> FEATURE:
<222> LOCATION: (1)..(137)
<223> OTHER INFORMATION: Description of Artificial Sequence: synthetic
      protein

<400> SEQUENCE: 12

Met Asp Ile Arg Leu Ser Leu Val Phe Leu Val Leu Phe Ile Lys Gly
  1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Ser Asn Tyr Tyr Met Thr Trp Val Arg Gln Ala Pro Gly Lys Gly Leu
 50                  55                  60

Glu Trp Val Ala Tyr Ile Ser Ser Gly Gly Ser Thr Tyr Tyr Arg
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Glu Asp Tyr Gly Tyr Trp Phe Ala Tyr Trp Gly
            115                 120                 125

Gln Gly Thr Leu Val Thr Val Ser Ser
        130                 135

<210> SEQ ID NO 13
```

<211> LENGTH: 411
<212> TYPE: DNA
<213> ORGANISM: Artificial Sequence
<220> FEATURE:
<221> NAME/KEY: CDS
<222> LOCATION: (1)..(411)
<223> OTHER INFORMATION: Description of Artificial Sequence: synthetic DNA

<400> SEQUENCE: 13

```
atg gac atc agg ctc agc ttg gtt ttc ctt gtc ctt ttc ata aaa ggt     48
Met Asp Ile Arg Leu Ser Leu Val Phe Leu Val Leu Phe Ile Lys Gly
 1               5                  10                  15 gtc cag tgt cag gtg cag ctg gtg gag tct ggg gga ggc gtc gta cag     96
Val Gln Cys Gln Val Gln Leu Val Glu Ser Gly Gly Gly Val Val Gln
             20                  25                  30 cct ggg agg tcc ctg aga ctc tcc tgt gca gcc tct gga ttc acc ttt    144
Pro Gly Arg Ser Leu Arg Leu Ser Cys Ala Ala Ser Gly Phe Thr Phe
         35                  40                  45 agc aac tat tac atg acc tgg gtc cgc cag gct cca ggg aag ggg ctg    192
Ser Asn Tyr Tyr Met Thr Trp Val Arg Gln Ala Pro Gly Lys Gly Leu
     50                  55                  60 gag tgg gtc gct tac att agt agt ggt ggt ggt agc act tac tat cga    240
Glu Trp Val Ala Tyr Ile Ser Ser Gly Gly Gly Ser Thr Tyr Tyr Arg
 65                  70                  75                  80 gac tcc gtg aag ggc cgg ttc acc atc tcc aga gac aat tcc aag aac    288
Asp Ser Val Lys Gly Arg Phe Thr Ile Ser Arg Asp Asn Ser Lys Asn
                 85                  90                  95 acg ctg tat ctg caa atg aac agc ctg aga gcc gag gac acg gcc gta    336
Thr Leu Tyr Leu Gln Met Asn Ser Leu Arg Ala Glu Asp Thr Ala Val
            100                 105                 110 tat tac tgt gcg aga gag gac tat ggg tat tgg ttt gct tac tgg ggc    384
Tyr Tyr Cys Ala Arg Glu Asp Tyr Gly Tyr Trp Phe Ala Tyr Trp Gly
        115                 120                 125 cag gga acc ctg gtc acc gtc tcc tca                                411
Gln Gly Thr Leu Val Thr Val Ser Ser
    130                 135
```

<210> SEQ ID NO 14
<211> LENGTH: 106
<212> TYPE: PRT
<213> ORGANISM: Artificial Sequence
<220> FEATURE:
<222> LOCATION: (1)..(106)
<223> OTHER INFORMATION: Description of Artificial Sequence: synthetic protein

<400> SEQUENCE: 14

```
Asp Ile Val Met Thr Gln Ser Pro Asp Ser Leu Ala Val Ser Leu Gly
 1               5                  10                  15

Glu Arg Ala Thr Ile Asn Cys Arg Ala Ser Ser Ser Val Ser Tyr Met
             20                  25                  30

His Trp Tyr Gln Gln Lys Pro Gly Gln Pro Pro Lys Leu Leu Ile Tyr
         35                  40                  45

Gly Thr Ser Lys Leu Ala Ser Gly Val Pro Asp Arg Phe Ser Gly Ser
     50                  55                  60

Gly Ser Gly Thr Asp Phe Thr Leu Thr Ile Ser Ser Leu Gln Ala Glu
 65                  70                  75                  80

Asp Val Ala Val Tyr Tyr Cys Leu Gln Arg Ser Ser Tyr Pro Pro Thr
                 85                  90                  95

Phe Gly Gln Gly Thr Lys Val Glu Ile Lys
            100                 105
```

<210> SEQ ID NO 15
<211> LENGTH: 128
<212> TYPE: PRT
<213> ORGANISM: Artificial Sequence
<220> FEATURE:
<222> LOCATION: (1)..(128)
<223> OTHER INFORMATION: Description of Artificial Sequence: synthetic protein

<400> SEQUENCE: 15

Met Asp Phe Gln Val Gln Ser Phe Ser Leu Leu Leu Ile Ser Ile Thr
1               5                   10                  15

Val Ile Val Ser Ser Gly Asp Ile Val Met Thr Gln Ser Pro Asp Ser
            20                  25                  30

Leu Ala Val Ser Leu Gly Glu Arg Ala Thr Ile Asn Cys Arg Ala Ser
        35                  40                  45

Ser Ser Val Ser Tyr Met His Trp Tyr Gln Gln Lys Pro Gly Gln Pro
    50                  55                  60

Pro Lys Leu Leu Ile Tyr Gly Thr Ser Lys Leu Ala Ser Gly Val Pro
65                  70                  75                  80

Asp Arg Phe Ser Gly Ser Gly Ser Gly Thr Asp Phe Thr Leu Thr Ile
                85                  90                  95

Ser Ser Leu Gln Ala Glu Asp Val Ala Val Tyr Tyr Cys Leu Gln Arg
            100                 105                 110

Ser Ser Tyr Pro Pro Thr Phe Gly Gln Gly Thr Lys Val Glu Ile Lys
        115                 120                 125

<210> SEQ ID NO 16
<211> LENGTH: 396
<212> TYPE: DNA
<213> ORGANISM: Artificial Sequence
<220> FEATURE:
<221> NAME/KEY: CDS
<222> LOCATION: (1)..(396)
<223> OTHER INFORMATION: Description of Artificial Sequence: synthetic DNA

<400> SEQUENCE: 16

```
atg gat ttt cag gtg cag agt ttc agc ctc ctg cta atc agt atc aca      48
Met Asp Phe Gln Val Gln Ser Phe Ser Leu Leu Leu Ile Ser Ile Thr
1               5                   10                  15 gtc ata gtg tcc agt gga gac atc gtg atg acc cag tct cca gac tcc      96
Val Ile Val Ser Ser Gly Asp Ile Val Met Thr Gln Ser Pro Asp Ser
            20                  25                  30 ctg gct gtg tct cta ggc gag agg gcc acc atc aac tgc cgt gcc agc     144
Leu Ala Val Ser Leu Gly Glu Arg Ala Thr Ile Asn Cys Arg Ala Ser
        35                  40                  45 tca agt gta agc tac atg cac tgg tac cag cag aaa cca gga cag cct     192
Ser Ser Val Ser Tyr Met His Trp Tyr Gln Gln Lys Pro Gly Gln Pro
    50                  55                  60 cct aag ctg ctc att tac ggc aca tcc aag ctg gct tct ggg gtc cct     240
Pro Lys Leu Leu Ile Tyr Gly Thr Ser Lys Leu Ala Ser Gly Val Pro
65                  70                  75                  80 gac aga ttc agt ggc agc ggg tct ggg aca gat ttc act ctc acc atc     288
Asp Arg Phe Ser Gly Ser Gly Ser Gly Thr Asp Phe Thr Leu Thr Ile
                85                  90                  95 agc agc ctg cag gct gaa gat gtg gca gtt tat tac tgt ctg cag agg     336
Ser Ser Leu Gln Ala Glu Asp Val Ala Val Tyr Tyr Cys Leu Gln Arg
            100                 105                 110 agt agt tac cca cca acg ttc ggc caa ggg acc aag gtg gaa atc aaa     384
```

```
Ser Ser Tyr Pro Pro Thr Phe Gly Gln Gly Thr Lys Val Glu Ile Lys
        115                 120                 125 cgt acg ctc gag                                                      396
Arg Thr Leu Glu
        130

<210> SEQ ID NO 17
<211> LENGTH: 411
<212> TYPE: DNA
<213> ORGANISM: Artificial Sequence
<220> FEATURE:
<221> NAME/KEY: CDS
<222> LOCATION: (1)..(411)
<223> OTHER INFORMATION: Description of Artificial Sequence: synthetic
      DNA

<400> SEQUENCE: 17 atg gac atc agg ctc agc ttg gtt ttc ctt gtc ctt ttc ata aaa ggt       48
Met Asp Ile Arg Leu Ser Leu Val Phe Leu Val Leu Phe Ile Lys Gly
1               5                   10                  15 gtc cag tgt gag gtg cag ctg gtg gag tct ggg gga ggc gtc gta cag       96
Val Gln Cys Glu Val Gln Leu Val Glu Ser Gly Gly Gly Val Val Gln
            20                  25                  30 cct ggg agg tcc ctg aga ctc tcc tgt gca gcc tct gga ttc acc ttt      144
Pro Gly Arg Ser Leu Arg Leu Ser Cys Ala Ala Ser Gly Phe Thr Phe
        35                  40                  45 agc aac tat tac atg acc tgg gtc cgc cag gct cca ggg aag ggg ctg      192
Ser Asn Tyr Tyr Met Thr Trp Val Arg Gln Ala Pro Gly Lys Gly Leu
    50                  55                  60 gag tgg gtc gct tac att agt agt ggt ggt ggt agc act tac tat cga      240
Glu Trp Val Ala Tyr Ile Ser Ser Gly Gly Gly Ser Thr Tyr Tyr Arg
65                  70                  75                  80 gac tcc gtg aag ggc cgg ttc acc atc tcc aga gac aat tcc aag aac      288
Asp Ser Val Lys Gly Arg Phe Thr Ile Ser Arg Asp Asn Ser Lys Asn
                85                  90                  95 acg ctg tat ctg caa atg aac agc ctg aga gcc gag gac acg gcc gta      336
Thr Leu Tyr Leu Gln Met Asn Ser Leu Arg Ala Glu Asp Thr Ala Val
            100                 105                 110 tat tac tgt aca aca gag gac tat ggg tat tgg ttt gct tac tgg ggc      384
Tyr Tyr Cys Thr Thr Glu Asp Tyr Gly Tyr Trp Phe Ala Tyr Trp Gly
        115                 120                 125 cag gga acc ctg gtc acc gtc tcc tca                                  411
Gln Gly Thr Leu Val Thr Val Ser Ser
    130                 135

<210> SEQ ID NO 18
<211> LENGTH: 411
<212> TYPE: DNA
<213> ORGANISM: Artificial Sequence
<220> FEATURE:
<221> NAME/KEY: CDS
<222> LOCATION: (1)..(411)
<223> OTHER INFORMATION: Description of Artificial Sequence: synthetic
      DNA

<400> SEQUENCE: 18 atg gac atc agg ctc agc ttg gtt ttc ctt gtc ctt ttc ata aaa ggt       48
Met Asp Ile Arg Leu Ser Leu Val Phe Leu Val Leu Phe Ile Lys Gly
1               5                   10                  15 gtc cag tgt gag gtg cag ctg gtg gag tct ggg gga ggc gtc gta cag       96
Val Gln Cys Glu Val Gln Leu Val Glu Ser Gly Gly Gly Val Val Gln
            20                  25                  30 cct ggg agg tcc ctg aga ctc tcc tgt gca gcc tct gga ttc acc ttt      144
Pro Gly Arg Ser Leu Arg Leu Ser Cys Ala Ala Ser Gly Phe Thr Phe
```

```
                    35                  40                  45
agc aac tat tac atg acc tgg gtc cgc cag gct cca acg aag ggg ctg      192
Ser Asn Tyr Tyr Met Thr Trp Val Arg Gln Ala Pro Thr Lys Gly Leu
     50                  55                  60 gag tgg gtc gct tac att agt agt ggt ggt ggt agc act tac tat cga      240
Glu Trp Val Ala Tyr Ile Ser Ser Gly Gly Gly Ser Thr Tyr Tyr Arg
 65                  70                  75                  80 gac tcc gtg aag ggc cgg ttc acc atc tcc aga gac aat tcc aag aac      288
Asp Ser Val Lys Gly Arg Phe Thr Ile Ser Arg Asp Asn Ser Lys Asn
                 85                  90                  95 acg ctg tat ctg caa atg aac agc ctg aga gcc gag gac acg gcc gta      336
Thr Leu Tyr Leu Gln Met Asn Ser Leu Arg Ala Glu Asp Thr Ala Val
            100                 105                 110 tat tac tgt aca aca gag gac tat ggg tat tgg ttt gct tac tgg ggc      384
Tyr Tyr Cys Thr Thr Glu Asp Tyr Gly Tyr Trp Phe Ala Tyr Trp Gly
        115                 120                 125 cag gga acc ctg gtc acc gtc tcc tca                                  411
Gln Gly Thr Leu Val Thr Val Ser Ser
    130                 135

<210> SEQ ID NO 19
<211> LENGTH: 384
<212> TYPE: DNA
<213> ORGANISM: Artificial Sequence
<220> FEATURE:
<221> NAME/KEY: CDS
<222> LOCATION: (1)..(384)
<223> OTHER INFORMATION: Description of Artificial Sequence: synthetic
      DNA

<400> SEQUENCE: 19 atg gat ttt cag gtg cag agt ttc agc ctc ctg cta atc agt atc aca       48
Met Asp Phe Gln Val Gln Ser Phe Ser Leu Leu Leu Ile Ser Ile Thr
  1               5                  10                  15 gtc ata gtg tcc agt gga gac atc gtg ctc acc cag tct cca aca acc       96
Val Ile Val Ser Ser Gly Asp Ile Val Leu Thr Gln Ser Pro Thr Thr
                 20                  25                  30 atg gct gtg tct cca ggc gag agg gcc acc atc acc tgc cgt gcc agc      144
Met Ala Val Ser Pro Gly Glu Arg Ala Thr Ile Thr Cys Arg Ala Ser
            35                  40                  45 tca agt gta agc tac atg cac tgg ttc cag cag aaa cca gga cag tcc      192
Ser Ser Val Ser Tyr Met His Trp Phe Gln Gln Lys Pro Gly Gln Ser
     50                  55                  60 cct aag ccc tgg att tac ggc aca tcc aag ctg gct tct ggg gtc cct      240
Pro Lys Pro Trp Ile Tyr Gly Thr Ser Lys Leu Ala Ser Gly Val Pro
 65                  70                  75                  80 gac aga ttc agt ggc agc ggg tct ggg aca tct tat tct ctc acc atc      288
Asp Arg Phe Ser Gly Ser Gly Ser Gly Thr Ser Tyr Ser Leu Thr Ile
                 85                  90                  95 agc agc ctg cag gct gaa gat gct gca act tat tac tgt ctg cag agg      336
Ser Ser Leu Gln Ala Glu Asp Ala Ala Thr Tyr Tyr Cys Leu Gln Arg
            100                 105                 110 agt agt tac cca cca acg ttc ggc caa ggg acc aag gtg gaa atc aaa      384
Ser Ser Tyr Pro Pro Thr Phe Gly Gln Gly Thr Lys Val Glu Ile Lys
        115                 120                 125

<210> SEQ ID NO 20
<211> LENGTH: 384
<212> TYPE: DNA
<213> ORGANISM: Artificial Sequence
<220> FEATURE:
<221> NAME/KEY: CDS
<222> LOCATION: (1)..(384)
```

<223> OTHER INFORMATION: Description of Artificial Sequence: synthetic
      DNA

<400> SEQUENCE: 20

```
atg gat ttt cag gtg cag agt ttc agc ctc ctg cta atc agt atc aca      48
Met Asp Phe Gln Val Gln Ser Phe Ser Leu Leu Leu Ile Ser Ile Thr
 1               5                  10                  15 gtc ata gtg tcc agt gga gac atc gtg atg acc cag tct cca gac tcc      96
Val Ile Val Ser Ser Gly Asp Ile Val Met Thr Gln Ser Pro Asp Ser
             20                  25                  30 ctg gct gtg tct cta ggc gag agg gcc acc atc aac tgc cgt gcc agc     144
Leu Ala Val Ser Leu Gly Glu Arg Ala Thr Ile Asn Cys Arg Ala Ser
         35                  40                  45 tca agt gta agc tac atg cac tgg tac cag cag aaa cca gga cag tcc     192
Ser Ser Val Ser Tyr Met His Trp Tyr Gln Gln Lys Pro Gly Gln Ser
     50                  55                  60 cct aag ccc tgg att tac ggc aca tcc aag ctg gct tct ggg gtc cct     240
Pro Lys Pro Trp Ile Tyr Gly Thr Ser Lys Leu Ala Ser Gly Val Pro
 65                  70                  75                  80 gac aga ttc agt ggc agc ggg tct ggg aca gat ttc act ctc acc atc     288
Asp Arg Phe Ser Gly Ser Gly Ser Gly Thr Asp Phe Thr Leu Thr Ile
                 85                  90                  95 agc agc ctg cag gct gaa gat gct gca act tat tac tgt ctg cag agg     336
Ser Ser Leu Gln Ala Glu Asp Ala Ala Thr Tyr Tyr Cys Leu Gln Arg
            100                 105                 110 agt agt tac cca cca acg ttc ggc caa ggg acc aag gtg gaa atc aaa     384
Ser Ser Tyr Pro Pro Thr Phe Gly Gln Gly Thr Lys Val Glu Ile Lys
        115                 120                 125
```

<210> SEQ ID NO 21
<211> LENGTH: 384
<212> TYPE: DNA
<213> ORGANISM: Artificial Sequence
<220> FEATURE:
<221> NAME/KEY: CDS
<222> LOCATION: (1)..(384)
<223> OTHER INFORMATION: Description of Artificial Sequence: synthetic
      DNA

<400> SEQUENCE: 21

```
atg gat ttt cag gtg cag agt ttc agc ctc ctg cta atc agt atc aca      48
Met Asp Phe Gln Val Gln Ser Phe Ser Leu Leu Leu Ile Ser Ile Thr
 1               5                  10                  15 gtc ata gtg tcc agt gga gac atc gtg atg acc cag tct cca gac tcc      96
Val Ile Val Ser Ser Gly Asp Ile Val Met Thr Gln Ser Pro Asp Ser
             20                  25                  30 ctg gct gtg tct cta ggc gag agg gcc acc atc acc tgc cgt gcc agc     144
Leu Ala Val Ser Leu Gly Glu Arg Ala Thr Ile Thr Cys Arg Ala Ser
         35                  40                  45 tca agt gta agc tac atg cac tgg tac cag cag aaa cca gga cag tcc     192
Ser Ser Val Ser Tyr Met His Trp Tyr Gln Gln Lys Pro Gly Gln Ser
     50                  55                  60 cct aag ccc tgg att tac ggc aca tcc aag ctg gct tct ggg gtc cct     240
Pro Lys Pro Trp Ile Tyr Gly Thr Ser Lys Leu Ala Ser Gly Val Pro
 65                  70                  75                  80 gac aga ttc agt ggc agc ggg tct ggg aca gat ttc act ctc acc atc     288
Asp Arg Phe Ser Gly Ser Gly Ser Gly Thr Asp Phe Thr Leu Thr Ile
                 85                  90                  95 agc agc ctg cag gct gaa gat gct gca act tat tac tgt ctg cag agg     336
Ser Ser Leu Gln Ala Glu Asp Ala Ala Thr Tyr Tyr Cys Leu Gln Arg
            100                 105                 110 agt agt tac cca cca acg ttc ggc caa ggg acc aag gtg gaa atc aaa     384
```

Ser Ser Tyr Pro Pro Thr Phe Gly Gln Gly Thr Lys Val Glu Ile Lys
            115                 120                 125

<210> SEQ ID NO 22
<211> LENGTH: 384
<212> TYPE: DNA
<213> ORGANISM: Artificial Sequence
<220> FEATURE:
<221> NAME/KEY: CDS
<222> LOCATION: (1)..(384)
<223> OTHER INFORMATION: Description of Artificial Sequence: synthetic
      DNA

<400> SEQUENCE: 22

```
atg gat ttt cag gtg cag agt ttc agc ctc ctg cta atc agt atc aca      48
Met Asp Phe Gln Val Gln Ser Phe Ser Leu Leu Leu Ile Ser Ile Thr
  1               5                  10                  15 gtc ata gtg tcc agt gga gac atc gtg atg acc cag tct cca gac tcc      96
Val Ile Val Ser Ser Gly Asp Ile Val Met Thr Gln Ser Pro Asp Ser
             20                  25                  30 ctg gct gtg tct cta ggc gag agg gcc acc atc acc tgc cgt gcc agc     144
Leu Ala Val Ser Leu Gly Glu Arg Ala Thr Ile Thr Cys Arg Ala Ser
         35                  40                  45 tca agt gta agc tac atg cac tgg ttc cag cag aaa cca gga cag tcc     192
Ser Ser Val Ser Tyr Met His Trp Phe Gln Gln Lys Pro Gly Gln Ser
     50                  55                  60 cct aag ccc tgg att tac ggc aca tcc aag ctg gct tct ggg gtc cct     240
Pro Lys Pro Trp Ile Tyr Gly Thr Ser Lys Leu Ala Ser Gly Val Pro
 65                  70                  75                  80 gac aga ttc agt ggc agc ggg tct ggg aca gat ttc act ctc acc atc     288
Asp Arg Phe Ser Gly Ser Gly Ser Gly Thr Asp Phe Thr Leu Thr Ile
                 85                  90                  95 agc agc ctg cag gct gaa gat gtg gca gtt tat tac tgt ctg cag agg     336
Ser Ser Leu Gln Ala Glu Asp Val Ala Val Tyr Tyr Cys Leu Gln Arg
            100                 105                 110 agt agt tac cca cca acg ttc ggc caa ggg acc aag gtg gaa atc aaa     384
Ser Ser Tyr Pro Pro Thr Phe Gly Gln Gly Thr Lys Val Glu Ile Lys
        115                 120                 125
```

<210> SEQ ID NO 23
<211> LENGTH: 384
<212> TYPE: DNA
<213> ORGANISM: Artificial Sequence
<220> FEATURE:
<221> NAME/KEY: CDS
<222> LOCATION: (1)..(384)
<223> OTHER INFORMATION: Description of Artificial Sequence: synthetic
      DNA

<400> SEQUENCE: 23

```
atg gat ttt cag gtg cag agt ttc agc ctc ctg cta atc agt atc aca      48
Met Asp Phe Gln Val Gln Ser Phe Ser Leu Leu Leu Ile Ser Ile Thr
  1               5                  10                  15 gtc ata gtg tcc agt gga gac atc gtg atg acc cag tct cca gac tcc      96
Val Ile Val Ser Ser Gly Asp Ile Val Met Thr Gln Ser Pro Asp Ser
             20                  25                  30 ctg gct gtg tct cta ggc gag agg gcc acc atc acc tgc cgt gcc agc     144
Leu Ala Val Ser Leu Gly Glu Arg Ala Thr Ile Thr Cys Arg Ala Ser
         35                  40                  45 tca agt gta agc tac atg cac tgg ttc cag cag aaa cca gga cag tcc     192
Ser Ser Val Ser Tyr Met His Trp Phe Gln Gln Lys Pro Gly Gln Ser
     50                  55                  60 cct aag ccc tgg att tac ggc aca tcc aag ctg gct tct ggg gtc cct     240
Pro Lys Pro Trp Ile Tyr Gly Thr Ser Lys Leu Ala Ser Gly Val Pro
 65                  70                  75                  80
```

```
                   65                  70                  75                  80
gac aga ttc agt ggc agc ggg tct ggg aca tct tat tct ctc acc atc          288
Asp Arg Phe Ser Gly Ser Gly Ser Gly Thr Ser Tyr Ser Leu Thr Ile
                85                  90                  95 agc agc ctg cag gct gaa gat gct gca act tat tac tgt ctg cag agg          336
Ser Ser Leu Gln Ala Glu Asp Ala Ala Thr Tyr Tyr Cys Leu Gln Arg
            100                 105                 110 agt agt tac cca cca acg ttc ggc caa ggg acc aag gtg gaa atc aaa          384
Ser Ser Tyr Pro Pro Thr Phe Gly Gln Gly Thr Lys Val Glu Ile Lys
        115                 120                 125

<210> SEQ ID NO 24
<211> LENGTH: 384
<212> TYPE: DNA
<213> ORGANISM: Artificial Sequence
<220> FEATURE:
<221> NAME/KEY: CDS
<222> LOCATION: (1)..(384)
<223> OTHER INFORMATION: Description of Artificial Sequence: synthetic
      DNA

<400> SEQUENCE: 24 atg gat ttt cag gtg cag agt ttc agc ctc ctg cta atc agt atc aca           48
Met Asp Phe Gln Val Gln Ser Phe Ser Leu Leu Leu Ile Ser Ile Thr
  1               5                  10                  15 gtc ata gtg tcc agt gga gac atc gtg atg acc cag tct cca gac tcc           96
Val Ile Val Ser Ser Gly Asp Ile Val Met Thr Gln Ser Pro Asp Ser
             20                  25                  30 ctg gct gtg tct cta ggc gag agg gcc acc atc aac tgc cgt gcc agc          144
Leu Ala Val Ser Leu Gly Glu Arg Ala Thr Ile Asn Cys Arg Ala Ser
         35                  40                  45 tca agt gta agc tac atg cac tgg tac cag cag aaa cca gga cag tcc          192
Ser Ser Val Ser Tyr Met His Trp Tyr Gln Gln Lys Pro Gly Gln Ser
     50                  55                  60 cct aag ccc ctc att tac ggc aca tcc aag ctg gct tct ggg gtc cct          240
Pro Lys Pro Leu Ile Tyr Gly Thr Ser Lys Leu Ala Ser Gly Val Pro
 65                  70                  75                  80 gac aga ttc agt ggc agc ggg tct ggg aca tct tat tct ctc acc atc          288
Asp Arg Phe Ser Gly Ser Gly Ser Gly Thr Ser Tyr Ser Leu Thr Ile
                85                  90                  95 agc agc ctg cag gct gaa gat gtg gca gtt tat tac tgt ctg cag agg          336
Ser Ser Leu Gln Ala Glu Asp Val Ala Val Tyr Tyr Cys Leu Gln Arg
            100                 105                 110 agt agt tac cca cca acg ttc ggc caa ggg acc aag gtg gaa atc aaa          384
Ser Ser Tyr Pro Pro Thr Phe Gly Gln Gly Thr Lys Val Glu Ile Lys
        115                 120                 125

<210> SEQ ID NO 25
<211> LENGTH: 384
<212> TYPE: DNA
<213> ORGANISM: Artificial Sequence
<220> FEATURE:
<221> NAME/KEY: CDS
<222> LOCATION: (1)..(384)
<223> OTHER INFORMATION: Description of Artificial Sequence: synthetic
      DNA

<400> SEQUENCE: 25 atg gat ttt cag gtg cag agt ttc agc ctc ctg cta atc agt atc aca           48
Met Asp Phe Gln Val Gln Ser Phe Ser Leu Leu Leu Ile Ser Ile Thr
  1               5                  10                  15 gtc ata gtg tcc agt gga gac atc gtg atg acc cag tct cca gac tcc           96
Val Ile Val Ser Ser Gly Asp Ile Val Met Thr Gln Ser Pro Asp Ser
             20                  25                  30
```

```
ctg gct gtg tct cta ggc gag agg gcc acc atc aac tgc cgt gcc agc    144
Leu Ala Val Ser Leu Gly Glu Arg Ala Thr Ile Asn Cys Arg Ala Ser
        35                  40                  45 tca agt gta agc tac atg cac tgg tac cag cag aaa cca gga cag tcc    192
Ser Ser Val Ser Tyr Met His Trp Tyr Gln Gln Lys Pro Gly Gln Ser
 50                  55                  60 cct aag ccc tgg att tac ggc aca tcc aag ctg gct tct ggg gtc cct    240
Pro Lys Pro Trp Ile Tyr Gly Thr Ser Lys Leu Ala Ser Gly Val Pro
 65                  70                  75                  80 gac aga ttc agt ggc agc ggg tct ggg aca tct tat tct ctc acc atc    288
Asp Arg Phe Ser Gly Ser Gly Ser Gly Thr Ser Tyr Ser Leu Thr Ile
                 85                  90                  95 agc agc ctg cag gct gaa gat gtg gca gtt tat tac tgt ctg cag agg    336
Ser Ser Leu Gln Ala Glu Asp Val Ala Val Tyr Tyr Cys Leu Gln Arg
            100                 105                 110 agt agt tac cca cca acg ttc ggc caa ggg acc aag gtg gaa atc aaa    384
Ser Ser Tyr Pro Pro Thr Phe Gly Gln Gly Thr Lys Val Glu Ile Lys <210> SEQ ID NO 26
<211> LENGTH: 118
<212> TYPE: PRT
<213> ORGANISM: Artificial Sequence
<220> FEATURE:
<221> NAME/KEY: gene
<222> LOCATION: (1)..(118)
<223> OTHER INFORMATION: Description of Artificial Sequence: synthetic
      protein

<400> SEQUENCE: 26

Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
             20                  25                  30

Tyr Met Thr Trp Val Arg Gln Ala Pro Thr Lys Gly Leu Glu Trp Val
         35                  40                  45

Ala Tyr Ile Ser Ser Gly Gly Gly Ser Thr Tyr Tyr Arg Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Thr Glu Asp Tyr Gly Tyr Trp Phe Ala Tyr Trp Gly Gln Gly Thr
            100                 105                 110

Leu Val Thr Val Ser Ser
        115

<210> SEQ ID NO 27
<211> LENGTH: 106
<212> TYPE: PRT
<213> ORGANISM: Artificial Sequence
<220> FEATURE:
<221> NAME/KEY: gene
<222> LOCATION: (1)..(106)
<223> OTHER INFORMATION: Description of Artificial Sequence: synthetic
      protein

<400> SEQUENCE: 27

Asp Ile Val Met Thr Gln Ser Pro Asp Ser Leu Ala Val Ser Leu Gly
  1               5                  10                  15

Glu Arg Ala Thr Ile Thr Cys Arg Ala Ser Ser Ser Val Ser Tyr Met
             20                  25                  30
```

His Trp Phe Gln Gln Lys Pro Gly Gln Ser Pro Lys Pro Trp Ile Tyr
            35                  40                  45

Gly Thr Ser Lys Leu Ala Ser Gly Val Pro Asp Arg Phe Ser Gly Ser
        50                  55                  60

Gly Ser Gly Thr Ser Tyr Ser Leu Thr Ile Ser Ser Leu Gln Ala Glu
 65                  70                  75                  80

Asp Ala Ala Thr Tyr Tyr Cys Leu Gln Arg Ser Ser Tyr Pro Pro Thr
                85                  90                  95

Phe Gly Gln Gly Thr Lys Val Glu Ile Lys
            100                 105

<210> SEQ ID NO 28
<211> LENGTH: 106
<212> TYPE: PRT
<213> ORGANISM: Artificial Sequence
<220> FEATURE:
<221> NAME/KEY: gene
<222> LOCATION: (1)..(106)
<223> OTHER INFORMATION: Description of Artificial Sequence: synthetic
      protein

<400> SEQUENCE: 28

Asp Ile Val Met Thr Gln Ser Pro Asp Ser Leu Ala Val Ser Leu Gly
 1               5                  10                  15

Glu Arg Ala Thr Ile Asn Cys Arg Ala Ser Ser Ser Val Ser Tyr Met
            20                  25                  30

His Trp Tyr Gln Gln Lys Pro Gly Gln Ser Pro Lys Pro Leu Ile Tyr
            35                  40                  45

Gly Thr Ser Lys Leu Ala Ser Gly Val Pro Asp Arg Phe Ser Gly Ser
        50                  55                  60

Gly Ser Gly Thr Ser Tyr Ser Leu Thr Ile Ser Ser Leu Gln Ala Glu
 65                  70                  75                  80

Asp Val Ala Val Tyr Tyr Cys Leu Gln Arg Ser Ser Tyr Pro Pro Thr
                85                  90                  95

Phe Gly Gln Gly Thr Lys Val Glu Ile Lys
            100                 105

<210> SEQ ID NO 29
<211> LENGTH: 106
<212> TYPE: PRT
<213> ORGANISM: Artificial Sequence
<220> FEATURE:
<221> NAME/KEY: gene
<222> LOCATION: (1)..(106)
<223> OTHER INFORMATION: Description of Artificial Sequence: synthetic
      DNA

<400> SEQUENCE: 29

Asp Ile Val Met Thr Gln Ser Pro Asp Ser Leu Ala Val Ser Leu Gly
 1               5                  10                  15

Glu Arg Ala Thr Ile Asn Cys Arg Ala Ser Ser Ser Val Ser Tyr Met
            20                  25                  30

His Trp Tyr Gln Gln Lys Pro Gly Gln Ser Pro Lys Pro Trp Ile Tyr
            35                  40                  45

Gly Thr Ser Lys Leu Ala Ser Gly Val Pro Asp Arg Phe Ser Gly Ser
        50                  55                  60

Gly Ser Gly Thr Ser Tyr Ser Leu Thr Ile Ser Ser Leu Gln Ala Glu
 65                  70                  75                  80

Asp Val Ala Val Tyr Tyr Cys Leu Gln Arg Ser Ser Tyr Pro Pro Thr

Phe Gly Gln Gly Thr Lys Val Glu Ile Lys
            100                 105

<210> SEQ ID NO 30
<211> LENGTH: 150
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 30 aattaacccct cactaaaggg gaattcgcgg ccgctctccc attcagtaat cagtcctgca      60
gcactgcaca gactcctcac catggacatc aggctcagct tggttttcct tgtccttttc     120
ataaaaggtg tccagtgtca ggtgcagctg                                      150

<210> SEQ ID NO 31
<211> LENGTH: 148
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 31
actccagccc cttccctgga gcctggcgga cccaggtcat gtaatagttg ctaaaggtga      60
atccagaggc tgcacaggag agtctcaggg acctcccagg ctgtacgacg cctcccccag     120
actccaccag ctgcacctga cactggac                                        148

<210> SEQ ID NO 32
<211> LENGTH: 150
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 32
tccagggaag gggctggagt gggtcgctta cattagtagt ggtggtggta gcacttacta      60
tcgagactcc gtgaagggcc ggttcaccat ctccagagac aattccaaga acacgctgta     120
tctgcaaatg aacagcctga gagccgagga                                      150

<210> SEQ ID NO 33
<211> LENGTH: 130
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 33
gaccgatggg cccttggtgg aggctgagga gacggtgacc aggttccct ggccccagta       60 agcaaaccaa tacccatagt cctctctcgc acagtaatat acggccgtgt cctcggctct     120
caggctgttc                                                            130

<210> SEQ ID NO 34
<211> LENGTH: 150
<212> TYPE: DNA
<213> ORGANISM: Artificial Sequence
<220> FEATURE:

<223> OTHER INFORMATION: Description of Artificial Sequence: synthetic
      DNA

<400> SEQUENCE: 34
aattaaccct cactaaaggg gaattctcca aacttcaagt acacaatgga ttttcaggtg   60
cagagtttca gcctcctgct aatcagtatc acagtcatag tgtccagtgg agacatcgtg  120
atgacccagt ctccagactc cctggctgtg                                   150

<210> SEQ ID NO 35
<211> LENGTH: 150
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 35
ccccagaagc cagcttggat gtgccgtaaa tgagcagctt aggaggctgt cctggtttct   60
gctggtacca gtgcatgtag cttacacttg agctggcacg gcagttgatg gtggccctct  120
cgcctagaga cacagccagg gagtctggag                                   150

<210> SEQ ID NO 36
<211> LENGTH: 150
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 36
atccaagctg gcttctgggg tccctgacag attcagtggc agcgggtctg ggacagattt   60
cactctcacc atcagcagcc tgcaggctga agatgtggca gtttattact gtctgcagag  120
gagtagttac ccaccaacgt tcggccaagg                                   150

<210> SEQ ID NO 37
<211> LENGTH: 72
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 37
gtaatacgac tcactatagg gcctcgagcg tacgtttgat ttccaccttg gtcccttggc   60
cgaacgttgg tg                                                       72

<210> SEQ ID NO 38
<211> LENGTH: 142
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 38
aattaaccct cactaaaggg gaattcgcgg ccgctctccc attcagtaat cagtcctgca   60
gcactgcaca gactcctcac catggacatc aggctcagct tggtttteet tgtccttttc  120 ataaaggtg tccagtgtga gg                                            142

<210> SEQ ID NO 39

```
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 39
ccagcccctt cgttggagcc                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 40
ggctccaacg aaggggctgg                                              20

<210> SEQ ID NO 41
<211> LENGTH: 92
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 41
gtacaacaga ggactatggg tattggtttg cttactgggg ccagggaacc ctggtcaccg   60
tctcctcagc ctccaccaag ggcccatcgg tc                                92

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 42
ccagaagcca gcttggatgt gccgtaaatc cagggcttag gggactgtcc              50

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 43
accatcacct gccgtgccag                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 44
gcacatccaa gctggcttct                                              20
```

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: synthetic DNA

<400> SEQUENCE: 45
agaagccagc ttggatgtgc                                              20

<210> SEQ ID NO 46
<211> LENGTH: 142
<212> TYPE: DNA
<213> ORGANISM: Artificial Sequence
<220> FEATURE:
<223> OTHER INFORMATION: Description of Artificial Sequence: synthetic DNA

<400> SEQUENCE: 46
aattaaccct cactaaaggg gaattctcca aacttcaagt acacaatgga ttttcaggtg    60
cagagtttca gcctcctgct aatcagtatc acagtcatag tgtccagtgg agacatcgtg   120
ctcacccagt ctccaacaac ca                                           142

<210> SEQ ID NO 47
<211> LENGTH: 130
<212> TYPE: DNA
<213> ORGANISM: Artificial Sequence
<220> FEATURE:
<223> OTHER INFORMATION: Description of Artificial Sequence: synthetic DNA

<400> SEQUENCE: 47
tccagggctt aggggactgt cctggttcct gctggaacca gtgcatgtag cttacacttg    60
agctggcacg gcaggtgatg gtggccctct cgcctggaga cacagccatg gttgttggag   120
actgggtgag                                                         130

<210> SEQ ID NO 48
<211> LENGTH: 133
<212> TYPE: DNA
<213> ORGANISM: Artificial Sequence
<220> FEATURE:
<223> OTHER INFORMATION: Description of Artificial Sequence: synthetic DNA

<400> SEQUENCE: 48
gacagtcccc taagccctgg atttacggca catccaagct ggcttctggg gtccctgaca    60
gattcagtgg cagcgggtct gggacatctt attctctcac catcagcagc ctgcaggctg   120
aagatgctgc aac                                                     133

<210> SEQ ID NO 49
<211> LENGTH: 123
<212> TYPE: DNA
<213> ORGANISM: Artificial Sequence
<220> FEATURE:
<223> OTHER INFORMATION: Description of Artificial Sequence: synthetic DNA

<400> SEQUENCE: 49
gtaatacgac tcactatagg gcctcgagcg tacgtttgat ttccaccttg gtcccttggc    60
cgaacgttgg tgggtaacta ctcctctgca gacagtaata agttgcagca tcttcagcct   120
gca                                                                123

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 50 aagggggaatt ctccaaactt caagtacaca                                   30

<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 51
agaagccagc ttggatgtgc cgtaaatgag gggcttaggg gactgtcctg              50

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 52
ggcagcgggt ctgggacatc ttattctctc accatcagca gcctg                   45

<210> SEQ ID NO 53
<211> LENGTH: 69
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 53
agaagccagc ttggatgtgc cgtaaatcca gggcttaggg gactgtcctg gtttctgctg   60
gaaccagtg                                                           69

<210> SEQ ID NO 54
<211> LENGTH: 118
<212> TYPE: PRT
<213> ORGANISM: Artificial Sequence
<220> FEATURE:
<221> NAME/KEY: gene
<222> LOCATION: (1)..(108)
<223> OTHER INFORMATION: Description of Artificial Sequence: synthetic
      protein

<400> SEQUENCE: 54

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Tyr Met Thr Trp Val Arg Gln Ala Pro Gly Lys Gly Leu Glu Trp Val
         35                  40                  45

Ser Tyr Ile Ser Ser Gly Gly Gly Ser Thr Tyr Tyr Arg Asp Ser Val
     50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Glu Asp Tyr Gly Tyr Trp Phe Ala Tyr Trp Gly Gln Gly Thr
        100                 105                 110

Leu Val Thr Val Ser Ser
        115

<210> SEQ ID NO 55
<211> LENGTH: 106
<212> TYPE: PRT
<213> ORGANISM: Artificial Sequence
<220> FEATURE:
<221> NAME/KEY: gene
<222> LOCATION: (1)..(106)
<223> OTHER INFORMATION: Description of Artificial Sequence: synthetic
      protein

<400> SEQUENCE: 55

Asp Ile Gln Met Thr Gln Ser Pro Ser Ser Leu Ser Ala Ser Val Gly
  1               5                  10                  15

Asp Arg Val Thr Ile Thr Cys Arg Ala Ser Ser Ser Val Ser Tyr Met
             20                  25                  30

His Trp Tyr Gln Gln Lys Pro Gly Lys Ala Pro Lys Leu Leu Ile Tyr
         35                  40                  45

Gly Thr Ser Lys Leu Ala Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Leu Gln Arg Ser Ser Tyr Pro Pro Thr
             85                  90                  95

Phe Gly Gln Gly Thr Lys Val Glu Ile Lys
        100                 105

<210> SEQ ID NO 56
<211> LENGTH: 18
<212> TYPE: PRT
<213> ORGANISM: Homo sapiens

<400> SEQUENCE: 56

Gly Pro Glu Thr Leu Ser Gly Ala Glu Leu Val Asp Ala Leu Gln Phe
  1               5                  10                  15

Val Cys

<210> SEQ ID NO 57
<211> LENGTH: 18
<212> TYPE: PRT
<213> ORGANISM: Homo sapiens

<400> SEQUENCE: 57

Cys Leu Gln Phe Val Ala Gly Asp Arg Gly Tyr Phe Asn Lys Pro
  1               5                  10                  15

Thr Gly

<210> SEQ ID NO 58
<211> LENGTH: 13
<212> TYPE: PRT
<213> ORGANISM: Homo sapiens
```

```
<400> SEQUENCE: 58

Cys Tyr Phe Asn Lys Pro Thr Gly Tyr Gly Ser Ser Ser
 1               5                  10

<210> SEQ ID NO 59
<211> LENGTH: 14
<212> TYPE: PRT
<213> ORGANISM: Homo sapiens

<400> SEQUENCE: 59

Cys Thr Gly Tyr Gly Ser Ser Ser Arg Arg Ala Pro Gln Thr
 1               5                  10

<210> SEQ ID NO 60
<211> LENGTH: 12
<212> TYPE: PRT
<213> ORGANISM: Homo sapiens

<400> SEQUENCE: 60

Arg Arg Ala Pro Gln Thr Gly Ile Val Asp Glu Cys
 1               5                  10

<210> SEQ ID NO 61
<211> LENGTH: 17
<212> TYPE: PRT
<213> ORGANISM: Homo sapiens

<400> SEQUENCE: 61

Cys Thr Gly Ile Val Asp Glu Ala Ala Phe Arg Ser Ala Asp Leu Arg
 1               5                  10                  15

Arg

<210> SEQ ID NO 62
<211> LENGTH: 19
<212> TYPE: PRT
<213> ORGANISM: Homo sapiens

<400> SEQUENCE: 62

Cys Asp Leu Arg Arg Leu Glu Met Tyr Ala Ala Pro Leu Lys Pro Ala
 1               5                  10                  15

Lys Ser Ala

<210> SEQ ID NO 63
<211> LENGTH: 9
<212> TYPE: PRT
<213> ORGANISM: Homo sapiens

<400> SEQUENCE: 63

Asp Leu Arg Arg Leu Glu Met Tyr Cys
 1               5

<210> SEQ ID NO 64
<211> LENGTH: 10
<212> TYPE: PRT
<213> ORGANISM: Homo sapiens

<400> SEQUENCE: 64

Cys Ala Pro Leu Lys Pro Ala Lys Ser Ala
 1               5                  10

<210> SEQ ID NO 65
<211> LENGTH: 17
<212> TYPE: PRT
```

<213> ORGANISM: Homo sapiens

<400> SEQUENCE: 65

Cys Thr Gly Ile Val Asp Glu Cys Cys Phe Arg Ser Cys Asp Leu Arg
 1               5                  10                  15

Arg

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 66
gatgaattca gaagcaatgg gaaaaatcag cagtc                              35

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 67
cattgtcgac gcatgtcact cttcactcct ca                                 32

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 68
taaagaattc gcggccgctc tccc                                          24

<210> SEQ ID NO 69
<211> LENGTH: 49
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 69
taaagtcgac gggcccttgg tggaggctga agagacagtg accagagtg               49

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 70
taaagaattc tccaaacttc aagtacacaa tgg                                33

<210> SEQ ID NO 71
<211> LENGTH: 35
<212> TYPE: DNA
<213> ORGANISM: Artificial Sequence -continued

```
<220> FEATURE:
<223> OTHER INFORMATION: Description of Artificial Sequence: synthetic
      DNA

<400> SEQUENCE: 71
taaagtcgac cgtacgtttc agttccagct tggtc                                    35
```

US 7,498,415 B2

RECOMBINANT ANTIBODY AGAINST HUMAN INSULIN-LIKE GROWTH FACTOR

This application is a national stage of PCT Application No. PCT/JP2004/014453 filed Sep. 24, 2004, which claims benefit of Japanese Application No. 2003-331509 filed Sep. 24, 2003.

TECHNICAL FIELD

The present invention relates to a recombinant antibody or an antibody fragment thereof which specifically binds to human insulin-like growth factor-I (hereinafter referred to as hIGF-I) and human insulin-like growth factor-II (hereinafter referred to as hIGF-II) to inhibit the biological activities of human IGF-I and human IGF-II, a transformant producing the antibody or the antibody fragment thereof, a process for producing the antibody or the antibody fragment thereof, and a medicament comprising the antibody or the antibody fragment thereof as the active ingredient therein.

BACKGROUND ART

IGF plays an important role in the regulation of the proliferation, differentiation and cell death (apoptosis) of epithelial cells in organs such as breast, prostate, lung, and colon. The biological activity thereof is mediated by the IGF receptor (referred to as IGF-R hereinafter) (Endocrine Reviews, 16, 3, 1995). Additionally, there exist 10 types of IGF-binding proteins (referred to as IGFBP hereinafter) which not only suppress IGF metabolism but also regulate transferring of IGF and binding with the IGF receptors (Journal of Biological Chemistry, 264, 11843, 1989).

IGF includes two types, IGF-I and IGF-II, comprising a single chain polypeptide. Both of them have 40% homology with an insulin precursor proinsulin at the amino acid level (Advances in Cancer Research, 68, 183, 1996). In intravital, insulin receptor, IGF-I receptor (hereinafter referred to as IGF-R), IGF-II receptor (hereinafter referred to as IGF-IIR) and hybrid receptors of the insulin receptor and IGF-R is acting as the receptors of IGFs.

The insulin receptor and the IGF-R are both tyrosine kinase-type receptors (Endocrine Reviews, 16, 143, 1995, Breast Cancer Research & Treatment, 47, 235, 1998). At the amino acid levels, both of them have an about 60% homology. Each of the insulin receptor and the IGF-R have a high binding specificity to their specific ligands, namely insulin and IGF-I but they also have a binding property to insulin, IGF-I or IGF-II (Journal of Biological Chemistry, 263, 11486, 1988, Journal of Biological Chemistry, 268, 7393, 1993), respectively. Further, it is considered that hybrid receptors comprising each subunit of insulin receptor and IGF-R have higher binding specificities to IGF-I than to insulin and act as IGF-R. However, the biological functions thereof are unknown (Endocrine Reviews, 16, 3-34, 1995, Endocrine Reviews, 16, 143, 1995). IGF-IIR can bind to IGF-II alone in the IGF family. Since IGF-IIR has no tyrosine kinase activity, it is considered that IGF-IIR may act as an IGF-II antagonist (Proceedings of the National Academy of Sciences of the United States of America, 94, 12981, 1997). As described above, the 2 types of IGFs form complex networks with the 10 types of IGF-binding proteins (hereinafter referred to as IGFBP) in addition to these 4 types of receptors, and are acting in intravital.

It is known that IGF is expressed in a wide variety of cancers such as sarcoma, leukemia, prostate cancer, breast cancer, lung cancer, colon cancer, gastric cancer, esophagus cancer, hepatic cancer, pancreatic cancer, renal cancer, thyroid gland cancer, brain tumor, ovarian cancer and uterine cancer, and IGF has a strong proliferation-promoting activity for these cancer cells (British Journal of Cancer, 65, 311, 1992, Anticancer Research, 11, 1591, 1991, Annals of Internal Medicine, 122, 54, 1995, Oncology, 54, 502, 1997, Endocrinology, 137, 1764, 1996). Also, it is known that IGF-II and IGF-R are more highly expressed in highly metastatic cancers than in poorly metastatic cancers (International Journal of Cancer, 65, 812, 1996). It is therefore suggested that IGF may be in cancer metastasis. The IGF promoting cell proliferation activity is mainly mediated by IGF-R (Endocrinology, 136, 4298, 1995, Oncogene, 28, 6071, 1999). However, it is also known that IGF-II acts through insulin receptor in some types of breast cancer cells (Oncogene, 18, 2471, 1999).

Clinical and epidemiological examinations have issued reports about the increase of IGF or IGF-R level in many cancer tissues such as breast cancer (Cancer Epidemiology, Biomarkers & Preventions, 11, 1566, 2002, European Journal of Cancer, 29A, 492, 1993), neuroblastoma, lung cancer (Journal of the National Cancer Institute, 92, 737, 2000), colorectal cancer (Gut, 44, 704, 1999), prostate cancer (Cancer Research, 62, 2942, 2002, Science, 279, 563, 1998), ovarian cancer (International Journal of Cancer, 101, 549, 2002), bladder cancer (Journal of Urology, 169, 714, 2003) and osteosarcoma or in serum IGF level (Journal of the National Cancer Institute, 92, 1472, 2002). Further, it is reported that cancer patients with IGF-R expression have poor prognosis (Cancer Research, 57, 3079, 1997).

It is known that the cell death of colorectal cancer cells as induced by interferon or tumor necrosis factor with an cell death-inducing activity is suppressed by IGF-I. It is additionally known that compared with radiologically sensitive cancer cells in primary culture cells derived from glioblastoma patients, the expression levels of IGF-IR and phosphorylated IGF-IR in radiologically resistant cancer cells therein are increased and that when the functions of receptors of the epidermal growth factor in the radiologically sensitive cancer cells are inhibited, it is known that the IGF-R expression levels increased. The above findings reveal that IGF has an effect of promoting the proliferation of cancer cells but also is involved in the enhancement of the survival signal of cancer cells via IGF-R to allow the cancer cells to acquire drug resistance (Journal of the National Cancer Institute, 93, 1852, 2001, Oncogene, 20, 1913, 2001, Cancer Research, 60, 2007, 2000, Cancer Research, 62, 200, 2002).

Further, as the diseases other than cancers, diseases related with IGFs are reported. Among gigantism and acromegaly, it is also considered that abnormal IGF expression caused secondarily by abnormal growth hormone secretion is therefore involved in the progress of the pathology (Growth Hormone & IGF Research, 13, 98, 2003). Additionally, IGF-I involvement is also suggested in diabetic complications (Science, 276, 1706, 1997, American Journal of Physiology, 274, F1045, 1998) and the onset of the pathology of rheumatoid arthritis (Journal of Clinical Endocrinology & Metabolism, 81, 150, 1996, Arthritis & Rheumatism, 39, 1556, 1996).

Research works using model animals have been made to examine the relations between IGF and various diseases. It is known that in human prostate cancer-grafted model mice, as the mice acquire an androgen-independent proliferation, IGF-I and IGF-R expression levels increase (Cancer Research, 61, 6276, 2001). Additionally, most of serum IGF is generated in liver. It is known however that serum IGF is involved in cancer growth since the growth of colorectal tumor orthotopically grafted in IGF-I deficient-mice of in liver alone is suppressed (Cancer Research, 62, 1030, 2002).

Cancer development or hypertrophy is observed in mice which expresses of IGF at specific focus in intravitals (Oncogene, 22, 853, 2003, Cancer Research, 60, 1561, 2000, Journal of Biological Chemistry, 269, 13779, 1994).

As described above, IGF, IGF-R and IGFBP play important roles not only in development, growth and metastasis of cancer but also in acromegaly, diabetic complications, rheumatoid arthritis and the like.

Anti-tumor effect which inhibits the signal transduction between IGF and IGF-R has been examined so far. It is reported that anti-IGF-IR antibodies targeting IGF-IR (Cancer Research, 63, 5073, 2003, WO 02/53596), IGF-R inhibitors (WO 99/28347) or IGFBP capable of inhibiting serum IGF can demonstrate an anti-tumor effect in animal models (Cancer research, 62, 3530, 2002).

Although the anti-IGF-IR antibodies can inhibit the engraftment of human breast cancer cells with estrogen-independent growth as grafted in mice, it is revealed that the antibodies do not suppress the engraftment of human breast cancer cells with estrogen-dependent proliferation or the proliferation of the engrafted human breast cancer cells. It is thus revealed that the inhibition of the function of IGF-IR alone does not provide sufficient anti-tumor effect (Breast Cancer Research & Treatment, 22, 101, 1992).

Various antibodies are known as antibodies against IGF (hereinafter referred to as anti-hIGF antibodies). Typical antibodies against human IGF-I (hereinafter referred to as anti-hIGF-I antibodies) include anti-hIGF-I mouse antibody sm1.2 (Proceedings of the National Academy of Sciences of the United States of America, 81, 2389, 1984). Antibodies against human IGF-II (hereinafter referred to as anti-hIGF-II antibodies) include anti-hIGF-II mouse antibody S1F2 (Endocrinology, 124, 870, 1989). sm1.2 has 40% crossreactivity with IGF-II, while S1F2 has about 10% crossreactivity with hIGF-I. It is known that both antibodies can inhibit hIGF-I- or hIGF-II-dependent cell proliferation in vitro.

When an antibody of a non-human animal, such as a mouse antibody is administered to human, the mouse antibody is recognized as a foreign substance. The administered antibody not only initiates side effects but also disappears rapidly. Therefore, the antibody is not useful for therapy. In order to solve these problems, attempts have been made to convert an antibody of a non-human animal into a humanized antibody, such as a human chimeric antibody or a human complimentarity-determining region (hereinafter referred to as CDR)-grafted antibody, using genetic engineering techniques. The human chimeric antibody is an antibody wherein the variable region (hereinafter referred to as V region) is an non-human animal antibody and the constant region (hereinafter referred to as C region) is a human antibody (Proceedings of the National Academy of Sciences of the United States of America, 81, 6851, 1984), and the human CDR-grafted antibody is an antibody wherein the amino acid sequences of CDRs in the V region of a non-human animal antibody of is grafted into an appropriate position of a human antibody (Nature, 321, 522, 1986). Compared to a non-human animal antibody, such as mouse antibodies, these humanized antibodies are more advantages in clinical use. With respect to immunogenicity and stability in blood, for example, a report tells that when administered to human, the half-life in blood of human chimeric antibodies has been extended an about 6-fold, in comparison with those of mouse antibodies (European Journal of Cancer, 29A, 492, 1993). It is also reported that human CDR-grafted antibodies, the immunogenicity has decreased in experiments using monkeys, and the half life in blood has extended compared with mouse antibodies (Cancer Research, 56, 1118, 1996, Immunology, 85, 668, 1995).

Compared to non-human animal antibodies, it is expected that humanized antibodies have less side effects and have a therapeutic effect for a longer time. Additionally because the humanized antibodies are prepared by genetic engineering techniques, such humanized antibodies can be prepared as molecules having various forms. Due to the recent advances in protein engineering and genetic engineering, antibody fragments having a smaller molecular weight such as Fab, Fab', F(ab')$_2$, scFv (Science, 242, 423, 1988), dsFv (Molecular Immunology, 32, 249, 1995) and CDR-containing peptide (Journal of Biological Chemistry, 271, 2966, 1996) can be prepared from antibodies including humanized antibodies. Because these antibody fragments have a smaller molecular weight than whole antibody molecules, these antibody fragments have superior transitional activity into target tissues (Cancer Research, 52, 3402, 1992).

DISCLOSURE OF THE INVENTION

An objection of the present invention is to provide a recombinant antibody or an antibody fragment thereof which specifically binds to IGF-I and IGF-II to inhibit the biological activities of hIGF-I and hIGF-II, a transformant producing the antibody or the antibody fragment thereof, a process for producing the antibody or the antibody fragment thereof, and a medicament comprising the antibody or the antibody fragment thereof as the active ingredient.

The invention relates to following (1) to (28).

(1) A recombinant antibody or an antibody fragment thereof wherein the recombinant antibody or the antibody fragment thereof specifically binds to human insulin-like growth factor-I (IGF-I) and human insulin-like growth factor-II (IGF-II) to inhibit the biological activities of human IGF-I and human IGF-II.

(2) The recombinant antibody or the antibody fragment thereof according to (1), wherein the recombinant antibody or the antibody fragment thereof binds to human IGF-I and human IGF-II at the same degree.

(3) The recombinant antibody or the antibody fragment thereof according to (1) or (2), wherein the recombinant antibody or the antibody fragment thereof has the binding activity with a binding constant of $5 \times 10^9$ $M^{-1}$ or more measured with a biosensor BIACORE to human IGF-I and human IGF-II.

(4) The recombinant antibody or the antibody fragment thereof according to any one of (1) to (3), wherein the recombinant antibody or the antibody fragment thereof belongs to the IgG class.

(5) The recombinant antibody or the antibody fragment thereof according to any one of (1) to (4), wherein the recombinant antibody comprises the complimentarity-determining regions (CDRs) of the heavy chain variable region (VH) and light chain variable region (VL) of a monoclonal antibody against human IGF.

(6) The recombinant antibody or the antibody fragment thereof according to (5), wherein the complimentarity-determining region (CDR)1, CDR2 and CDR3 of the VH of the recombinant antibody or the antibody fragment thereof are represented by SEQ ID NOs:5, 6 and 7, respectively.

(7) The recombinant antibody or the antibody fragment thereof according to (5), wherein the CDR1, CDR2 and CDR3 of the VL of the recombinant antibody or the antibody fragment thereof are represented by SEQ ID NOs:8, 9 and 10, respectively.

(8) The recombinant antibody or the antibody fragment thereof according to any one of (5) to (7), wherein the CDR1, CDR2 and CDR3 of the VH of the recombinant antibody or the antibody fragment thereof are represented by SEQ ID NOs:5, 6 and 7, respectively and the CDR1, CDR2 and CDR3 of the VL are represented by SEQ ID NOs:8, 9 and 10, respectively.

(9) The recombinant antibody or the antibody fragment thereof according to any one of (5) to (8), wherein the VH of the recombinant antibody or the antibody fragment thereof comprises an amino acid sequence in which at least one amino acid selected from 1st position Gln, 11th position Val, 42nd position Gly, 75th position Ser, 77th position Asn, 84th position Asn, 93rd position Val, 97th position Ala, and 98th position Arg in the amino acid sequence represented by SEQ ID NO:11 is substituted or an amino acid sequence in which at least one amino acid selected from 49th position Ser, 77th position Asn, 84th position Asn, 93rd position Val, 97th position Ala, and 98th position Arg in the amino acid sequence represented by SEQ ID NO:54 is substituted.

(10) The recombinant antibody or the antibody fragment thereof according to any one of (5) to (8), wherein the VL of the recombinant antibody or the antibody fragment thereof the antibody comprises an amino acid sequence in which at least one amino acid selected from 4th position Met, 9th position Asp, 10th position Ser, 11th position Leu, 15th position Leu, 22th position Asn, 35th position Tyr, 39th position Pro, 42th position Pro, 45th position Leu, 46th position Leu, 69th position Asp, 70th position Phe, 71st position Thr, 82nd position Val, and 84th position Val in the amino acid sequence represented by SEQ ID NO:14 is substituted or an amino acid sequence in which at least one amino acid selected from 4th position Met, 9th position Ser, 10th position Ser, 11th position Leu, 15th position Val, 35th position Tyr, 39th position Pro, 42nd position Ala, 45th position Leu, 46th position Leu, 69th position Asp, 70th position Phe, 71th position Thr, and 82nd position Phe in the amino acid sequence represented by SEQ ID NO:55 is substituted.

(11) The recombinant antibody or the antibody fragment thereof according to any one of (5) to (10), wherein the VH of the recombinant antibody or the antibody fragment thereof comprises an amino acid sequence in which at least one amino acid selected from 1st position Gln, 11th position Val, 42th position Gly, 75th position Ser, 77th position Asn, 84th position Asn, 93rd position Val, 97th position Ala, and 98th position Arg in the amino acid sequence represented by SEQ ID NO:11 is substituted or an amino acid sequence in which at least one amino acid selected from 49th position Ser, 77th position Asn, 84th position Asn, 93rd position Val, 97th position Ala, and 98th position Arg in the amino acid sequence represented by SEQ ID NO:54 is substituted and the VL comprises an amino acid sequence in which at least one amino acid selected from 4th position Met, 9th position Asp, 10th position Ser, 11th position Leu, 15th position Leu, 22th position Asn, 35th position Tyr, 39th position Pro, 42th position Pro, 45th position Leu, 46th position Leu, 69th position Asp, 70th position Phe, 71st position Thr, 82nd position Val, and 84th position Val in the amino acid sequence represented by SEQ ID NO:14 is substituted or an amino acid sequence in which at least one amino acid selected from 4th position Met, 9th position Ser, 10th position Ser, 11th position Leu, 15th position Val, 35th position Tyr, 39th position Pro, 42nd position Ala, 45th position Leu, 46th position Leu, 69th position Asp, 70th position Phe, 71st position Thr, and 82nd position Phe in the amino acid sequence represented by SEQ ID NO:55 is substituted.

(12) The recombinant antibody or the antibody fragment thereof according to any one of (5) to (11), wherein the VH of the recombinant antibody or the antibody fragment thereof comprises an amino acid sequence in which at least one amino acid selected from 1st position Gln, 11th position Val, 42nd position Gly, 75th position Ser, 77th position Asn, 84th position Asn, 93rd position Val, 97th position Ala, and 98th position Arg in the amino acid sequence represented by SEQ ID NO:11 is substituted and the VL comprises an amino acid sequence in which at least one amino acid selected from 4th position Met, 9th position Asp, 10th position Ser, 11th position Leu, 15th position Leu, 22nd position Asn, 35th position Tyr, 39th position Pro, 42nd position Pro, 45th position Leu, 46th position Leu, 69th position Asp, 70th position Phe, 71st position Thr, 82nd position Phe, and 84th position Val in the amino acid sequence represented by SEQ ID NO:14 is substituted.

(13) The recombinant antibody or the antibody fragment thereof according to any one of (5) to (11), wherein the VH of the recombinant antibody or the antibody fragment thereof comprises an amino acid sequence in which at least one amino acid selected from 49th position Ser, 77th position Asn, 84th position Asn, 93rd position Val, 97th position Ala, and 98th position Arg in the amino acid sequence represented by SEQ ID NO:54 is substituted and the VL comprises an amino acid sequence in which at least one amino acid selected from 4th position Met, 9th position Ser, 10th position Ser, 11th position Leu, 15th position Val, 35th position Tyr, 39th position Pro, 42th position Ala, 45th position Leu, 46th position Leu, 69th position Asp, 70th position Phe, 71st position Thr, and 82nd position Phe in the amino acid sequence represented by SEQ ID NO:55 is substituted.

(14) The recombinant antibody or the antibody fragment thereof according to any one of (5) to (8) or (12), wherein the VH of the recombinant antibody or the antibody fragment thereof comprises an amino acid sequence represented by SEQ ID NO:26.

(15) The recombinant antibody or the antibody fragment thereof according to any one of (5) to (8) or (12), wherein the VL of the recombinant antibody or the antibody fragment thereof comprises an amino acid sequence represented by SEQ ID NO:27, 28 or 29.

(16) The recombinant antibody or the antibody fragment thereof according to any one of (5) to (8), (12), (14) or (15), wherein the VH of the recombinant antibody or the antibody fragment thereof comprises an amino acid sequence represented by SEQ ID NO:26 and the VL comprises an amino acid sequence represented by SEQ ID NO:27, 28 or 29.

(17) The recombinant antibody or the antibody fragment thereof according to any one of (5) to (8), (12), and (14) to (16), wherein the VH of the recombinant antibody or the antibody fragment thereof comprises an amino acid sequence represented by SEQ ID NO:26 and the VL comprises an amino acid sequence represented by SEQ ID NO:27.

(18) The recombinant antibody or the antibody fragment thereof according to any one of (5) to (8), (12), (14) to (16), wherein the VH of the recombinant antibody or the antibody fragment thereof comprises an amino acid sequence represented by SEQ ID NO:26 and the VL comprises an amino acid sequence represented by SEQ ID NO:28.

(19) The recombinant antibody or the antibody fragment thereof according to any one of (5) to (8), (12), (14) to (16), wherein the VH of the recombinant antibody or the antibody fragment thereof comprises an amino acid sequence represented by SEQ ID NO:26 and the VL comprises an amino acid sequence represented by SEQ ID NO:29.
(20) The recombinant antibody or the antibody fragment thereof according to any one of (1) to (19), wherein the recombinant antibody is a human CDR-grafted antibody.
(21) The antibody fragment thereof according to any one of (1) to (19), wherein the antibody fragment is an antibody fragment selected from Fab, Fab', F(ab')$_2$, single-stranded antibody (scFv), dimerized variable region (diabody), disulfide-stabilized variable region (dsFv), and CDR-containing peptide.
(22) DNA encoding the recombinant antibody or the antibody fragment thereof according to any one of (1) to (21).
(23) An expression vector carrying the DNA according to (22).
(24) A transformant obtained by introducing the expression vector according to (23).
(25) A process for producing a recombinant antibody or the antibody fragment thereof, which comprises a step of culturing the transformant according to (24) in a medium to produce and accumulate the recombinant antibody or the antibody fragment thereof according to any one of (1) to (21) in a culture, and isolating and purifying the recombinant antibody or the antibody fragment thereof from the culture.
(26) A medicament which comprises the recombinant antibody or the antibody fragment thereof according to any one of (1) to (21) as an active ingredient.
(27) A therapeutic agent for IGF-associated diseases, which comprises the recombinant antibody or the antibody fragment thereof according to (1) to (21).
(28) A therapeutic agent according to (27), wherein the IGF-associated diseases are cancer, acromegaly and diabetic complications.

Examples of the recombinant antibody or the antibody fragment thereof of the present invention includes any recombinant antibody or an antibody fragment thereof which specifically binds to hIGF-I and hIGF-II to inhibit the biological activities of hIGF-I and hIGF-II. Preferable are such recombinant antibody or an antibody fragment thereof binds to hIGF-I and to hIGF-II at the same degree.

The recombinant antibody or the antibody fragment thereof of the present invention which specifically binds to hIGF-I and hIGF-II can be prepared from a monoclonal antibody against hIGF-I and having a crossreactivity with hIGF-II, or a monoclonal antibody against hIGF-II and having a crossreactivity with hIGF-I, using genetic engineering techniques.

The phrase "an antibody which binds to hIGF-I and to hIGF-II at the same degree" means the antibody which has a binding activity to hIGF-I and hIGF-II approximately at the same degree.

The binding activity can be numerically expressed by known assay methods. The known assay methods include, for example, enzyme immunoassay (hereinafter referred to as ELISA) and a biosensor method (hereinafter referred to as biosensor Biacore) using the principle of surface plasmon resonance (Journal of Immunological Method, 145, 229, 1991). According to the biosensor Biacore assay, a trace mass change emerging on the surface of the sensor chip following the binding and dissociation between two molecules is detected as SPR signal via an optical phenomenon.

Measuring methods by ELISA include a method of measuring the binding activities of an antibody to both IGF-I and IGF-II, for example, a method which comprises comparing the results of IGF-I with the results of IGF-II obtained by assaying the amount of an antibody which binds to an immobilized antigen by ELISA; and method of comparing the results of IGF-I with the results of IGF-II obtained by a competitive ELISA method (Antibodies; A Laboratory Manual, Cold Spring Harbor Laboratory, Chapter 14, 1988) of measuring the decrease of an antibody which binds to an immobilized antigen by ELISA as described above by concurrently adding the antigen during the reaction of the antibody.

The phrase "the antibody which binds to hIGF-I and to hIGF-II at the same degree" means that when comparing the binding activity of the antibody to hIGF-I and hIGF-II numerically expressed by using the methods as shown above as under the definition of the binding activity of the antibody to hIGF-I as 1, the binding activity thereof to hIGF-II is 0.1 to 10, preferably 0.2 to 5, more preferably 0.5 to 2 and most preferably 1.

Inhibiting the biological activities of both hIGF-I and hIGF-II means inhibiting the signal transduction from hIGF-I and hIGF-II via a specific receptor of hIGF-I or hIGF-II, to inhibit the biological activities of hIGF-I and hIGF-II. Example includes that to inhibit the binding of hIGF-I and hIGF-II to such specific receptor of hIGF-I or hIGF-II. Such activity of antibody to inhibit the activity of antigen is referred to as the neutralizing activity of antibody.

The biological activities of hIGF-I and hIGF-II include an activity to promote cell proliferation via a specific receptor of hIGF-I or hIGF-II.

The specific receptor of hIGF-I or hIGF-II means receptors capable of binding to hIGF-I or hIGF-II and includes IGF-I receptor, IGF-II receptor, insulin receptor, hybrid receptors of hIGF-I with insulin receptor, and the like.

The recombinant antibody or an antibody fragment thereof of the present invention includes any recombinant antibody or an antibody fragment thereof which specifically binds to hIGF-I and hIGF-II to inhibit the functions of hIGF-I and hIGF-II. A recombinant antibody with a binding constant to human IGF-I and human IGF-II being preferably $1\times10^9$ M$^{-1}$, more preferably $2\times10^9$ M$^{-1}$, still more preferably $3\times10^9$ M$^{-1}$, and most preferably $5\times10^9$ M$^{-1}$ is used.

The recombinant antibody of the present invention includes antibodies prepared by genetic engineering techniques. Such recombinant antibody is preferably a recombinant antibody comprising the constant region of human antibody, more preferably a recombinant antibody comprising the constant region of human antibody and the framework (hereinafter referred to as FR) of the variable region of human antibody. Such recombinant antibody includes for example human chimeric antibodies, human complimentarity-determining region (hereinafter referred to as CDR)-grafted antibodies, human antibodies produced by hybridomas prepared in genetic recombinant non-human animals, and human antibodies prepared into monoclones using genetic engineering techniques. Additionally, the recombinant antibody includes recombinant antibodies prepared by linking an antibody CDR selected from antibody gene libraries prepared artificially to the FR of an appropriate human antibody and then linking the constant region or the like of a human antibody.

Human chimeric antibody means an antibody comprising an antibody heavy chain variable region (hereinafter referred to as HV or VH, provided that variable region is referred to as V region and heavy chain is referred to as H chain), an antibody light chain variable region (hereinafter referred to as LV or VL, provided that light chain is referred to as L chain) of a non-human animal, and the heavy chain constant region (hereinafter referred to as CH) and light chain constant region (hereinafter referred to as CL) of human antibody. As the non-human animal, any animal such as mouse, rat, hamster and rabbit may be used, so long as hybridoma can be prepared.

Human chimeric antibody can be prepared by obtaining cDNAs encoding VH and VL from a hybridoma producing a monoclonal antibody, inserting the cDNAs respectively into an expression vector for a host cell having genes encoding human antibody CH and human antibody CL, to construct a human chimeric antibody expression vector, and then introducing the expression vector into a host cell for expression.

As CH of the human chimeric antibody, although any CH may be used so long as it belongs to human immunoglobulin (hereinafter referred to as hIg), that of an hIgG class is preferred and any of subclasses hIgG1, hIgG2, hIgG3 and hIgG4 belonging to an hIgG class may be used as well. With regard to CL of a human chimeric antibody, any CL may be used so long as it belongs to hIg and any of a κ class and a λ class may be used.

The human chimeric antibody of the present invention includes any human chimeric antibody so long as it can specifically binds to hIGF-I and hIGF-II to inhibit the functions of hIGF-I and hIGF-II. Specifically, the human chimeric antibody of the present invention includes human chimeric antibody prepared from anti-hIGF rat monoclonal KM1468 (FERM BP-7978), human chimeric antibody with VH comprising an amino acid sequence represented by SEQ ID NO:2 and/or VL comprising an amino acid sequence represented by SEQ ID NO:4, and anti-hIGF human chimeric antibody KM3002 produced by a transformant KM3002 (FERM BP-7996), and the like.

Human CDR-grafted antibody means an antibody in which CDRs of the VH and VL of an antibody derived from a non-human animal are grafted to appropriate positions of VH and VL of a human antibody.

Human CDR-grafted antibody can be prepared by designing amino acid sequences of a V region in which CDR amino acid sequences of the VH and VL of an antibody derived from a non-human animal are grafted to the FR sequences of the VH and VL of a human antibody, constructing cDNAs encoding the amino acid sequences, inserting the cDNAs, respectively into an expression vector for a host cell having genes encoding the CH and CL of human antibody to construct a human CDR-grafted antibody expression vector, and introducing the expression vector into a host cell to express the human CDR-grafted antibody. The V region amino acid sequences, wherein the CDR amino acid sequences of the VH and VL derived from a non-human animal as grafted into the FR sequences of VH and VL to the human antibody, may be designed as a sequence with several mutations introduced therein. cDNAs encoding such amino acid sequences thus designed may be obtained by site-specific mutagenesis method described in Molecular Cloning: A Laboratory Manual, Cold Spring Harbor Lab. Press New York, 1989, Current Protocols in Molecular Biology, Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci., USA, 82, 488 (1985) or the like. The number of amino acids substituted is 1 or more and the number is not limited thereto. The number is approximately a number of amino acids to be deleted, substituted or added by well known techniques such as site-specific mutagenesis. For example, the number is 1 to several tens, preferably 1 to 20, more preferably 1 to 10, still more preferably 1 to 5.

Any CH in the CDR-grafted antibody can be used, so long as it belongs to hIg. Preferably, an hIgG class, and any one of γ1, γ2, γ3 and γ4 subclasses belonging to hIgG can be used.

Also, any CL of the human CDR-grafted antibody can be used, so long as it belongs to hIg, and those of κ class or λ class can be used.

The human CDR-grafted antibody of the present invention includes any human CDR-grafted antibody so long as it can specifically binds to hIGF-I and hIGF-II to inhibit the functions of hIGF-I and hIGF-II. Preferably, the human CDR-grafted antibody comprising the CDRs of the VH and VL of an anti-human IGF antibody, human CDR-grafted antibody comprising the CDRs of the VH and VL of an anti-hIGF rat monoclonal KM1468 produced by rat hybridoma KM1468 (FERM BP-7978), human CDR-grafted antibody comprising the CDR1, CDR2 and CDR3 of the VH of the antibody having amino acid sequences represented by SEQ ID NOs:5, 6 and 7 and/or the CDR1, CDR2 and CDR3 of the VL of the antibody having amino acid sequences represented by SEQ ID NOs:8, 9 and 10, respectively and the like are exemplified.

Among these human CDR-grafted antibodies, preference is given to a human CDR-grafted antibody wherein the VH of the antibody comprises an amino acid sequence selected from amino acid sequences in which at least one amino acid selected from 1st position Gln, 11th position Val, 42nd position Gly, 75th position Ser, 77th position Asn, 84th position Asn, 93rd position Val, 97th position Ala, and 98th position Arg in the amino acid sequence represented by SEQ ID NO:11 is substituted and amino acid sequences in which at least one amino acid selected from 49th position Ser, 77th position Asn, 84th position Asn, 93rd position Val, 97th position Ala, and 98th position Arg in the amino acid sequence represented by SEQ ID NO:54 is substituted; a human CDR-grafted antibody wherein the VL of the antibody comprises an amino acid sequence selected from amino acid sequences in which at least one amino acid selected from 4th position Met, 9th position Asp, 10th position Ser, 11th position Leu, 15th position Leu, 22th position Asn, 35th position Tyr, 39th position Pro, 42th position Pro, 45th position Leu, 46th position Leu, 69th position Asp, 70th position Phe, 71st position Thr, 82nd position Val, and 84th position Val in the amino acid sequence represented by SEQ ID NO:14 is substituted and amino acid sequences in which at least one amino acid selected from 4th position Met, 9th position Ser, 10th position Ser, 11th position Leu, 15th position Val, 35th position Tyr, 39th position Pro, 42nd position Ala, 45th position Leu, 46th position Leu, 69th position Asp, 70th position Phe, 71st position Thr, and 82nd position Phe in the amino acid sequence represented by SEQ ID NO:55 is substituted; and a human CDR-grafted antibody wherein the VH of the antibody comprises an amino acid sequence selected from amino acid sequences in which at least one amino acid selected from 1st position Gln, 11th position Val, 42nd position Gly, 75th position Ser, 77th position Asn, 84th position Asn, 93rd position Val, 97th position Ala, and 98th position Arg in the amino acid sequence represented by SEQ ID NO:11 is substituted and amino acid sequences in which at least one amino acid selected from 49th position Ser, 77th position Asn, 84th position Asn, 93rd position Val, 97th position Ala, and 98th position Arg in the amino acid sequence represented by SEQ ID NO:54 is substituted and wherein the VL of the antibody comprises an amino acid sequence selected from amino acid sequences in which at least one amino acid selected from 4th position Met, 9th position Asp, 10th position Ser, 11th position Leu, 15th position Leu, 22th position Asn, 35th position Tyr, 39th position Pro, 42nd position Pro, 45th position Leu, 46th position Leu, 69th position Asp, 70th position Phe, 71st position Thr, 82nd position Val, and 84th position Val in the amino acid sequence represented by SEQ ID NO:14 is substituted and amino acid sequences in which at least one amino acid selected from 4th position Met, 9th position Ser, 10th position Ser, 11th position Leu, 15th position Val, 35th position Tyr, 39th position Pro, 42nd position Ala, 45th position Leu, 46th position Leu, 69th position Asp, 70th position Phe, 71st position Thr, and 82nd position Phe in the amino acid sequence represented by SEQ ID NO:55 is substituted. More preferable human CDR-grafted antibodies include a human CDR-grafted antibody wherein the VH of the antibody comprises an amino acid sequence in which at least one amino acid selected from 1st position Gln, 11th position Val, 42nd position Gly, 75th position Ser, 77th position Asn, 84th position Asn, 93rd position Val, 97th position Ala, and 98th position Arg in the amino acid sequence represented by SEQ ID NO:11 is substituted and wherein the VL of the antibody comprises an amino acid sequence in which at least one amino acid selected from 4th position Met, 9th position Asp, 10th position Ser, 11th position Leu, 15th position Leu, 22th position Asn, 35th position Tyr, 39th position Pro, 42nd position Pro, 45th position Leu, 46th position Leu, 69th position Asp, 70th position Phe, 71st position Thr, 82nd position Val, and 84th position Val in the amino acid sequence represented by SEQ ID NO:14 is substituted; and a human CDR-grafted antibody wherein the VH of the antibody comprises an amino acid sequence in which at least one amino acid selected from 1st position Gln, 11th position Val, 42nd position Gly, 75th position Ser, 77th position Asn, 84th position Asn, 93rd position Val, 97th position Ala, and 98th position Arg in the amino acid sequence represented by SEQ ID NO:11 is substituted and wherein the VL of the antibody comprises an amino acid sequence in which at least one amino acid selected from 4th position Met, 9th position Ser, 10th position Ser, 11th position Leu, 15th position Val, 35th position Tyr, 39th position Pro, 42nd position Ala, 45th position Leu, 46th position Leu, 69th position Asp, 70th position Phe, 71st position Thr, and 82nd position Phe in the amino acid sequence represented by SEQ ID NO:55 is substituted; a human CDR-grafted antibody wherein the VH of the antibody comprises an amino acid sequence in which at least one amino acid selected from 49th position Ser, 77th position Asn, 84th position Asn, 93rd position Val, 97th position Ala, and 98th position Arg in the amino acid sequence represented by SEQ ID NO:54 is substituted and wherein the VL of the antibody comprises an amino acid sequence in which at least one amino acid selected from 4th position Met, 9th position Asp, 10th position Ser, 11th position Leu, 15th position Leu, 22th position Asn, 35th position Tyr, 39th position Pro, 42th position Pro, 45th position Leu, 46th position Leu, 69th position Asp, 70th position Phe, 71st position Thr, 82nd position Val, and 84th position Val in the amino acid sequence represented by SEQ ID NO:14 is substituted; and a human CDR-grafted antibody wherein the VH of the antibody comprises an amino acid sequence in which at least one amino acid selected from 49th position Ser, 77th position Asn, 84th position Asn, 93rd position Val, 97th position Ala, and 98th position Arg in the amino acid sequence represented by SEQ ID NO:54 is substituted and wherein the VL of the antibody comprises an amino acid sequence in which at least one amino acid selected from 4th position Met, 9th position Ser, 10th position Ser, 11th position Leu, 15th position Val, 35th position Tyr, 39th position Pro, 42nd position Ala, 45th position Leu, 46th position Leu, 69th position Asp, 70th position Phe, 71st position Thr, and 82nd position Phe in the amino acid sequence represented by SEQ ID NO:55 is substituted.

Specifically, preferable human CDR-grafted antibody includes a human CDR-grafted antibody wherein the VH of the antibody comprises an amino acid sequence represented by SEQ ID NO:26; a human CDR-grafted antibody wherein the VL of the antibody comprises an amino acid sequence represented by SEQ ID NO:27, an amino acid sequence represented by SEQ ID NO:28 or an amino acid sequence represented by SEQ ID NO:29; a human CDR-grafted antibody wherein the VH of the antibody comprises an amino acid sequence represented by SEQ ID NO:26 and wherein the VL of the antibody comprise an amino acid sequence represented by SEQ ID NO:27; a human CDR-grafted antibody wherein the VH of the antibody comprises an amino acid sequence represented by SEQ ID NO:26 and wherein the VL of the antibody comprises an amino acid sequence represented by SEQ ID NO:28; and a human CDR-grafted antibody wherein the VH of the antibody comprises an amino acid sequence represented by SEQ ID NO:26 and wherein the VL of the antibody comprises an amino acid sequence represented by SEQ ID NO:29.

The human antibody includes human antibodies produced by hybridomas prepared from transgenic non-human animals, human antibodies prepared into monoclones using genetic engineering techniques or the like.

Essentially, although the human antibody represents an antibody naturally existed in human bodies, it also includes antibodies obtained from a human antibody phage library and a human antibody-producing transgenic animal prepared based on the recent advance in the genetic engineering, cell engineering and embryo engineering techniques.

The human antibody of the present invention includes any human antibodies so long as it can specifically bind to hIGF-I and hIGF-II to inhibit the functions of hIGF-I and hIGF-II. Specifically, the human antibody includes human antibodies produced by a human antibody-producing cell prepared using genetic engineering techniques or cell engineering techniques, or monoclonal antibodies obtained from human antibody-producing transgenic non-human animals using general hybridoma preparation methods.

The method for preparing human antibody-producing cells using genetic engineering techniques include a method, for example, which comprises constructing human anibody phage library which expresses Fab (fragment of antigen binding) or single-chain antibody on the surface of the phage by inserting antibody genes prepared from human B cell into phage genes, and recovering a phage which expresses antibody fragment with a aimed antigen-binding activity using the binding activity thereof to a substrate with an antigen immobilized thereon as a marker. Said antibody fragments can be further converted into a human antibody molecule comprising two complete H chains and two complete L chains using protein engineering techniques.

The method for preparing human antibody-producing cells using cell engineering techniques includes, for example, a step of isolating human peripheral lymphocytes, a step of infecting EB virus and the like to the lymphocytes to immortalize, and a step of isolating lymphocyte which is capable of producing the antibody and capable of being subcultured after cloning by limited dilution method. The method also includes a process of culturing the lymphocyte and purifying an aimed antibody in the culture to obtain the antibody.

In the case of the CDRs of antibody selected from antibody gene library prepared artificially are linked with the FR of an appropriate human antibody, and further linked with CH of a human antibody, the artificial antibody gene library includes antibody gene libraries prepared from a antibody-producing cell population, antibody gene libraries allowed to be increased the repertoire by introducing random mutations into the antibody gene libraries.

The antibody fragment of the present invention includes an active antibody fragment or the like which comprises a part or the whole of the variable region of the aforementioned antibody, and specifically binds to hIGF-I and hIGF-II to inhibit the functions of hIGF-I and hIGF-II. The antibody fragment includes Fab, F(ab')$_2$, Fab', scFv, diabody, dsFv, CDR-containing peptide and the like described below.

Fab is an antibody fragment having a molecular weight of about 50,000 and exhibiting an antigen-binding activity where about one half of N-terminal side of H chain and the full length of L chain, among fragments obtained by treating IgG-type antibody molecule with a protease, papain (cleave an amino acid residue at position 224 of an H chain) are bound together through a disulfide bond.

The Fab of the present invention can be obtained by treating an antibody which specifically binds to hIGF-I and hIGF-II to inhibit the functions of hIGF-I and hIGF-II with a protease papain. Alternatively, Fab can be produced by inserting DNA encoding the Fab of the antibody into an expression vector for prokaryote or an expression vector for eukaryote, and introducing the vector into a prokaryote or a eukaryote to be expressed.

F(ab')$_2$ is an antibody fragment having a molecular weight of about 100,000 and exhibiting an antigen-binding activity which is slightly larger than the Fab bound via disulfide bond of the hinge region, among fragments obtained by treating IgG-type antibody molecule with a protease, pepsin.

The F(ab')$_2$ of the present invention can be obtained by treating an antibody which specifically binds to hIGF-I and hIGF-II to inhibit the functions of hIGF-I and hIGF-II with a protease pepsin. Alternatively, the F(ab')$_2$ can be prepared by linking the following Fab' via thioether bound or disulfide bound.

Fab' is an antibody fragment with a molecular weight of about 50,000 and having an antigen binding activity, as obtained by cleaving the disulfide bound in the hinge region of the aforementioned F(ab')$_2$.

The Fab' of the present invention can be obtained by treating the F(ab')$_2$ which specifically binds to hIGF-I and hIGF-II to inhibit the functions of hIGF-I and hIGF-II with a reducing agent, dithiothreitol. Alternatively, Fab' can be produced by inserting DNA encoding the Fab' antibody fragment into an expression vector for prokaryote or an expression vector for eukaryote, and introducing the vector into a prokaryote or a eukaryote to be expressed.

scFv is an antibody fragment having an antigen binding activity and is an VH-P-VL or an VL-P-VH polypeptide where one VH and one VL are linked using an appropriate peptide linker (hereinafter referred to as P).

The scFv of the present invention can be produced by obtaining cDNAs encoding the VH and VL of an antibody which specifically binds to hIGF-I and hIGF-II to inhibit the functions of hIGF-I and hIGF-II, constructing DNA encoding scFv, inserting the DNA into an expression vector for prokaryote or an expression vector for eukaryote, and introducing the vector into a prokaryote or a eukaryote to be expressed.

Diabody is an antibody fragment where svFv is dimerized and is an antibody fragment having divalent antigen binding activity. The divalent antigen binding activity may be the same or one of them can be used as a different antigen binding activity.

The diabody of the present invention can be produced by preparing cDNAs encoding the VH and VL of an antibody which specifically binds to hIGF-I and hIGF-II to inhibit the functions of hIGF-I and hIGF-II, constructing DNA encoding scFv in such a manner that the amino acid sequence of P comprises eight residues or less, inserting the DNA into an expression vector for prokaryote or an expression vector for eukaryote, and introducing the vector into a prokaryote or a eukaryote to be expressed.

The dsFv is an antibody fragment where a polypeptide in which each one amino acid residue in VH and VL is substituted with a cysteine residue is linked via a disulfide bond between the cysteine residues. The amino acid residue to be substituted with a cysteine residue can be selected based on a three-dimensional structure estimation of the antibody according to a method shown by Reiter, et al. (*Protein Engineering*, 7, 697-704, 1994).

The dsFv of the present invention can be produced by preparing cDNAs encoding the VH and VL of the antibody which specifically binds to hIGF-I and hIGF-II to inhibit the functions of hIGF-I and hIGF-II, constructing DNA encoding dsFv, inserting the DNA into an expression vector for prokaryote or an expression vector for eukaryote, and introducing the vector into a prokaryote or a eukaryote to be expressed.

A CDR-containing peptide is constituted by comprising at least one region of CDRs of VH or VL. A peptide comprising plural CDRs can be linked either directly or via an appropriate peptide linker.

The CDR-containing peptide of the present invention can be produced by constructing DNA encoding the CDRs of the VH and VL of an antibody which specifically binds to hIGF-I and hIGF-II to inhibit the functions of hIGF-I and hIGF-II, inserting the DNA into an expression vector for prokaryote or an expression vector for eukaryote, and introducing the vector into a prokaryote or a eukaryote to be expressed.

The CDR-containing peptide can also be prepared by a chemical synthetic method such as an Fmoc method (fluorenylmethyloxycarbonyl method) and a tBoc method (tert-butyloxycarbonyl method)

The antibody of the present invention includes antibody conjugates prepared by conjugating a radioisotope, an agent having low-molecular weight, an agent having high-molecular weight, a protein, and the like to the antibody or the antibody fragment thereof of the present invention, by genetic engineering techniques or chemically.

The antibody conjugate of the present invention conjugated by a genetic engineering techniques can be produced by ligating the DNA encoding the antibody and the antibody fragment which specifically binds to hIGF-I and hIGF-II to inhibit the functions of hIGF-I and hIGF-II with the DNA encoding an aimed protein to be conjugated and inserting into an expression vector, and then introducing the expression vector into an appropriate host cell to be expressed.

The antibody conjugate of the present invention conjugated chemically can be produced by conjugating a radioisotope, an agent having low-molecular weight, an agent having high-molecular weight and a protein and the like with N-terminal or C-terminal of the H chain or L chain of the antibody and the antibody fragment which specifically binds to hIGF-I and hIGF-II to inhibit the functions of hIGF-I and hIGF-II, an appropriate substituent group or side chain of the antibody and antibody fragments or a sugar chain in the antibody and antibody fragments, by chemical techniques (Introduction to Antibody Engineering, written by O. Kanemitsu, published by Chijin Shokan, 1994).

The radioisotope includes, for example, $^{131}$I, and $^{125}$I and can be conjugated with the antibody for example by the chloramine T method.

The agent having low-molecular weight includes anti-cancer agents including an alkylating agent such as nitrogen mustard and cyclophosphamide; a metabolism antagonist such as 5-fluorouracil and methotrexate; an antibiotic such as daunomycin, bleomycin, mitomycin C, daunorubicin and doxorubicin; a plant alkaloid such as vincristine, vinblastine and vindesine; and a hormone agent such as tamoxifen and dexamethasone ("Clinical Oncology" edited by Japan Clinical Tumor Study Team, published by Gan to Kagaku Ryohosha, 1996); a steroidal agent such as hydrocortisone and prednisone; a non-steroidal agent such as aspirin and indomethacin; an immunomodulator such as gold thiomalate and penicillamine; an immunosuppressant such as cyclophosphamide and azathioprine; an anti-inflammatory agent including antihistamine agent such as chlorpheniramine maleate and clemastine ("Inflammation and Anti-inflamatory Therapy", published by Ishiyaku Publishers, Inc., 1982) or the like. Examples of a method for conjugating daunomycin with an antibody are a method where daunomycin and amino group of the antibody are linked via glutaraldehyde, a method where an amino group of daunomycin and carboxyl group of the antibody are linked via a water-soluble carbodiimide and the like.

The agant having high molecular weight includes polyethylene glycol (hereinafter mentioned as PEG), albumin, dextran, polyoxyethylene, styrene-maleic acid copolymer, polyvinylpyrrolidone, pyran copolymer, hydroxypropyl methacrylamide and the like. When such a compound having high-molecular weight is conjugated with an antibody or antibody fragment, an effect such as (1) enhancement of stability against various chemical, physical or biological factors, (2) significant extension of blood half-life and (3) disappearance of immunogenicity and suppression of antibody production can be expected ("Bioconjugate Drugs", published by Hirokawa Shoten, 1993). An example of a method for conjugating PEG with an antibody includes a method which reacts with a PEG-modifying reagent ("Bioconjugate Drugs", published by Hirokawa Shoten, 1993). Examples of the PEG-modifying reagent include a modifier for ϵ-amino group of lysine (Japanese Published Unexamined Application No. 178926/86), a modifier for carboxyl groups of aspartic acid and glutamic acid (Japanese Published Examined Application No. 23587/81), a modifier for guanidine group of arginine (Japanese Published Unexamined Application No. 117920/90), and the like.

Examples of the protein include cytokines which activate the immunocompetent cells such as human interleukin 2, human granulocyte macrophage colony stimulating factor, human macrophage colony stimulating factor, human interleukin 12 and the like. Toxin such as diphtheria toxin and ricin having an activity of directly damaging the cancer cells can also be used. With regard to a conjugate in which protein is conjugated with an antibody, the conjugate can be produced in such a manner that, for example, cDNA encoding protein is ligated with cDNA encoding antibody or antibody fragment to construct a DNA which encodes the complex, the DNA is inserted into expression vector for prokaryote or eukaryote and the expression vector is introduced into the prokaryote or the eukaryote to express whereupon the conjugate is produced.

The methods for preparing a human chimeric antibody and a human CDR-grafted antibody which specifically binds to hIGF-I and hIGF-II to inhibit the functions of hIGF-I and hIGF-II, methods for preparing an antibody fragment thereof, and a method for measuring the activity thereof are described hereinbelow, along with a method for using the humanized antibody and the antibody fragment of the present invention.

1. Preparation of Humanized Antibody (1) Construction of Vector for Expression of Humanized Antibody As a vector for expression of humanized antibody, a vector for expressing an antibody where a gene encoding the CH and/or CL of a human antibody is inserted can be constructed by cloning genes, respectively, encoding the CH and CL of a human antibody into an expression vector for animal cells.

The C region of a human antibody can be CH and CL of an optional human antibody, and its examples include a C region of IgG1 subclass of human antibody H chain (hereinafter referred to as hCγ1), a C region of κ class of human antibody L chain (hereinafter referred to as hCκ) and the like. As the genes encoding CH and CL of a human antibody, a chromosomal DNA comprising exons and introns can be used, and cDNAs can also be used.

As the expression vector for animal cells, any expression vector for animal cells can be used so long as the expression vector can introduce and express of genes encoding the C region of a human antibody. For example, pAGE107 (Cytotechnology, 3, 133, 1990), pAGE103 (Journal of Biochemistry, 101, 1307, 1987), pHSG274 (Gene, 27, 223, 1984), pKCR (Proceedings of the National Academy of Sciences of the United States of America, 78, 1527, 1981), and pSG1βd2-4 (Cytotechnology, 4, 173, 1990) can be exemplified. As the promoter and enhancer to be used in the expression vector for animal cells, SV40 early promoter and enhancer (Journal of Biochemistry, 101, 1307, 1987), LTR promoter and enhancer of Moloney mouse leukemia virus (Biochemical & Biophysical Research Communications, 149, 960, 1987), and the promoter (Cell, 41, 479, 1985) and enhancer (Cell, 33, 717, 1983) of immunoglobulin H chain can be exemplified.

As the vector for expression of humanized antibody, either of a vector type in which the antibody H chain and L chain are present in different vectors or a vector type in which the H chain and L chain thereof are present in the same vector (hereinafter referred to as tandem-type) can be used, a tandem-type vector for expression of humanized antibody is preferable in view of easiness for construction of the vector for expression of humanized antibody, easiness for introduction thereof into animal cells and easiness for equality of the amount of the expressed antibody H chain and L chain in animal cells (Journal of Immunological Methods, 167, 271, 1994). The tandem-type vector for expression of humanized antibody includes pKANTEX93 (WO 97/10354), pEE18 (Hybridoma, 17, 559, 1998) and the like.

The constructed vector for expression of humanized antibody can be used for expressing human chimeric antibodies and human CDR-grafted antibodies in animal cells.

(2) Preparation of cDNAs Encoding the V Region of an Antibody of a Non-Human Animal and the Analysis of the Amino Acid Sequence cDNAs encoding the VH and VL of an antibody of a non-human animal, such as a mouse antibody are obtained in the following manner.

mRNA is extracted from a hybridoma producing a murine antibody or the like, and then cDNAs are synthesized. The synthesized cDNAs are cloned into a vector such as a phage, plasmid or the like, to prepare a cDNA library. Using the C region or the V region of the mouse antibody as probe, a recombinant phage or recombinant plasmid having the cDNA encoding the VH or a recombinant phage or recombinant plasmid having the cDNA encoding the VL is isolated from the library, respectively. The full-length nucleotide sequences of the aimed VH and VL of the mouse antibody in the recombinant phage or recombinant plasmid are determined, to deduce the full length of the amino acid sequences of the VH and VL from the nucleotide sequences.

As a non-human animal, any of animals capable of preparing hybridoma, such as mouse, rat, hamster, and rabbit can be used.

An example of a method for preparing the total RNA from hybridoma is a guanidine thiocyanate-cesium trifluoroacetate method (Methods in Enzymology, 154, 3, 1987) and an example of a method for preparing mRNA from the total RNA is an oligo (dT) immobilized cellulose column method (Molecular Cloning: A Laboratory Manual, Cold Spring Harbor Lab. Press, New York, 1989). Examples of a kit for the preparing mRNA from hybridoma are Fast Track mRNA Isolation Kit (manufactured by Invitrogen), Quick Prep mRNA Purification Kit (manufactured by Amersham-Pharmacia), and the like.

Examples of a method for the synthesizing of cDNA and for preparing cDNA library are a conventional method (Molecular Cloning: A Laboratory Manual, Cold Spring Harbor Lab. Press, New York, 1989; Current Protocols in Molecular Biology, Supplement 1-34) or a method using a commercially available kit such as Super Script™ Plasmid System for cDNA Synthesis and Plasmid Cloning (manufacture by Gibco BRL), ZAP-cDNA Synthesis Kit (manufactured by Stratagene), Timesaver cDNA Synthesis Kit (manufactured by Amersham-Pharmacia).

With regard to vector into which cDNA synthesized using mRNA extracted from the hybridoma as a template is inserted while preparing the cDNA library, any vector may be used so long as the cDNA can be inserted therein. For example, phage or plasmid vector such as ZAP Express (Strategies, 5, 58, 1992), pBluescript II SK(+) (Nucleic Acid Research, 17, 9494, 1989), λ ZAP II (manufactured by Stratagene), λ gt 10 and λ gt 11 (DNA Cloning: A Practical Approach, I, 49, 1985), Lambda BlueMid (manufactured by Clontech), λ ExCell, pT7T3 18U (manufactured by Amersham-Pharmacia), pcD2 (Molecular & Cellular Biology, 3, 280, 1983) and pUC 18 (Gene, 33, 103, 1985) may be used.

With regard to *Escherichia coli* into which a cDNA library constructed by phage or plasmid vector is introduced, any *Escherichia coli* may be used so long as it the cDNA library can be inserted, expressed and maintained. Its examples are XL1-Blue MRF' (Journal of Biotechnology, 23, 271, 1992), C600 (Genetics, 59, 177, 1968), Y1088 and Y1090 (Science, 222, 778, 1983), NM 522 (Journal of Molecular Biology, 166, 1, 1983), K 802 (Journal of Molecular Biology, 16, 118, 1966), JM 105 (Gene, 38, 275, 1985) and the like.

With regard to a method for selecting cDNA clones encoding VH and VL of antibody of non-human animal from cDNA library, it can be selected by a colony hybridization method or a plaque hybridization method (Molecular Cloning: A Laboratory Manual, Cold Spring Harbor Lab. Press, New York, 1989) using radioisotope or fluorescence-labeled probe. In addition, cDNAs encoding VH and VL can be prepared by a polymerase chain reaction (hereinafter, referred to as PCR method; Molecular Cloning: A Laboratory Manual, Cold Spring Harbor Lab. Press, New York, 1989; Current Protocols in Molecular Biology, Supplement 1-34) by preparing primer and cDNA synthesized from mRNA or cDNA library as a template.

cDNA selected by the above-mentioned method is cleaved by an appropriate restriction enzyme or the like, cloned to a plasmid vector such as pBluescript SK(−) (manufactured by Stratagene), subjected to a method conventionally used for analysis of nucleotide sequence such as a dideoxy method (Proceedings of the National Academy of Sciences of the United States of America, 74, 5463, 1977) and analyzed by an automatic sequencer ABI PRISM 377 (manufactured by ABI) or the like whereupon a nucleotide sequence of the cDNA can be determined.

The full length of amino acid sequences of VH and VL are deduced from the determined nucleotide sequences and compared with the full length of amino acid sequences of VH and VL of known antibody (Sequences of Proteins of Immunological Interest, U.S. Dept. Health and Human Services, 1991) whereupon it can be confirmed whether the obtained cDNA encodes the full length of amino acid sequences of VH or VL of the antibody containing a signal sequence for secretion. With regard to the full length of amino acid sequences of VH or VL of the antibody containing a signal sequence for secretion, length and N-terminal amino acid sequence of the signal sequence can be deduced by comparing with the full length of amino acid sequences of VH and VL of the known antibody (Sequences of Proteins of Immunological Interest, U.S. Dept. Health and Human Services, 1991) and, further, subclass to which they belong can be determined. Also an amino acid sequence of each CDR of VH and VL can be found by comparing with the amino acid sequences of VH and VL of the known antibody (Sequences of Proteins of Immunological Interest, U.S. Dept. Health and Human Services, 1991).

A homology search of sequences such as a BLAST method (Journal of Molecular Biology, 215, 403, 1990) to any database such as SWISS-PROT or PIR-Protein can be conducted using the full length of amino acid sequences of VH and VL to examine novelty of the sequence.

(3) Construction of Human Chimeric Antibody Expression Vector cDNAs encoding VH and VL of antibody of non-human animal are cloned to the upstream of genes encoding CH and CL of human antibody of vector for expression of humanized antibody mentioned in the above 2(1) to thereby construct human chimeric antibody expression vector. For example, each cDNA encoding VH and VL of antibody of non-human animal is ligated to synthetic DNA comprising a nucleotide sequence of 3'-terminal of VH and VL of antibody of non-human animal and a nucleotide sequence of 5'-terminal of CH and CL of human antibody and having recognition sequence of an appropriate restriction enzyme at both ends, and cloned so that each of them is expressed in an appropriate form on the upstream of gene encoding CH and CL of human antibody of the vector for expression of humanized antibody mentioned in the above 2(1) to construct human chimeric antibody expression vector. In addition, cDNA encoding VH and VL is amplified by a PCR method using a primer having a recognition sequence of an appropriate restriction enzyme at 5'-terminal using a plasmid containing cDNA encoding VH and VL of antibody of non-human animal and each of them is cloned so that it is expressed in an appropriate form at the upstream of gene encoding CH and CL of human antibody of the vector for expression of humanized antibody mentioned in the above 2(1) to construct human chimeric antibody expression vector.

(4) Construction of cDNA Encoding V Region of Human CDR-Grafted Antibody cDNAs encoding VH and VL of human CDR-grafted antibody can be constructed as follows. Firstly, amino acid sequence of FRs in VH and VL of human antibody to which desired amino acid sequences of CDRs in VH and VL of non-human animal is selected. With regard to the amino acid sequence of FRs in VH and VL of human antibody, any amino acid sequence of FRs in VH and VL of human antibody may be used so long as it is derived from human antibody. Examples thereof are amino acid sequences of FRs in VH and VL of human antibody registered in database such as Protein Data Bank and a consensus amino acid sequence of each subgroup of FRs in VH and VL of human antibody (Sequences of Proteins of Immunological Interest, U.S. Dept. Health and Human Services, 1991). In order to prepare a human CDR-grafted antibody having a sufficient activity, an amino acid sequence having a homology of as high as possible (60% or more) to the amino acid sequence of FRs in VH and VL of antibody of desired non-human animal among the above is preferably selected. After that, the amino acid sequence of CDRs in VH and VL of desired non-human animal antibody is grafted to the selected amino acid sequence of FRs in VH and VL of the human antibody to design the amino acid sequences of VH and VL of the human CDR-grafted antibody. The designed amino acid sequences are converted to nucleotide sequences by considering the frequency of codon usage (Sequences of Proteins of Immunological Interest, U.S. Dept. Health and Human Services, 1991) found in the nucleotide sequence of gene of antibody whereupon nucleotide sequences encoding amino acid sequences of VH and VL of the human CDR-grafted antibody are designed. Based on the designed nucleotide sequences, several synthetic DNAs having a length of about 100 bases are synthesized and a PCR method is carried out by using them. In this case, it is preferred to design at least 4 to 6 synthetic DNAs for both VH and VL in view of reaction efficiency in the PCR and length of synthesizable DNA.

Further, by introducing a recognition sequence of an appropriate restriction enzyme into 5'-terminal of synthetic DNAs located at both ends, cloning to a vector for expression of humanized antibody constructed in the above 2(1) can be carried out. After the PCR, the amplified product is cloned to a plasmid such as pBluescript SK(−) (manufactured by Stratagene) and a nucleotide sequence is determined by the method mentioned in the above 2(2) whereupon a plasmid having nucleotide sequences encoding the amino acid sequences of VH and VL of the desired human CDR-grafted antibody is obtained.

(5) Modification of Amino Acid Sequence of V Region of Human CDR-Garafted Antibody It has been known that, when a human CDR-garafted antibody id produced by simply grafting the aimed CDRs in VH and VL of an antibody of the non-human animal into FRs in VH and VL of human antibody, antigen-binding antibody of human CDR-grafted antibody lowers as compared with the original antibody of the non-human animal (Bio/Technology, 9, 266, 1991). With regard to the cause thereof, it is considered that, in the original VH and VL of antibody of the non-human animal, not only CDRs but also various amino acid residues of FRs participate in antigen-binding activity either directly or indirectly and that, as a result of grafting of CDRs, such amino acid residues change to amino acid residues being different from FRs in VH and VL of the human antibody. In order to solve the problem, it has been conducted in a human CDR-grafted antibody that, among the amino acid sequence of FRs in VH and VL of human antibody, an amino acid residue which directory relates to binding to the antigen, or amino acid residue which indirectly relates to binding to an antigen by interacting with an amino acid residue in CDRs or by maintaining the three-dimensional structure of an antibody, is identified and that the amino acid residue found in the original antibody of non-human animal is modified to thereby increase the lowered antigen-binding activity (Bio/Technology, 9, 266, 1991). In the preparation of human CDR-grafted antibody, how to efficiently identify the amino acid residues of relating to the antigen binding activity in FR is most important, so that the three dimensional structure of an antibody is constructed and analyzed by X-ray crystallography (Journal of Molecular Biology, 112, 535, 1977), a computer-modeling (Protein Engineering, 7, 1501, 1994), or the like. Information for three-dimensional structure of the antibody as such has given much advantageous information to the preparation of human CDR-grafted antibody but, on the other hand, no method for the preparing of human CDR-grafted antibody which is applicable to any antibodies has not been established yet and, at present, various trials and errors are necessary such as that several kinds of modified products are prepared for each antibody and that correlation to each antigen bonding activity is investigated.

Modification of amino acid residue of FRs in VH and VL of human antibody can be achieved by conducting a PCR method mentioned in the above 2(4) using a synthetic DNA for the modification. With regard to the amplified product after the PCR, its nucleotide sequence is determined by the method mentioned in the above 2(2) whereby it is confirmed that the desired modification has been done.

(6) Construction of Human CDR-Grafted Antibody Expression Vector cDNAs encoding VH and VL of the human CDR-grafted antibody constructed in the above 2(4) and (5) are cloned to the upstream of genes encoding CH and CL of the human antibody in the vector for expression of the humanized antibody mentioned in the above 2(1) to thereby construct a human CDR-grafted antibody expression vector.

For example, in the synthetic DNA used for the construction of VH and VL of the human CDR-grafted antibody in the above 2(4) and (5), recognition sequences of an appropriate restriction enzyme are introduced into 5'-terminal of the synthetic DNAs located at both ends whereby they can be cloned to the upstream of genes encoding CH and CL of human antibody in the vector for expression of humanized antibody mentioned in the above 2(1) in such a manner that they are expressed in an appropriate form.

(7) A Transient Expression of Humanized Antibody

In order to efficiently evaluate the antigen-binding activity of the various humanized antibodies prepared, a transient expression of humanized antibody can be conducted using the humanized antibody expression vector mentioned in the above 2(3) and (6) or the modified expression vector thereof. With regard to a host cell into which the expression vector is introduced, any cell may be used so long as it is a host cell which can express the humanized antibody, but COS-7 cell (ATCC CRL-1651) has been commonly used in view of its high expressing amount (Methods in Nucleic Acids Research, CRC Press, 283, 1991). The methods for the introducing the expression vector into COS-7 cells are DEAE-dextran method (Methods in Nucleic Acids Research, CRC Press, 283, 1991), a lipofection method (Proceedings of the National Academy of Sciences of the United States of America, 84, 7413, 1987), and the like. After introducing the expression vector, the amount of humanized antibody expressed in the culture supernatant and antigen-binding activity can be measured by, for example, ELISA (Antibodies: A Laboratory Manual, Cold Spring Harbor Laboratory, Chapter 14, 1988; Monoclonal Antibodies: Principles and Practice, Academic Press Limited, 1996).

(8) Stable Expression of Humanized Antibody

A transformant cell which stably expresses humanized antibody can be obtained by introducing the humanized antibody expression vector mentioned in the above 2(3) and (6) into appropriate host cell.

The methods for the introducing expression vector into host cell are an electroporation method (Cytotechnology, 3, 133, 1990), and the like.

With regard to the host cell into which humanized antibody expression vector is introduced, any cell may be used so long as it is a host cell which can express the humanized antibody. Examples thereof are mouse SP2/0-Ag14 cell (ATCC CRL-1581), mouse P3X63-Ag8.653 cell (ATCC CRL-1580), dihydrofolate reductase gene (hereinafter referred to as dhfr)-deficient CHO cell (Proceedings of the National Academy of Sciences of the United States of America, 77, 4216, 1980) and rat YB2/3HL.P2.G11.16Ag.20 cell (ATCC CRL-1662; hereinafter referred to as YB2/0 cell).

A transformant in which humanized antibody is stably expressed after introducing expression vector can be selected by culturing in a medium for animal cell culture containing an agent such as G418 sulfate (hereinafter, referred to as G418) according to a process disclosed in Japanese Published Unexamined Patent Application NO. 257891/90. With regard to a medium for incubation of animal cell culture, RPMI 1640 medium (manufactured by Nissui Seiyaku), GIT medium (manufactured by Nippon Seiyaku), EX-CELL 302 medium (manufactured by JRH), IMDM (manufactured by Gibco BRL), Hybridoma-SFM (manufactured by Gibco BRL), a medium obtained by adding various additives such as FBS, and the like may be used. When the resulting transformant cell is cultured in a medium, humanized antibody can be expressed and accumulated in the culture supernatant. The amount of the humanized antibody expressed in the culture supernatant and antigen-binding activity can be measured by ELISA. Further, in the transformant cell, the amount of the humanized antibody expressed can be increased by utilizing a dhfr system or the like according to a method disclosed in Japanese Published Unexamined Patent Application NO. 257891/90.

Humanized antibody can be purified from the culture supernatant of the transformant cell using a protein A column (Antibodies: A Laboratory Manual, Cold Spring Harbor Laboratory, Chapter 8, 1988; Monoclonal Antibodies: Principles and Practice, Academic Press Limited, 1996). Besides that, purifying methods which are usually used for purification of proteins can be used. For example, gel filtration, ion-exchange chromatography and ultrafiltration may be conducted in combination so as to purify. Molecular weight of H chain and L chain of the purified humanized antibody or of the whole antibody molecular can be determined by a polyacrylamide gel electrophoresis (hereinafter referred to as PAGE; Nature, 227, 680, 1970), a western blotting method (Antibodies: A Laboratory Manual, Cold Spring Harbor Laboratory, Chapter 12, 1988; Monoclonal Antibodies: Principles and Practice, Academic Press Limited, 1996), and the like.

2. Preparation of Antibody Fragments

Antibody fragment can be prepared by genetic engineering techniques or protein chemical techniques based on the anti-hIGF antibody mentioned in the above 1.

Examples of the genetic engineering techniques are a method where gene encoding desired antibody fragment is constructed and expression and purification are conducted using a suitable host such as animal cells, plant cells, insect cells, *Escherichia coli*, or the like.

Examples of the protein chemical techniques are a method of site-specific cleavage, purification using a protease such as pepsin and papain, and the like.

As antibody fragment, process for producing of Fab, F(ab')$_2$, Fab', scFv, diabody, dsFv or CDR-containing peptide as will be specifically illustrated as follows.

(1) Preparation of Fab

Fab can be prepared by treating IgG with protease, papain by using protein chemical techniques. After the treatment with papain, it is possible to recover as a uniform Fab by passing through a protein A column to separate from IgG molecule and Fc fragment provided that the original antibody is an IgG subclass having a binding property to protein A (Monoclonal Antibodies: Principles and Practice, third edition, 1995). In the case of an antibody of an IgG subclass having no binding property to protein A, Fab can be recovered by an ion-exchange chromatography at a fraction eluted by a low salt concentration (Monoclonal Antibodies: Principles and Practice, third edition, 1995). Fab can also be prepared by genetic engineering techniques, and using *E. coli* in many cases or using insect cells, animal cells, and the like. For example, DNA encoding V region of the antibody mentioned in the above 2(2), 2(4) and 2(5) is cloned to a vector for expression of Fab whereupon Fab expression vector can be prepared. With regard to vector for expression of Fab, any vector may be used so long as DNA for Fab can be inserted and expressed. An example thereof is pIT 106 (Science, 240, 1041, 1988). Fab expression vector is introduced into an appropriate *E. coli* whereby Fab can be formed and accumulated in an inclusion body or a periplasmic space. From the inclusion body, active Fab can be obtained by a refolding method generally used for proteins and, when expressed in the periplasmic space, active Fab leaks out in a culture supernatant.

After the refolding or from the culture supernatant, a uniform Fab can be purified using a column to which antigen is bound (Antibody Engineering, A Practical Guide, W. H. Freeman and Company, 1992).

(2) Preparation of F(ab')$_2$

F(ab')$_2$ can be prepared by treating of IgG with protease, pepsin by using protein chemical techniques. After the treatment with pepsin, it can be recovered as a uniform F(ab')$_2$ by the same purifying operation as in the case of Fab (Monoclonal Antibodies: Principles and Practice, third edition, Academic Press, 1995). It can also be prepared by a method where Fab' mentioned in the following 2(3) is treated with a maleimide such as o-PDM or bismaleimide to form a thioether bond or by a method where it is treated with DTNB [5,5'-dithiobis(2-nitrobenzoic acid)] to form an S—S bond (Antibody Engineering, A Practical Approach, IRL Press, 1996).

(3) Preparation of Fab'

Fab' can be prepared by treating F(ab')$_2$ mentioned in the above 2(2) with a reducing agent such as dithiothreitol. Fab' can be prepared by genetic engineering techniques using *E. coli* in many cases or using insect cells, animal cells, and the like. For example, DNA encoding V region of the antibody mentioned in the above 2(2), 2(4) and 2(5) is cloned to a vector for expression of Fab' whereupon Fab' expression vector can be prepared. With regard to a vector for expression of Fab', any vector may be used so long as DNA for Fab' can be inserted and expressed. Fab' can be formed and accumulated in an inclusion body or a periplasmic space by introducing the Fab' expression vector into an appropriate *E. coli*. From the inclusion body, active Fab' can be obtained by a refolding method which is usually used in proteins and, when the Fab' is expressed in the periplasmic space, it can be recovered extracellulary by disrupting the cell with treating such as partial digestion by lysozyme, osmotic shock and sonication. After the refolding or from the disrupted cell solution, a uniform Fab' can be purified using a protein G column or the like (Antibody Engineering, A Practical Approach, IRL Press, 1996).

(4) Preparation of scFv scFv can be prepared using phage or *E. coli* or using insect cells or animal cells by genetic engineering techniques. For example, DNA encoding V region of the antibody mentioned in the above 2(2), 2(4) and 2(5) is cloned to a vector for expression of scFv whereupon an scFv expression vector can be prepared. With regard to the vector for expression of scFv, any vector may be used so long as the DNA of scFv can be inserted and express. Examples thereof are pCANTAB5E (manufactured by Pharmacia), pHFA (Human Antibodies & Hybridomas, 5, 48, 1994), and the like. When scFv expression vector is introduced into an appropriate *E. coli* and a helper phage is infected, to thereby obtain a phage which expresses scFv on the phage surface in a fused form with the surface protein of the phage. Also, scFv can be formed and accumulated in a periplasmic space or an inclusion body of *E. coli* into which scFv expression vector is introduced. From the inclusion body, active scFv can be obtained by a refolding method generally used for proteins and, when scFv is expressed in the periplasmic space, it can be recovered extracellulary by disrupting the cell with treating such as partial digestion by lysozyme, osmotic shock and sonication. After the refolding or from the disrupted cell solution, a uniform scFv can be purified using a cation-exchange chromatography or the like (Antibody Engineering, A Practical Approach, IRL Press, 1996).

(5) Preparation of Diabody

Diabody can be prepared using *E. coli* in many cases or using insect cells, animal cells, and the like by genetic engineering techniques. For example, DNAs in which VH and VL of the antibody mentioned in the above 2(2), 2(4) and 2(5) are linked by a linker coding 8 amino acid residues or less is prepared and cloned into a vector for expression of diabody whereupon a diabody expression vector can be prepared. With regard to a vector for expression of diabody, any vector may be used so long as the DNA of diabody can be inserted and expressed. Examples thereof are pCANTAB 5E (manufactured by Pharmacia) and pHFA (Human Antibodies Hybridomas, 5, 48, 1994). Diabody can be formed and accumulated in a periplasmic space or an inclusion body of *E. coli* into which a diabody expression vector is introduced. From the inclusion body, active diabody can be obtained by a refolding method generally used for proteins and, when the diabody is expressed in the periplasmic space, it can be recovered extracellulary by disrupting the cell with treating such as partial digestion by lysozyme, osmotic shock and sonication. After the refolding or from the disrupted cell solution, a uniform diabody can be purified using a cation-exchange chromatography or the like (Antibody Engineering, A Practical Approach, IRL Press, 1996).

(6) Preparation of dsFv dsFv can be prepared using *E. coli* in many cases or using insect cells, animal cells, and the like by genetic engineering techniques. Firstly, mutation is introduced into an appropriate position of DNA encoding VH and VL of the antibody mentioned in the above 2(2), 2(4) and 2(5) to prepare DNAs in which an encoded amino acid residue is replaced with cysteine. Each DNA prepared as such is cloned to a vector for expression of dsFv whereby an expression vector of VH and VL can be prepared. With regard to a vector for expression of dsFv, any vector may be used so long as the DNA for dsFv can be inserted and expressed. An example thereof is pULI 9 (Protein Engineering, 7, 697, 1994). The expression vector of VH and VL is introduced into an appropriate *E. coli* and dsFv is formed and accumulated in an inclusion body or a periplasmic space. VH and VL are obtained from the inclusion body or the periplasmic space, mixed and subjected to a refolding method generally used for proteins to thereby obtain active dsFv. After the refolding, it can be further purified by an ion-exchange chromatography, a gel filtration, and the like (Protein Engineering, 7, 697, 1994).

(7) Preparation of CDR-Containing Peptide

CDR-containing peptide can be prepared by a chemical synthesis method such as an Fmoc method or a tBoc method. Further, DNA encoding a CDR-containing peptide is prepared and the resulting DNA is cloned to an appropriate vector for expression whereby a CDR-containing peptide expression vector can be prepared. With regard to a vector for expression, anything may be used so long as it can insert and express the DNA which encodes CDR-containing peptide. Examples thereof are pLEX (manufactured by Invitrogen) and pAX4a+ (manufactured by Invitrogen). The expression vector is introduced into an appropriate *E. coli* and formed and accumulated in an inclusion body or a periplasmic space. From the inclusion body or the periplasmic space, CDR-containing peptide is prepared and can be purified by an ion-exchange chromatography and a gel filtration (Protein Engineering, 7, 697, 1994).

3. Method for Evaluating the Activity of Humanized Antibody or Antibody Fragment Thereof The binding activity of an anti-hIGF humanized antibody to hIGF in a culture supernatant or the binding activity of the purified anti-hIGF humanized antibody to hIGF can be measured by ELISA, biosensor Biacore and the like. Additionally, the activity of the antibody of the present invention to inhibit the hIGF functions can be measured by examining the influence of the antibody upon the in vivo or in vitro proliferation of a cell line showing hIGF-dependent proliferation.

(1) Activity Evaluation by ELISA

The binding ELISA is a method for measuring the binding activity of an antigen and an antibody, including a step of immobilizing the antigen on a 96-well ELISA plate, a step of reacting a primary antibody, a step of reacting a labeled secondary antibody capable of recognizing the primary antibody, and a step of detecting the label.

Specifically, the antigen to be immobilized includes the purified protein of hIGF-I or hIGF-II, peptides with partial sequences thereof and the like. The primary antibody includes analytes such as culture supernatants of hybridoma or purified antibodies. The secondary antibody includes antibodies capable of recognizing the primary antibody labeled with biotin, an enzyme, a chemiluminescence substance, a radioisotope or the like. Specifically, the secondary antibody includes a horseradish peroxidase-labeled anti-rat immunoglobulin (hereinafter referred to as rIg) mouse antibody or the like.

The competitive ELISA is a method in which hIGF-I or hIGF-II is immobilized in advance on the ELISA plate, an antibody as the substance to be measured and hIGF-I or hIGF-II are simultaneously added thereto and allowed to react, and the reactivity of another or the same antigen added to the reaction solution to inhibit the reaction of the antigen immobilized on the plate with the antibody to be measured is measured based on the changes in the amount of the primary antibody binding to the plate. Changes in the binding amount of the antibody are detected by the secondary antibody to the antibody. Also, reactivity with an intact hIGF and antigen epitope can be analyzed by the competitive ELISA using the intact hIGF and a partial peptide of the hIGF. Whether or not the antibody is recognizing three-dimensional structure of the hIGF can be examined by a conventional structural analysis.

As the structural analysis, X-ray crystallographic analysis, magnetic nuclear resonance analysis and the like can, for example, be exemplified.

(2) Activity Evaluation by Biosensor Biacore

According to the measurement with a biosensor BIACORE, a very small quantity of change in mass generated on the surface of a sensor tip accompanied by the association and dissociation between two molecules is detected as SPR signal by an optical phenomenon. From the association constant (hereinafter referred to as Kass) and dissociation constant (hereinafter referred to as Kdiss) obtained from the measurement by this method, a binding constant (hereinafter referred to as KA) of KA=Kass/Kdiss is calculated. KA is expressed by a unit of M−1. The measurement with a biosensor BIOCORE can be carried out under optimum measuring conditions in accordance with the instructions attached thereto. Regarding the optimum measuring conditions, it is desirable that amount of the ligand to be immobilized on the sensor tip is within the range between the minimum value calculated by formula 1 and the maximum value calculated by formula 2. Also, it is desirable that binding amount of the analyte is equal to or smaller than the maximum binding amount calculated by formula 3. In formulae 1, 2 and 3, ligand means a molecule to be immobilized on the sensor tip, analyte means a molecule to be added via a channel system, and S means the number of ligand binding site. RU is abbreviation of resonance unit which indicates changed amount of mass per unit area on the sensor tip surface, wherein 1 RU=1 pg/mm2. According to the measurement with a biosensor BIACORE, analysis of the binding constant based on the binding mode of each protein can be carried out by setting flow rate and washing condition such that the maximum binding amount can be maintained.

Minimum immobilized amount (RU)=200×1/S×(molecular weight of ligand/molecular weight of analyte) (Formula 1)

Maximum immobilized amount (RU)=1000×1/S× (molecular weight of ligand/molecular weight of analyte) (Formula 2)

Maximum binding amount=molecular weight of analyte×immobilized amount of ligand (RU)/molecular weight of ligand×S (Formula 3)

4. Use of Humanized Antibody or Antibody Fragment Thereof of the Present Invention Since the anti-hIGF antibody and the antibody fragment of the present invention bind to hIGF-I and hIGF-II specifically and with approximately the same degree, further inhibit the functions thereof, it is considered that they are useful for treating hIGF-mediated diseases and diseases showing pathological progressing due to abnormally promoted hIGF production. In addition, since most part of a humanized antibody is derived from an amino acid sequence of a human antibody in comparison with an antibody of a non-human animal, it does not show immunogenicity in the human body, and its repeated administration is possible and long-term persistency of its effect is expected.

hIGF-mediated diseases and diseases showing pathological progressing due to abnormally promoted hIGF production include cancer, acromegaly, diabetic complications and the like.

The anti-hIGF antibody and the antibody fragment thereof of the present invention can be administered as it is, but it is desirable in general to provide it as a pharmaceutical preparation produced by an optional method well known in the technical field of manufacturing pharmacy, by mixing it with one or more pharmacologically acceptable carriers.

As the administration route, it is advisable to use the most effective route in the treatment. Examples thereof can include oral administration and parenteral administrations such as intraoral, intratracheal, intrarectal, subcutaneous, intramuscular, intraarticular and intravenous administrations. In case of the antibody or peptide preparations, intraarticular and intravenous administrations are preferable.

Examples of the administration form include sprays, capsules, tablets, granules, syrups, emulsions, suppositories, injections, ointments, tapes and the like.

Examples of appropriate preparations for oral administration include emulsions, syrups, capsules, tablets, powders, granules and the like.

Liquid preparations such as emulsions and syrups can be produced by using, as additives, water, saccharides such as sucrose, sorbitol and fructose, glycols such as polyethylene glycol and propylene glycol, oils such as sesame oil, olive oil and soybean oil, antiseptics such as p-hydroxybenzoic acid esters, and flavors such as strawberry flavor and peppermint.

Capsules, tablets, powders, granules and the like can be produced by using, as additives, excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, and plasticizers such as glycerin.

Examples of preparations appropriate for parenteral administration include injections, suppositories, sprays and the like.

Injections are prepared by using a carrier comprising a salt solution, a glucose solution or a mixture of both, and the like.

Suppositories are prepared using a carrier such as cacao butter, hydrogenated fat or carboxylic acid.

Sprays are prepared by using the antibody or the peptide as such or in combination with a carrier which facilitates dispersion and absorption of the antibody or the peptide in the form of fine particles without stimulating the mouth and the airway mucous membrane of a recipient.

Specific examples of the carrier include lactose, glycerin and the like. Preparations such as aerosol and dry powder can be formed depending on properties of the antibody or the peptide and the carrier used. These parenteral preparations may comprise the ingredients listed as additives in the oral preparations.

The dose or the number of administrations varies with the desired therapeutic effects, the administration method, the therapeutic period, the age, the body weight and the like. It is usually from 10 μg/kg to 10 mg/kg per day for an adult.

The present invention will be described below by referring to Examples, the present invention is not limited thereby.

EXAMPLES

Example 1

Construction of cDNAs Encoding the VH and VL of Anti-Human IGF Human CDR-Grafted Antibody (1) Design of the Amino Acid Sequences of VH and VL of Anti-Human IGF Human CDR-Grafted Antibody First, amino acid sequences of the VH of the anti-human IGF human CDR-grafted antibody was designed as follows.

A amino acid sequence of the FR of the VH of a human antibody was selected as follow for grafting the amino acid sequences of the CDR of the VH (SEQ ID NO:2) of the anti-hIGF rat monoclonal antibody KM1468 (Rat IgG2b) identified in Reference Example 5, item 1.

When a human antibody FR having the highest homology with the FR of the VH of the anti-hIGF rat monoclonal antibody KM1468 was searched from an official database, an antibody CAM (Proceedings of the National Academy of Sciences of the United States of America, 77, 3239-3243, 1980) showed the highest homology of 81.6%. Accordingly, the amino acid sequence of the VH of anti-hIGF human CDR-grafted antibody (hereinafter referred to as anti-hIGF CDR-grafted antibody) was designed as follows based the amino acid sequence of FR of the VH of antibody CAM (hereinafter referred to as Cam).

In the FR of Cam, there were 4 positions where amino acid sequences are not univocally determined (13th position, 74th position, 77th position and 90th position), and amino acid residues which are not common in the amino acid sequences of FR of the VH of human antibody were observed at 3rd position and 40th position therein. In order to reduce immunogenicity, these amino acid residues were modified into amino acid residues which are found in human antibodies with a high frequency (Sequences of Proteins of Immunological Interest, US Dept. Health and Human Services, 1991). By grafting the CDR amino acid sequences of the VH of the anti-hIGF rat monoclonal antibody KM1468 into an appropriate position of the designed amino acid sequences of the Cam-derived FR, the VH amino acid sequence CamHV0 as represented by SEQ ID NO:11 was designed.

Then, the VH amino acid sequence of an anti-hIGF CDR-grafted antibody comprising the FR of a human antibody differing from Cam was designed as follows.

Kabat, et al. have classified various VHs of known human antibodies into three subgroups based on the amino acid sequence homology thereof (HSG I to III), and reported the consensus sequences of each subgroups (Sequences of Proteins of Immunological Interest, US Dept. Health and Human Services, 1991). Since antibodies having these consensus sequences expected low immunogenicity in human, the amino acid sequence of VH of an anti-hIGF CDR-grafted antibody was designed based on FRs of these consensus sequences. In order to prepare an anti-hIGF CDR-grafted antibody with a higher activity, an amino acid sequence with the highest homology with the amino acid sequence of the FR of the VH of anti-hIGF rat monoclonal antibody KM1468 was selected among the consensus amino acid sequences of FR in the 3 VH subgroups of human antibodies. The results of the homology search are shown in Table 1. As shown in Table 1, the amino acid sequence of the FR of the VH of the anti-hIGF rat monoclonal antibody KM1468 showed the highest homology with the amino acid sequence of the FR of the subgroup III.

TABLE 1

Homology between the FR amino acid sequence with the consensus sequence in each subgroups of the VH of human antibodies and the FR amino acid sequence of the VH of the anti-hIGF rat monoclonal antibody KM1468

| HSG I | HSG II | HSG III |
|---|---|---|
| 63.2% | 56.3% | 86.2% |

Based on the above results, by grafting the amino acid sequence of the CDR in the VH of the anti-hIGF rat monoclonal antibody KM1468 into an appropriate position of the amino acid sequence of the FR with the consensus sequence of the subgroup III, the amino acid sequence HV0(3) of the VH of the anti-hIGF CDR-grafted antibody as represented by SEQ ID NO:54 was designed.

Then, the amino acid sequence of the VL of the anti-hIGF CDR-grafted antibody was designed as follows. So as to graft the amino acid sequence of the CDR of the VL (represented by SEQ ID NO:4) of the anti-hIGF rat monoclonal antibody KM1468 as determined in Reference Example 5.1, the amino acid sequence of the FR of the VL of human antibody was selected as follows.

Kabat, et al. have classified various VLs of known human antibodies into four subgroups, based on the amino acid sequence homology thereof (HSG I to IV), and reported on consensus sequences of each subgroups (Sequences of Proteins of Immunological Interest, US Dept. Health and Human Services, 1991). An amino acid sequence of the FR with the highest homology with the amino acid sequence of the FR of the VL of the anti-hIGF rat monoclonal antibody KM1468 was searched in the amino acid sequences of the FR of the consensus sequences of the 4 VL subgroups of human antibodies. The results of the homology search are shown in Table 2. As shown in Table 2, the FR amino acid sequence of the VL of the anti-hIGF rat monoclonal antibody KM1468 showed the highest homology with the FR amino acid sequence of the subgroup IV.

TABLE 2

Homology between the FR amino acid sequence with the consensus sequences in each subgroups of the VL of human antibody and the FR amino acid sequence of the VL of the anti-hIGF rat monoclonal antibody KM1468

| HSG I | HSG II | HSG III | HSG IV |
|---|---|---|---|
| 66.3% | 61.3% | 66.3% | 67.5% |

Based on the above results, the amino acid sequence LV0 of the VL of the anti-hIGF CDR-grafted antibody as represented by SEQ ID NO:14 was designed, by grafting the amino acid sequence of the CDR in the VL of the anti-hIGF rat monoclonal antibody KM1468 into an appropriate position of the amino acid sequence of the FR of the consensus sequence of the subgroup IV of the VL of human antibody.

Further, the VL of human antibody with the second highest homology was of subgroup I. Therefore, an amino acid sequence LV0(1) of the VL of the anti-hIGF CDR-grafted antibody as represented by SEQ ID NO:55 was designed, by grafting the amino acid sequence of the CDR in the VL of the anti-hIGF rat monoclonal antibody KM1468 into an appropriate position of the FR amino acid sequence of the consensus sequence of subgroup I.

The amino acid sequences of the VH, CamHV0 and HV0 (3), and the amino acid sequences of the VL, LV0 and LV0(1), of the anti-hIGF CDR-grafted antibody as designed above are sequences in which the CDR amino acid sequences of the anti-hIGF rat monoclonal antibody KM1468 are only grafted into the selected FR amino acid sequences of human antibody. In the case of human CDR-grafted antibodies, generally, the binding activities to antigens thereof are frequently decreased when grafting with only the amino acid sequence of CDR therein is carried out. In order to avoid the decrease, certain amino acid residues among the FR amino acid residues different between human antibodies and antibodies of non-human animal, which are considered to influences on the binding activity to antigens, are grafted together with the amino acid sequences of the CDR. Accordingly, in this Example, the FR amino acid residues considered to have influences on the binding activity to antigens were identified as described below.

First, the three-dimensional structures of the V regions of human CDR-grafted antibodies comprising four combinations of the amino acid sequences CamHV0 and HV0(3) of the VHs of the anti-hIGF CDR-grafted antibody and the amino acid sequences LV0 and LV0(1) of the VLs of the anti-hIGF CDR-grafted antibody designed above [hereinafter the anti-hIGF CDR-grafted antibody in combination of the VH with the amino acid sequence of CamHV0 and the VL with the amino acid sequence LV0 are referred to CamHV0/LV0; the abbreviation mode is also applicable to CamHV0/LV0, CamHV0/LV0(1), HV0(3)LV0 and HV0(3)LV0(1)] is constructed by using a computer modeling technique. The three-dimensional structures coordinate were prepared using a software AbM (manufactured by Oxford Molecular), and display of the three-dimensional structures using a software Pro-Explore (manufactured by Oxford Molecular) or RasMo1 (manufactured by Glaxo) according to the respective attached manufacture's instructions. Also, computer models of the three-dimensional structure of the V region of the anti-hIGF rat monoclonal antibody KM1468 were constructed in the same manner. Further, a three-dimensional structure models of variants of an amino acid sequence were constructed in the same manner, in which certain residues of the amino acid sequences of the FR of each V regions of the human CDR-grafted antibodies, different from the amino acid residues in the amino acid sequence of the V region of the anti-hIGF rat monoclonal antibody KM1468, were modified with other the amino acid residues observed in the amino acid sequence of the anti-hIGF rat monoclonal antibody KM1468, and the three-dimensional structure was compared with the three-dimensional structures of the V region of the anti-hIGF rat monoclonal antibody KM1468, the 4 combinations of the human CDR-grafted antibodies which are original of each variant.

Consequently, 1st position Gln, 97th position Ala and 98th position Arg in CamHV0 were selected as residues having influences to antibody binding activities to antigens, by changing the three-dimensional structures of the antigen-binding sites among the amino acid residues in the FR of the V regions of the variants. Although the influence to the antibody activity was not obvious in view of the three-dimensional structure models, the residue was also selected as a candidate for such modification, because the 42nd position amino acid residue was Thr in the anti-hIGF rat monoclonal antibody KM1468 while the 42nd position amino acid residue is generally Gly, and a possibly is suggested that the amino acid residue Thr may possibly play a specific role in the anti-hIGF rat monoclonal antibody KM1468. Also, in HV0 (3), 49th position Ser, 77th position Asn, 84th position Asn, 93rd position Val, 97th position Ala and 98th position Arg were selected; in LV0, 4th position Met, 9th position Asp, 10th position Ser, 11th position Leu, 15th position Leu, 22nd position Asn, 35th position Tyr, 39th position Pro, 42nd position Pro, 45th position Leu, 46th position Leu, 69th position Asp, 70th position Phe, 71st position Thr, 82nd position Val and 84th position Val were selected; in LV0(1), 4th position Met, 9th position Ser, 10th position Ser, 11th position Leu, 15th position Val, 35th position Tyr, 39th position Pro, 42nd position Ala, 45th position Leu, 46th position Leu, 69th position Asp, 70th position Phe, 71st position Thr1 and 82nd position Phe were selected, respectively.

To modify at least one of the amino acid residues selected in such manner was modified into an amino acid residue in the amino acid sequence of the V region of the anti-hIGF rat monoclonal antibody KM1468, the amino acid sequences of the VH and VL of human CDR-grafted antibody, with various modifications are designed.

(2) Construction of cDNA Encoding CamHV0 cDNA encoding the amino acid sequence CamHV0 designed in Example 1 (1) was constructed as described below.

First, the secretion signal sequence of the H chain of the anti-hIGF rat monoclonal antibody KM1468 was linked to the designed amino acid sequence at N-terminal, which corresponds to an amino acid sequence to SEQ ID NO:2 from the amino acid residues of 1st position to 19th position. The resulting sequence is represented by SEQ ID NO:12. Then, the amino acid sequence was converted into genetic codons. When several genetic codons exist for one amino acid residue, the frequencies of codon usage (Sequences of Proteins of Immunological Interest, US Dept. Health and Human Services, 1991) observed in the nucleotide sequences of antibody genes were considered.

By linking the converted genetic codons, the nucleotide sequence of cDNA encoding the amino acid sequence was designed and is represented by SEQ ID NO:13. Annealing nucleotide sequences containing restriction recognition sequences for cloning into a vector for expression of humanized antibody as primer for PCR amplification were, respectively, added to the 5'- and 3'-terminal of the nucleotide sequence. The resulting nucleotide sequence was defined as the nucleotide sequence encoding CamHV0. The nucleotide sequence was divided into 4 fragments from the 5'-terminal, in which each fragment comprises about 150 bases (adjoining nucleotide sequences are designed such that they have a complimentary sequence of about 20 bases on their terminals). 4 synthetic oligo-DNAs represented by SEQ ID NOs:30, 31, 32 and 33 were synthesized in reciprocal order of a sense chain and an antisense chain (manufactured by Fasmac).

PCR was carried out by adding each of the synthetic oligo-DNA to the reaction solution attached to the product KOD-plus polymerase (manufactured by TOYOBO) to give a final concentration of 0.1 µM, and adjusting the total volume to 50 µl with 0.4 µM of T3 primer (manufactured by Takara Bio), 0.4 µM of T7 primer and 1 unit of KOD-plus polymerase (manufactured by TOYOBO). The reaction was carried out by 35 cycles, each cycle consisting of 94° C. for 30 seconds, 60° C. for 30 seconds and 72° C. for 60 seconds. After the reaction, the reaction solution was fractionated by 1.5% agarose gel electrophoresis. Using a gel extraction kit (manufactured by QIAGEN), gene fragment about 0.5 kbp was recovered. After the digestion reaction of the recovered gene fragments using restriction enzymes EcoRI (manufactured by Takara Bio) and XhoI (manufactured by Takara Bio), the reaction solution was fractionated by 1.5% agarose gel electrophoresis, and then the gene fragments after digestion with the restriction enzymes was recovered, using a gel extraction kit (manufactured by QIAGEN).

In the same manner as in the case of the above gene fragments, after digestion reaction using restriction enzymes EcoRI (manufactured by Takara Bio) and XhoI (manufactured by Takara Bio), pBluescript II SK(−) (hereinafter referred to as pBS) (manufactured by Stratagene) was fractionated and recovered. Using Ligation High (manufactured by TOYOBO), pBS and the gene fragments of CamHV0 were ligated according to the attached instruction. Using a recombinant plasmid DNA solution obtained by the ligation, an *Escherichia coli* DH5α was transformed. From the transformant, the plasmid DNA was prepared using MiniPrep (manufactured by QIAGEN) according to the attached instruction. Using BigDye Terminator Cycle Sequencing FS Ready Reaction Kit ver.3 (manufactured by Applied Biosystems), the nucleotide sequence was analyzed to obtain a plasmid pBS/

CamHV0 comprising a nucleotide sequence encoding the aimed amino acid sequence CamHV0, as shown in FIG. 1.

(3) Construction of cDNA Encoding Variants of the VH of Anti-hIGF CDR-Grafted Antibody cDNA encoding the variants of the VH of the anti-hIGF CDR-grafted antibody as designed in Example 1 (1) was constructed as follows. The genetic codons for the amino acid residues after the modification may be the genetic codons observed in the anti-hIGF rat monoclonal antibody KM1468. Additionally, the PCR reaction was carried out using KOD-plus polymerase (manufactured by TOYOBO) according to the attached instruction.

The synthetic oligo-DNAs manufactured by Fasmac was used below.

(3-1) Construction of cDNA Encoding the Amino Acid Sequence of a Variant Prepared by Modifying the 1st Position Gln, 97th Position Ala, and 98th Position Arg into Glu, Thr and Thr, Respectively (Hereinafter Referred to as QAR)

Using pBS/CamHV0 obtained in Example 1(2) as a template and also using the synthetic oligo-DNA represented by SEQ ID NO:38 and the synthetic oligo-DNA represented by SEQ ID NO:41, PCR was carried out by 35 cycles, each cycle consisting of 94° C. for 30 seconds, 58° C. for 45 seconds and 72° C. for 60 seconds. After the reaction, the reaction solution was fractionated by 1.5% agarose gel electrophoresis to recover the aimed gene fragment in the same manner as in Example 1(2). The recovered gene fragment was cloned into pBS, to obtain a plasmid pBS/QAR comprising cDNA represented by SEQ ID NO:17, which encodes the aimed amino acid sequence QAR.

(3-2) Construction of cDNA Encoding the Amino Acid Sequence of a Variant Prepared by Modifying the 1st Position Gln, 42nd Position Gly, 97th Position Ala, 98th Position and Arg into Glu, Thr, Thr and Thr, Respectively (Hereinafter Referred to as QGAR)

Using pBS/CamHV0 obtained in Example 1(2) as a template and also using the synthetic oligo-DNA represented by SEQ ID NO:38 and the synthetic oligo-DNA represented by SEQ ID NO:39, a 5'-QG gene fragment of about 250 bp was amplified by PCR in the same manner as described in above (3-1); and also using the synthetic oligo-DNA represented by SEQ ID NO:40 and the synthetic oligo-DNA represented by SEQ ID NO:41, a 3'-GAR gene fragment of about 250 bp was amplified by PCR in the same manner as described in above (3-1). The aimed gene fragments were recovered by fractionation by 1.5% agarose gel electrophoresis. Using each gene fragment recovered, the T3 primer at the 5'-terminal of the 5'-QG gene fragment (manufactured by Takara Bio) and the T7 primer at the 3'-terminal of the 3'-GAR gene fragment (manufactured by Takara Bio), PCR was carried out in the same manner as described above (3-1). After the reaction, the reaction solution was fractionated by 1.5% agarose gel electrophoresis in the same manner as in Example 1(2), to recover gene fragment of about 500 bp. The recovered gene fragment was cloned into pBS, to obtain an aimed plasmid pBS/QGAR comprising cDNA represented by SEQ ID NO:18, which encodes the amino acid sequence QGAR represented by SEQ ID NO:26.

(4) Construction of cDNA Encoding LV0 cDNA encoding the amino acid sequence LV0 designed in Example 1(1) was constructed as follows.

First, the secretion signal sequence of the L chain of the anti-hIGF rat monoclonal antibody KM1468 was linked to the N-terminal of the designed amino acid sequence, which corresponds to an amino acid sequence from the amino acid residue of 1st position to 22nd position in SEQ ID NO:4. The resulting sequence is represented by SEQ ID NO:15. Then, the amino acid sequence was converted to genetic codons. When several genetic codons exist for one amino acid residue, the frequencies of codon usage (Sequences of Proteins of Immunological Interest, US Dept. Health and Human Services, 1991) observed in the nucleotide sequences of antibody genes were considered.

By linking the converted genetic codons, the nucleotide sequence of cDNA encoding the amino acid sequence was designed and is represented by SEQ ID NO:16. Annealing nucleotide sequences containing restriction recognition sequences for cloning into a vector for expression of humanized antibody as primer for PCR amplification were, respectively, added to the 5'- and 3'-terminals of the nucleotide sequence. The nucleotide sequence was divided into 4 fragments from the 5'-terminal, in which each fragment comprises about 150 bases (adjoining nucleotide sequences are designed such that they have a complimentary sequence of about 20 bases on their terminals). 4 synthetic oligo-DNAs represented by SEQ ID NOs: 34, 35, 36 and 37 were synthesized in reciprocal order of a sense chain and an antisense chain (manufactured by Fasmac).

Using each synthetic oligo-DNAs, procedures of PCR to cloning into pBS were carried out in the same manner as in Example 1 (2), to obtain a plasmid pBS/LV0 comprising cDNA represented by SEQ ID NO:16, which encodes the aimed amino acid sequence LV0 as shown in FIG. 1.

(5) Construction of cDNA Encoding a Variant of VL of the Anti-hIGF CDR-Grafted Antibody cDNA encoding the amino acid sequence of a variant of the VL of the anti-hIGF CDR-grafted antibody as designed in Example 1(1) was constructed as follows. The genetic codons for the amino acid residues after the modification may be the genetic codons observed in the anti-hIGF rat monoclonal antibody KM1468. Additionally, PCR was carried out using KOD-plus polymerase (manufactured by TOYOBO) according to the attached instruction.

(5-1) Construction of cDNA Encoding the Amino Acid Sequence of a Variant Prepared by Modifying the 4th Position Met, 9th Position Asp, 10th Position Ser, 11th Position Leu, 15th Position Leu, 22nd Position Asn, 35th Position Tyr, 42nd Position Pro, 45th Position Leu, 46th Position Leu, 69th Position asp, 70th Position Phe, 71st Position Thr, 82nd Position Val, and 84th Position Val into Leu, Thr, Thr, Met, Pro, Thr, Phe, Ser, Pro, Trp, Ser, Tyr, Ser, Ala and Thr, Respectively (Hereinafter Referred to as A11)

The nucleotide sequence of cDNA encoding the amino acid sequence A11 as represented by SEQ ID NO:19 was divided into 4 fragments from the 5'-terminal, in which each fragment comprises about 150 bases (adjoining nucleotide sequences are designed such that they have a complimentary sequence of about 20 bases on their terminals). 4 Synthetic oligo-DNAs represented by SEQ ID NOs:46, 47, 48 and 49 were synthesized in reciprocol order a sense chain and an antisense chain.

Using each synthetic oligo-DNAs, procedures of PCR to cloning into pBS were carried out in the same manner as in Example 1 (2), to obtain a plasmid pBS/A11 comprising cDNA represented by SEQ ID NO:19, which encodes the aimed amino acid sequence A11.

(5-2) Construction of cDNA Encoding the Amino Acid Sequence of a Variant Prepared by Modifying the 42nd Position Pro, 45th Position Leu, 46th Position Leu, 82nd Position Val, and 84th Position Val into Ser, Pro, Trp, Ala and Thr, Respectively (Hereinafter Referred to as PLLVV)

Using pBS/LV0 obtained in Example 1(4) as a template and also using the synthetic oligo-DNA represented by SEQ ID NO:42 and the synthetic oligo-DNA represented by SEQ ID NO:50, PCR was carried out to prepare a 5'-PLL gene fragment; using pBS/LV0 obtained in Example 1(4) as a template and also using the synthetic oligo-DNA represented by SEQ ID NO:44 and the synthetic oligo-DNA represented by SEQ ID NO:49, PCR was carried out to prepare a 3'-VV gene fragment in the same manner as described in above (3-1), respectively. After the reaction, the aimed gene fragments were recovered by the fractionation of the reaction solution by 1.5% agarose gel electrophoresis in the same manner as in Example 1(2). Using each gene fragments recovered, the T3 primer (manufactured by Takara Bio) at the 5'-terminal of the 5'-PLL gene fragment and the T7 primer (manufactured by Takara Bio) at the 3'-terminal of the 3'-VV gene fragment, procedures from PCR to pBS cloning were carried out in the same manner as described in above (3-1). A plasmid pBS/PLLVV comprising cDNA represented by SEQ ID NO:20 was recovered, which encodes the aimed amino acid sequence pLLVV.

(5-3) Construction of cDNA Encoding the Amino Acid Sequence of a Variant Prepared by Modifying 22nd Position Asn, 42nd Position Pro, 45th Position Leu, 46th Position Leu, 82nd Position Val, and 84th Position Val into Thr, Ser, Pro, Trp, Ala and Thr, Respectively (Hereinafter Referred to as NPLLVV)

Using pBS/LV0 obtained in Example 1(4) as a template and also using the synthetic oligo-DNA represented by SEQ ID NO:42 and the synthetic oligo-DNA represented by SEQ ID NO:43, PCR was carried out in the same manner as described in above (3-1), to amplify the NPLL gene fragment. In the same manner as in Example 1(2), the reaction solution was subjected into 1.5% agarose gel electrophoresis to recover the aimed gene fragment. Using the recovered NPLL gene fragment and a synthetic oligo-DNA represented by SEQ ID NO:50, PCR was carried out in the same manner as in above (3-1), to amplify the 5'-NPLL gene fragment. In the same manner as in Example 1(2), the reaction solution was subjected into 1.5% agarose gel electrophoresis to recover the aimed gene fragment. Using the recovered 5'-NPLL gene fragment, the 3'-VV gene fragment obtained in above (5-2), T3 primer (manufactured by Takara Bio), and T7 primer (manufactured by Takara Bio), procedures from PCR to pBS cloning were carried out in the same manner as described in above (3-2), to obtain a plasmid pBS/NPLLVV comprising cDNA represented by SEQ ID NO:21, which encodes the aimed amino acid sequence NPLLVV.

(5-4) Construction of cDNA Encoding the Amino Acid Sequence of a Variant Prepared by Modifying 22nd Position Asn, 35th Position Tyr, 42nd Position Pro, 45th Position Leu, and 46th Position Leu into Thr, Phe, Ser, Pro and Trp, Respectively (Hereinafter Referred to as NYPLL)

Using pBS/NPLLVV obtained above in (5-4) as a template and using a synthetic oligo-DNA represented by SEQ ID NO:50 and a synthetic oligo-DNA represented by SEQ ID NO:53, PCR was carried out in the same manner as described in above (3-1), to recover the 5'-NYPLL-1 gene fragment. On the other hand, using pBS/LV0 obtained above in Example 1(4) as a template and using a synthetic oligo-DNA represented by SEQ ID NO:44 and T7 primer (manufactured by Takara Bio), PCR was carried out in the same manner as described in above (3-1), to recover a 3'-LV0 gene fragment. Using the 5'-NYPLL-1 gene fragment, the 3'-LV0 gene fragment, T3 primer (manufactured by Takara Bio) and T7 primer (manufactured by Takara Bio), procedures from PCR to pBS cloning were carried out in the same manner as described in above (3-2), to obtain a plasmid pBS/NYPLL comprising cDNA represented by SEQ ID NO:22, which encodes the aimed amino acid sequence NYPLL.

(5-5) Construction of cDNA Encoding the Amino Acid Sequence of a Variant Prepared by Modifying 22nd Position Asn, 35th Position Tyr, 42nd Position Pro, 45th Position Leu, 46th Position Leu, 69th Position Asp, 70th Position Phe, 71st Position Thr, 82nd Position Val, and 84th Position Val into Thr, Phe, Ser, Pro, Trp, Ser, Tyr, Ser, Ala and Thr, Respectively (Hereinafter Referred to as NYPLL3A11)

Using pBS/NYPLL obtained in above (5-4) as a template and using a synthetic oligo-DNA represented by SEQ ID NO:45 and a synthetic oligo-DNA represented by SEQ ID NO:50, PCR was carried out in the same manner as described in above (3-1), to recover the 5'-NYPLL-2 gene fragment. On the other hand, using pBS/A11 obtained in above (5-1) as a template and using a synthetic oligo-DNA represented by SEQ ID NO:44 and T7 primer (manufactured by Takara Bio), PCR was carried out in the same manner as described in above (3-1), to recover a 3'-3A11 gene fragment. Using the 5'-NYPLL-2 gene fragment, the 3'-3A11 gene fragment, T3 primer (manufactured by Takara Bio) and T7 primer (manufactured by Takara Bio), procedures from PCR to pBS cloning were carried out in the same manner as described above in (3-2), to obtain a plasmid pBS/NYPLL3A11 comprising cDNA represented by SEQ ID NO:27, which encodes the aimed amino acid sequence NYPLL3A11.

(5-6) Construction of cDNA Encoding the Amino Acid Sequence of a Variant Prepared by Modifying 42nd Position Pro, 45th Position Leu, 69th Position Asp, 70th Position Phe, and 71st Position Thr into Ser, Pro, Ser, Tyr and Ser, Respectively (Hereinafter Referred to as PLDFT)

Using pBS/LV0 obtained in above Example 1(4) as a template and using a synthetic oligo-DNA represented by SEQ ID NO:51 and M13RV primer (manufactured by Takara Bio), PCR was carried out in the same manner as described in above (3-1), to recover a 5'-PL gene fragment. On the other hand, using pBS/LV0 as a template and using the synthetic oligo-DNA represented by SEQ ID NO:52 and M13M20 primer (manufactured by Takara Bio), PCR was carried out in the same manner as described in above (3-1), to recover a 3'-DFT gene fragment. Using the 5'-PL gene fragment, the 3'-DFT gene fragment, M13RV primer (manufactured by Takara Bio) and M13M20 primer (manufactured by Takara Bio), procedures from PCR to pBS cloning were carried out in the same manner as described in above (3-2), to obtain a plasmid pBS/PLDFT comprising cDNA represented by SEQ ID NO:24, which encodes the aimed amino acid sequence PLDFT represented by SEQ ID NO:28.

(5-7) Construction of cDNA Encoding the Amino Acid Sequence of a Variant Prepared by Modifying 42nd Position Pro, 45th Position Leu, 46th Position Leu, 69th Position Asp, 70th Position Phe and 71st Position Thr into Ser, Pro, Trp, Ser, Tyr and Ser, Respectively (Hereinafter Referred to as PLL-DFT)

Using pBS/PLLVV obtained above as a template and using the synthetic oligo-DNA represented by SEQ ID NO:45 and M13RV primer (manufactured by Takara Bio), PCR was carried out in the same manner as described in above (3-1), to recover a 5'-PLL gene fragment. Using the 5'-PLL gene fragment, the 3'-DFT gene fragment obtained above in (5-6), M13RV primer (manufactured by Takara Bio) and M13M20 primer (manufactured by Takara Bio), procedures from PCR to pBS cloning were carried out in the same manner as described in above (3-2), to obtain a plasmid pBS/PLLDFT comprising cDNA represented by SEQ ID NO:25, which encodes the aimed amino acid sequence PLLDFT represented by SEQ ID NO:29.

Example 2

Expression of Anti-hIGF CDR-Grafted Antibody (1) Construction of Anti-hIGF CDR-Grafted Antibody Expression Vector cDNA encoding the amino acid sequence CamHV0 or the amino acid sequence LV0 as obtained in Example 1(2) and 1(4) and cDNAs encoding the amino acid sequences of the variants thereof were inserted into an appropriate position of an vector for expression of humanized antibody pKANTEX93 as described in WO 97/10354, to construct various anti-hIGF CDR-grafted antibody expression vectors as follows.

cDNAs encoding the amino acid sequences CamHV0, QAR and QGAR and pKANTEX93 were treated with restriction enzymes NotI and ApaI, respectively, to fractionate and recover gene fragments of about 0.5 kbp and 12 kbp, respectively, by 1.5% agarose gel electrophoresis. Using Ligation High (manufactured by TOYOBO), pKANTEX93 and the gene fragments encoding the amino acid sequences CamHV0, QAR and QGAR were ligated, to obtain plasmids pKANTEX93/CamHV0, pKANTEX93/QAR and pKANTEX93/QGAR.

So as to insert VL cDNAs, cDNAs encoding the amino acid sequences LV0, NYPLL3A11, PLDFT and PLLDFT and pKANTEX93/CamHV0, pKANTEX93/QAR and pKANTEX93/QGAR as obtained above were treated with restriction enzymes EcoRI and BsiWI, respectively, to fractionate gene fragments of about 0.45 kbp and 12.5 kbp by 1.5% agarose gel electrophoresis, and then recovered the gene fragments using a gel extraction kit (manufactured by QIAGEN). Using Ligation high (manufactured by TOYOBO), pKANTEX93/CamHV0, pKANTEX93/QAR and pKANTEX93/QGAR were ligated with various VL gene fragments. Using then the recombinant plasmid DNA solutions obtained through the ligation reaction, *Escherichia coli* strain DH5α was transformed. Using MiniPrep (manufactured by QIAGEN), plasmid DNAs were prepared from the transformant strains according to the attached instruction. Using then BigDye Terminator Cycle Sequencing FS Ready Reaction Kit ver.3 (manufactured by Applied Biosystems), the nucleotide sequences were analyzed, to obtain plasmids pKANTEX93/CamHV0/LV0, pKANTEX93/QAR/LV0, pKANTEX93/QGAR/LV0, pKANTEX93/CamHV0/NYPLL3A11, pKANTEX93/QGAR/PLDFT and pKANTEX93/QGAR/PLLDFT shown in FIG. 2.

(2) Stable Expression of Anti-hIGF CDR-Grafted Antibody Using Animal Cell

Anti-hIGF CDR-grafted antibody was stably expressed in an animal cell as follows.

After introducing 10 μg of each expression vector for the anti-hIGF CDR-grafted antibody as obtained in Example 2(1) into a rat myeloma cell line YB2/0 (ATCC CRL1581) of $4 \times 10^6$ cells by electroporation (Cytotechnology, 3, 133-140, 1990), the resulting cell was suspended in 40 mL of H-SFM (5) culture medium [H-SFM containing 5% FCS (manufactured by Gibco BRL)]. Then, the suspension was dispensed at 200 μl/well on a 96-well culture plate (manufactured by Sumitomo Bakelite). After culturing for 24 hour in 5% $CO_2$ incubator at 37° C., G418 was added thereto to give a concentration of 0.5 mg/ml and the culturing was continued for 1 to 2 weeks. A colony of a transformant resistant against G418 appeared. From the confluent wells, the culture supernatant was recovered, and then carried out ELISA for determining the amount of human IgG described in Example 2 (5) to select the anti-hIGF CDR-grafted antibody expression cell.

In order to increase the antibody expression amount using a dhfr gene amplification system, the transformants in wells in which expression of the anti-hIGF CDR-grafted antibody was found in the culture supernatants were suspended to give a density of $1 \times$ to $2 \times 10^5$ cells/mL in H-SFM (5) containing 0.5 mg/ml of G418 and 50 nM of methotrexate (hereinafter referred to as MTX; manufactured by Sigma) which is an inhibitor of a dhfr gene product dehydrofolate reductase (hereinafter referred to as DHFR), and dispensed at 1 mL/well on a 24-well culture plate (manufactured by Greiner). Transformants showing 50 nM MTX resistant were induced by culturing for 1 to 2 weeks in 5% $CO_2$ incubator at 37° C. When the transformants became confluent in the wells, the concentration of the anti-hIGF CDR-grafted antibody in the culture supernatant was measured according to ELISA for determining the amount of human IgG as described in Example 2(5) to confirm the expression amount of the antibody.

Regarding transformants of wells where expression of the anti-hIGF CDR-grafted antibody was found in the culture supernatants, the MTX concentration was increased to 100 nM and then 200 nM by the same method as described above. Finally, a transformant which can grow in H-SFM(5) containing 0.5 mg/ml G418 and 200 nM MTX and can express the anti-hIGF CDR-grafted antibody highly was obtained. The human IgG contained in the culture supernatant of the transformant was measured by ELISA for determining human IgG as described in Example 2(5), to obtain an MTX-resistant transformant with the highest expression amount of the anti-hIGF CDR-grafted antibody. If necessary, the MTX-resistant transformant was subjected to single cell cloning by limited dilution method once or twice, to obtain a transformant clone with the highest expression amount of the anti-hIGF CDR-grafted antibody.

The each anti-hIGF CDR-grafted antibodies are referred to as follows in combination of the amino acid sequences of each V region, respectively. Anti-hIGF CDR-grafted antibody produced from the transformant introduced with the plasmid pKANTEX93/CamHV0/LV0 is referred to as CamHV0/LV0; anti-hIGF CDR-grafted antibody produced from the transformant introduced with the plasmid pKANTEX93/QAR/LV0 is referred to as QAR/LV0; anti-hIGF CDR-grafted antibody produced from the transformant introduced with the plasmid pKANTEX93/QGAR/LV0 is referred to as QGAR/LV0; anti-hIGF CDR-grafted antibody produced from the transformant introduced with the plasmid pKANTEX93/CamHV0/NYPLL3A11 is referred to as CamHV0/NYPLL3A11; anti-hIGF CDR-grafted antibody produced from the transformant introduced with the plasmid pKANTEX93/QGAR/PLDFT is referred to as QGAR/PLDFT; and anti-hIGF CDR-grafted antibody produced from the transformant introduced with the plasmid pKANTEX93/QGAR/PLLDFT is referred to as QGAR/PLLDFT.

(3) Purification of Anti-hIGF CDR-Grafted Antibody from Culture Supernatant

A transformant expressing each anti-hIGF CDR-grafted antibody as obtained in Example 2(2) was suspended in 500 mL of GIT culture medium (manufactured by Dainippon Pharmaceutical) containing 0.5 mg/ml G418 and 200 nM MTX, to 1 to 2×10⁵ cells/mL, and dispensed in a 2-liter roller bottle (manufactured by Falcon). After culturing in an incubator for 7 to 8 days at 37° C., when the cells became confluent, the culture supernatant was recovered. Using a column Prosep-A (manufactured by Bioprocessing) according to the attached instruction, various anti-hIGF CDR-grafted antibodies were purified from about one liter of the culture supernatant.

(4) Evaluation of Binding Activity of Anti-hIGF CDR-Grafted Antibody to Antigen (Binding ELISA)

A conjugate of hIGF-I (manufactured by Fujisawa Co., Ltd.) with methylated BSA (manufactured by SIGMA) was prepared and used as an antigen to be immobilized on an ELISA plate. That is, methylated BSA dissolved in distilled water was mixed with hIGF to a ratio of methylated BSA: hIGF-I=1:8 (weight ratio) at 4° C. The resulting mixture was agitated with a vortex mixer for 10 seconds, to obtain a conjugate of hIGF-I with methylated BSA (hereinafter referred to as mBSA-hIGF-I).

The above mBSA-hIGF-I was dispensed at 50 µl/well on a 96-well ELISA plate (manufactured by Greiner) to give a hIGF-I concentration of 20 ng/ml and then left overnight at 4° C. for immobilization. After washing with PBS, PBS containing 1% BSA (hereinafter referred to as BSA-PBS) was dispensed in 100 µl/well to react at room temperature for 1 hour to carry out blocking of the remaining active groups. Discarding BSA-PBS, the culture supernatant of each of the various transformants or each of various purified hIGF CDR-grafted antibodies was dispensed at 50 µl/well to react at room temperature for 2 hours. After the reaction, each well was washed with PBS containing 0.05% Tween 20 (hereinafter referred to as Tween-PBS). Then, HRP-labeled anti-human IgG antibody (manufactured by American Qualex) in 2000-fold dilution was dispensed at 50 µl/well as a secondary antibody to react at room temperature for 1 hour. After the reaction and subsequent washing with Tween-PBS, an ABTS substrate solution [a solution prepared by dissolving 0.55 g of 2,2'-azinobis(3-ethylbenzothiazoline-6-sulfonic acid) ammonium salt in 1 liter of 0.1 M citrate buffer (pH 4.2), and further adding thereto 1 µl/ml of hydrogen peroxide just before use] was dispensed at 50 µl/well to effect color development, and then absorbance at 415 nm (hereinafter referred to as OD415) was measured using a plate reader Emax (manufactured by Molecular Devices).

(5) ELISA for Assaying Human IgG (Sandwich ELISA)

Anti-human IgG antibody (manufactured by American Qualex) was diluted to 2000-fold with PBS, which was then dispensed at 50 µl/well on a 96-well ELISA plate (manufactured by Greiner) and left at 4° C. overnight for immobilization, to prepare the plate therefor. Procedures after the procedure for blocking the remaining active groups with BSA-PBS were carried out in the same manner as the binding ELISA described above in Example 2(4).

Example 3

Verification of Reactivity of Anti-hIGF CDR-Grafted Antibody

The binding activities of purified samples of the various anti-hIGF CDR-grafted antibodies obtained in Example 2(3) to hIGF were examined, using the binding ELISA described in Example 2(4) or a measuring method of the binding affinity thereof with hIGF using the biosensor Biacore (manufactured by Biacore) described below in Example 3(2). In the following examination, purified anti-hIGF human chimeric antibody KM3002 according to the method described in Reference Example 6(4) was used.

(1) Binding ELISA for mBSA-hIGF-I

The binding activities of the various anti-hIGF CDR-grafted antibodies purified by the method described in Example 2(3) to mBSA-hIGF-I were examined. The results are shown in FIG. 3. As shown in FIG. 3a, the binding activity to hIGF-I of the anti-hIGF CDR-grafted antibody CamHV0/LV0 prepared by grafting only the CDR of the anti-hIGF rat monoclonal antibody KM1468 into the FR of the human antibody Cam and the FR in the consensus sequence of the subgroup IV of the VL was decreased to about 1/50-fold compared with that of the anti-hIGF human chimeric antibody KM3002. Therefore, the increase of the binding activity thereof to hIGF-I was examined via modifications of amino acids in each of the FRs.

As shown in FIG. 3a, no increase of the binding activity to hIGF-I of the anti-hIGF CDR-grafted antibody QAV/LV0 prepared by modifying 1st position Gln, 97th position Ala and 98th position Arg in the VH of the anti-hIGF CDR-grafted antibody CamHV0/LV0 into Glu, Thr and Thr, respectively was observed, compared with CamHV0/LV0. However, as shown in FIG. 3a, about 25-fold increase of the binding activity to hIGF-I of the anti-hIGF CDR-grafted antibody QGAR/LV0 prepared by modifying 42nd position Gly into Thr in addition to the amino acid modifications of 1st position Gln, 97th position Ala and 98th position Arg therein into Glu, Thr and Thr, respectively was observed, compared with CamHV0/LV0, and that the activity thereof was about ½-fold the binding activity of the anti-hIGF human chimeric antibody KM3002.

The above results clearly indicate that the binding activity to hIGF-I can be elevated by the modification of 42nd position Gly into Thr in CamHV0 in addition to the amino acid modifications of 1st position Gln into Glu, 97th position Ala into Thr and 98th position Arg into Thr therein and that 42nd position Gly which the contributions to the activity from the three-dimensional model was unknown plays an important role in the activity of the present antibody significantly.

As to VL variants, alternatively, it was observed that the binding activity to hIGF-I of the anti-hIGF CDR-grafted antibody CamHV0/NYPLL3A11 with modifications of 22nd position Asn into Thr, 35th position Tyr into Phe, 42nd position Pro into Ser, 45th position Leu into Pro, 46th position Leu into Trp, 69th position Asp into Ser, 70th position Phe into Tyr, 71st position Thr into Ser, 82nd position Val into Ala, and 845th position Val into Thr in the VL of the anti-hIGF CDR-grafted antibody CamHV0/LV0 was increased to about 25-fold of the anti-hIGF CDR-grafted antibody CamHV0/LV0 as shown in FIG. 3a and that the activity thereof was about ½-fold the binding activity of the anti-hIGF human chimeric antibody KM3002. The aforementioned results indicate that the modifications of the VL can increase the binding activity of hIGF-I. Therefore, the binding activity to hIGF-I of the anti-hIGF CDR-grafted antibody QGAR/NYPLL3A11 with a combination of the VH of the amino acid sequence QGAR and the VL of the amino acid sequence NYPLL3A11 was examined. The results are shown in FIG. 3b. Consequently, it was verified that the binding activity of such anti-hIGF CDR-grafted antibody QGAR/NYPLL3A11 with the combination of the VH and VL was at the same levels as of the binding activity of the anti-hIGF human chimeric antibody KM3002.

So as to identify amino acid residues important for the increase of the activity among 10 modified amino acid residues in the VL variant NYPLL3A11, the binding activities to hIGF-I of an anti-hIGF CDR-grafted antibody QGAR/PLDFT and an anti-hIGF CDR-grafted antibody QGAR/PLLDFT in a combination of a VL variant of the amino acid sequence PLDFT, a VL variant of the amino acid sequence PLLDFT, both with a smaller number of modified amino acid residues and a VH variant of the amino acid sequence QGAT were examined.

The results are shown in FIG. 3b. Consequently, it is clearly shown that the binding activities of these 2 types of the anti-hIGF CDR-grafted antibody QGAR/PLDFT and the anti-hIGF CDR-grafted antibody QGAR/PLLDFT were at the same level as the binding activity of the anti-hIGF human chimeric antibody KM3002 to hIGF-I.

(2) Measuring Binding Affinity Using Biosensor Biacore

Using a biosensor Biacore 2000 (manufactured by Biacore), the binding activities of the anti-hIGF human chimeric antibody KM3002 and the various anti-hIGF CDR-grafted antibodies purified above in Example 2(3) to hIGF-I and hIGF-II were measured as binding affinity as described below. For diluting samples and as reaction buffers in measurement, HBS-EP (10 mM HEPES, 150 mM NaCl, 3 mM EDTA, 0.005% Tween 20 pH 7.4) (manufactured by Biacore) was used.

Using an amine coupling kit (manufactured by Biacore), recombinant hIGF-I (manufactured by Fujisawa Pharmaceutical Co., Ltd.) and hIGF-II (manufactured by R & D) were immobilized at 18.5 pg/mm$^2$ or 26.7 pg/mm$^2$, respectively, on sensor tip CM-5 (manufactured by Biacore). After various antibodies which were diluted 5 steps in 2-fold serial dilutions as analytes added at a flow of 5 µl/minute for 4 minutes to observe a binding reaction, the dissociation reaction was subsequently observed over 5 minutes. After the dissociation reaction, 5 µl of 30 mM hydrochloric acid was added once, to regenerate the sensor chip surface. The reaction was done at 25° C. Based on the reaction curves at various concentrations, the binding constant Kass and dissociation constant Kdiss were calculated, to calculate the binding constants $K_A$ ($M^{-1}$) of these various antibodies. The results are shown in Table 3.

TABLE 3

| Antibodies | $K_A$ (hIGF-I) | $K_A$ (hIGF-II) |
| --- | --- | --- |
| Anti-hIGF human chimeric antibody KM3002 | $2.94 \times 10^9$ | $2.24 \times 10^9$ |
| CamHV0/LV0 | $0.17 \times 10^9$ | $0.39 \times 10^9$ |
| QAR/LV0 | $0.17 \times 10^9$ | $0.45 \times 10^9$ |
| QGAR/LV0 | $0.78 \times 10^9$ | $1.75 \times 10^9$ |
| CamHV0/NYPLL3A11 | $1.32 \times 10^9$ | $2.1 \times 10^9$ |
| QGAR/NYPLL3A11 | $2.32 \times 10^9$ | $3.96 \times 10^9$ |
| QGAR/PLDFT | $2.31 \times 10^9$ | $4.02 \times 10^9$ |
| QGAR/PLLDFT | $2.78 \times 10^9$ | $3.52 \times 10^9$ |

The $K_A$ of the anti-hIGF CDR-grafted antibody CamHV0/LV0 to hIGF-I or hIGF-II was decreased to about 1/17-fold or about 1/6-fold, respectively, compared with that of the anti-hIGF human chimeric antibody KM3002.

Compared with the anti-hIGF CDR-grafted antibody CmaHV0/LV0, the increase of the binding affinity of the anti-hIGF CDR-grafted antibody QAR/LV0 was scarcely observed. But, $K_A$ of the anti-hIGF CDR-grafted antibody QGAR/LV0 to hIGF-I and hIGF-II was increased to about 5-fold compared with that of the anti-hIGF CDR-grafted antibody CamHV0/LV0.

Alternatively, $K_A$ of an anti-hIGF CDR-grafted VL antibody CamHV0/NYPLL3A11 to hIGF-I or hIGF-II was increased to about 8-fold or about 5-fold, respectively, compared with that of the anti-hIGF CDR-grafted antibody CamHV0/LV0. Additionally, $K_A$ of an anti-hIGF CDR-grafted antibody QGAR/NYPLL3A11 to hIGF-I or hIGF-II was increased to about 14-fold or about 10-fold, respectively, compared with that of the anti-hIGF CDR-grafted antibody CamHV0/LV0.

The binding affinity of the anti-hIGF CDR-grafted antibody QGAR/PLDFT or the anti-hIGF CDR-grafted antibody QGAR/PLLDFT with a combination of the VL of an amino acid sequence PLDFT or PLLDFT with the optimally modified amino acid residues to hIGF-I or hIGF-II was almost similar to those of the anti-hIGF CDR-grafted antibody QGAR/NYPLL3A11 and the anti-hIGF human chimeric antibody KM3002. No decrease of their activities due to the reduction of the number of the modified amino acid residues was observed.

Example 4

Effect of Anti-hIGF CDR-Grafted Antibodies on the Inhibition of hIGF-Dependent Proliferation The inhibitory activity of the anti-hIGF CDR-grafted antibody as a purified sample as obtained above in Example 2(3) on the hIGF-dependent proliferation was confirmed as follows.

A human colorectal cancer cell line HT-29 (ATCC HTB-38) was adjusted in a TF/BSA culture medium [D-MEM/F-12 (manufactured by Gibco BRL) supplemented with 10 µg/ml human transferrin (manufactured by Gibco BRL) and 200 µg/mL BSA] to $5 \times 10^4$ cells/mL. Then, the cells were dispensed at 100 µL/well on a 96-well culture plate. Further, hIGF-/I or hIGF-II diluted to a concentration of 40 to 80 ng/mL with a TF/BSA culture medium was added at 50 µl/well, while each of the anti-hIGF CDR-grafted antibodies diluted to each concentration with the TF/BSA culture medium was added at 50 µl/well, for culturing in 5% $CO_2$ incubator for 5 days at 37° C. After culturing, a cell proliferation reagent WST-1 (manufactured by Roche) was dispensed at 20 µl/well, for culturing in 5% $CO_2$ incubator for 2 to 3 hours at 37° C. The absorbance at OD450 nm (hereinafter referred to as OD450) was measured by a plate reader Emax (manufactured by Molecular Devices).

The results are shown in FIGS. 4 to 6, respectively. The inhibitory activity of each anti-hIGF CDR-grafted antibody on the hIGF-dependent proliferation were highly correlated with the results of the binding activities to hIGF-I by binding ELISA and the binding affinities with hIGF as measured with a biosensor Biacore in Example 3. In other words, the anti-hIGF CDR-grafted antibodies with high binding affinities with hIGF had high inhibitory activities on the hIGF-dependent proliferation. It was shown that among the prepared anti-hIGF CDR-grafted antibodies, the anti-hIGF CDR-grafted antibody QGAR/NYPLL3A11, the anti-hIGF CDR-grafted antibody QGAR/PLDFT, and the anti-hIGF CDR-grafted antibody QGAR/PLLDFT had the same degree of the inhibitory activities on the hIGF-dependent proliferation as that of the anti-hIGF human chimeric antibody KM3002.

The results described above indicate that the anti-hIGF CDR-grafted antibody QGAR/NYPLL3A11, the anti-hIGF CDR-grafted antibody QGAR/PLDFT and the anti-hIGF CDR-grafted antibody QGAR/PLLDFT have high binding affinities with hIGF-I and hIGF-II and high activities on the neutralization of the biological activities of hIGF-I and hIGF-II. Additionally because most of amino acid residues in these anti-hIGF CDR-grafted antibodies are derived from sequences of human antibodies, these antibodies are useful as therapeutic agents of various human diseases of which the hIGF functions are involved in the formation of pathologies.

Reference Example 1

Preparation of Anti-hIGF Monoclonal Antibody (1) Immunization of Animal and Preparation of Antibody-Producing Cell A recombinant hIGF-I (manufactured by R & D) was made into a conjugate with a methylated BSA (manufactured by Sigma) for the purpose of increasing its immunogenicity, and use as the immunogen. Thus, methylated BSA dissolved in redistilled water was mixed at 4° C. so as to make methylated BSA:hIGF=1:4 (ratio by weight) and stirred for 10 seconds in a vortex mixer. After that, it was mixed with complete Freund's adjuvant or incomplete Freund's adjuvant using a syringe equipped with a connecting needle at a ratio by volume of 1:1 to give an immunogen (hereinafter referred to as methylated BSA-hIGF-I).

The methylated BSA-hIGF-I (equivalent to 100 μg of hIGF-I) prepared as above using a complete Freund's adjuvant was administered to a 5-weeks old female SD rat and, from 2 weeks thereafter, an immunogen which was similarly prepared using an incomplete Freund's adjuvant was administered once a week for 4 times in total.

Blood was collected from venous plexus of the fundus of the eye, antibody titer in its serum was checked by a binding ELISA shown in Reference Example 1(4) and spleen was excised from a rat showing a sufficient antibody titer after 3 days from the final immunization.

After the spleen was cut into pieces in an MEM medium (manufactured by Nissui Seiyaku), loosened by tweezers and centrifuged (at 1200 rpm for 5 minutes), the supernatant was discarded, the resulting precipitate was treated with a Tris-ammonium chloride buffer (pH 7.65) for 1 to 2 minutes to eliminate erythrocytes, and the remainder was washed with MEM for 3 times to be used for cell fusion.

(2) Preparation of Mouse Myeloma Cells

An 8-azaguanine-resistant mouse myeloma cell line P3-U1 was incubated in a common medium and not less than $2 \times 10^7$ cells were secured upon cell fusion to be used as a parent cell for cell fusion.

(3) Preparation of Hybridoma

The rat spleen cell prepared in Reference Example 1(1) and the myeloma cell prepared in (2) were mixed so as to make their ratio 10:1 followed by centrifuging (at 1200 rpm for 5 minutes), the supernatant was discarded, 0.2 to 1.0 mL of a fusion medium (a mixture of 2 g of PEG-1000, 2 mL of MEM and 0.7 mL of dimethyl sulfoxide) per $10^2$ rat spleen cell was added to the precipitated cell with stirring at 37° C., 1 to 2 mL of MEM was added for several times every 1 to 2 minutes and MEM was further added thereto so that the total volume was made 50 mL. After centrifugation (at 900 rpm for 5 minutes), the supernatant was discarded and the resulting cell were gently loosened and suspended in 100 mL of HAT medium.

The suspension was dispensed at 100 μL/well on a 96-well plate and incubated in a 5% $CO_2$ incubator for 10 to 14 days at 37° C. The culture supernatant was subjected to a binding ELISA shown in Reference Example 1(4) to select wells which reacted with methylated BSA-hIGF-I and did not react with methylated BSA-BSA which is a negative control [a conjugate prepared by the same reaction as in the above Referential Example 1(1) using BSA], and anti-hIGF-I rat monoclonal antibody producing hybridoma were established by carrying out single cell cloning twice by changing the medium to HT medium and the normal medium.

As a result, 6 hybridoma clones of KM 1468, KM 1469, KM 1470, KM 1471, KM 1472 and KM 1473 having reactivities shown in FIG. 7 were obtained. When subclass of the antibody produced by each hybridoma was examined by an ELISA using a subclass typing kit, all of the subclasses were IgG2b.

(4) Selection of Monoclonal Antibody (Binding ELISA)

As to an antigen to be immobilized to an ELISA plate, the methylated BSA-hIGF-I prepared in Reference Example 1(1) was used while, as to a negative control, methylated BSA-BSA was used. The above antigen in 10 μg/mL in terms of concentration of hIGF-I or BSA was dispensed at 50 μL/well on a 96-well ELISA plate (manufactured by Greiner) and left over night at 4° C. for immobilized. After washing with PBS, PBS containing 1% of BSA (hereinafter referred to as BSA-PBS) was added at 100 μL/well and reacted at room temperature for 1 hour to block the remaining active group. The BSA-PBS was discarded and then rat antiserum to be immunized, culture supernatant of hybridoma which produces anti-hIGF-I monoclonal antibody or purified anti-hIGF-I monoclonal antibody was dispensed at 50 μL/well and reacted at room temperature for 2 hours. After the reaction, each well was washed with PBS containing 0.05% of Tween 20 (hereinafter referred to as Tween-PBS) and 50 μL/well of peroxidase-labeled rabbit anti-rat Ig antibody diluted to 4000-fold (manufactured by Dako) was added as a secondary antibody and allow to react at room temperature for 1 hour. After the reaction, it was washed with Tween-PBS, 50 μL/well of ABTS substrate solution [a solution prepared by dissolving 0.55 g of ammonium 2,2'-azino-bis(3-ethylbenzothiazoline-6-sulfonate) in 1 L of 0.1 M citrate buffer (pH 4.2) followed by adding 1 μL/ml of an aqueous solution of hydrogen peroxide immediately before use] was then added thereto to effect color development and absorbance at 415 nm (hereinafter referred to as OD415) was measured using a plate reader Emax (manufactured by Molecular Devices).

(5) Purification of Monoclonal Antibody

The hybridoma clone prepared in Reference Example 1(3) was intraperitoneally injected in an amount of 5 to $20 \times 10^6$ cells/mouse into pristane-treated female Balb/c nude mice of 8-weeks old. After 10 to 21 days, ascites was collected (1 to 8 mL/mouse) from the mice where the hybridoma turned ascites cancer and centrifuged (at 3000 rpm for 5 minutes) to remove solids. After that, IgG fraction was purified by a caprylic acid precipitation method (Antibodies, A Laboratory Manual, Cold Spring Harbor Laboratory, 1988) to give a purified monoclonal antibody.

Reference Example 2

Examination of Reactivity of Anti-hIGF Monoclonal Antibody (1) Reactivity of hIGF-I to Natural Three-Dimensional Structure Reactivity of 6 types of anti-hIGF monoclonal antibody selected in Reference Example 1(3) to hIGF-I maintaining natural three-dimensional structure in a liquid phase system was examined by the following competitive ELISA.

A plate where the methylated BSA-hIGF-I prepared in Reference Example 1(1) was immobilized as shown in Reference Example 1(4) was prepared, hIGF-I which was diluted in 5-fold serial dilutions from 20 μg/mL was dispensed at 50 μL/well, then a solution where the purified antibody of the anti-hIGF monoclonal antibody was diluted (KM 1468: 6.0 μg/mL, KM 1470: 1.0 μg/mL, KM 1471: 0.16 μg/mL, KM 1472: 7.0 μg/mL, KM 1473: 1.2 μg/mL) was dispensed at 50 μL/well followed by mixing and the mixture was left at room temperature for 2 hours. After the reaction, it was washed with Tween-PBS and then 50 μL/well of peroxidase-labeled rabbit anti-rat Ig antibody (manufactured by Dako) diluted to 4000-fold was added followed by reacting at room temperature for 1 hour. After the reaction, it was washed with Tween-PBS, 50 μL/well of an ABTS substrate solution [a solution prepared by dissolving 0.55 g of ammonium 2,2'-azino-bis (3-ethylbenzothiazoline-6-sulfonate) in 1 L of 0.1 M citrate buffer (pH 4.2) followed by adding with 1 μL/ml of an aqueous solution of hydrogen peroxide immediately before use] was added thereto to effect color development and OD415 was measured using a plate reader Emax (manufactured by Molecular Devices).

As shown in FIG. 8, all of the six anti-hIGF monoclonal antibodies of the present invention showed reactivity to a natural three-dimensional structure of hIGF-I. In addition, when KM 1468 showing the highest sensitivity in the present system was used, hIGF-I having a natural three-dimensional structure contained in the liquid phase system can be detected up to a concentration of 16 ng/mL.

(2) Reactivity of Anti-hIGF Rat Monoclonal Antibody KM1468 with hIGF-I by Competitive ELISA A possibility was suggested in above (1) that the anti-hIGF antibody KM1468 recognizes three-dimensional structure of hIGF-I. However, since there is also a possibility that KM1468 recognizes amino acid primary sequence, its reactivity with hIGF-I partial peptides was analyzed.

(2-1) Synthesis of Partial Peptide of hIGF-I

A partial peptide of hIGF-I was synthesized according to a process mentioned in WO01/64754. The synthesized peptide is a peptide corresponding to 1st to 18th (SEQ ID NO:56; hereinafter referred to as p1-18), 14th to 30th (SEQ ID NO:57; hereinafter referred to as p14-30), 24th to 35th (SEQ ID NO:58; hereinafter referred to as p24-35), 29th to 41st (SEQ ID NO:59; hereinafter referred to as p29-41), 36th to 47th (SEQ ID NO:60; hereinafter referred to as p36-47), 41st to 56th (SEQ ID NO:61; hereinafter referred to as p41-56), 52nd to 70th (SEQ ID NO:62; hereinafter referred to as p52-70), 53rd to 61st (SEQ ID NO:63; hereinafter referred to as p53-61) and 61st to 70th (SEQ ID NO:64; hereinafter referred to as p61-70) of hIGF-I and was designed to cover the full length of hIGF-I. In the above-mentioned peptides, a sequence where Cys existing therein was substituted with Ser or Ala was synthesized. With regard to the sequence corresponding to 41st to 56th, a sequence having an inner Cys (SEQ ID NO:65; hereinafter referred to as p41-56C) was also synthesized.

(2-2) Analysis of Antigen-Recognition Site of Anti-hIGF Monoclonal Antibody

Analysis of antigen-recognizing site of anti-hIGF rat antibody KM 1468 was examined by the following competitive ELISA using various kinds of peptides synthesized in the above (2-1).

As shown in Reference Example 1(4), a plate where antigen was immobilized was prepared, various antibodies diluted to 4.0 μg/mL were dispensed at 50 μL/well and either alone or various combinations of various peptide solutions diluted in 3-fold serial dilutions from 50 μg/mL or hIGF-I was dispensed at 50 μL/well followed by mixing and reacting at room temperature for 1 hour. After the reaction, the above was washed with Tween-PBS, a peroxidase-labeled rabbit anti-rat Ig antibody (manufactured by Dako) diluted to 4000-fold was added at 50 μL/well and was left at room temperature for 1 hour. After the reaction, it was washed with Tween-PBS, 50 μL/well of an ABTS substrate solution [a solution prepared by dissolving 0.55 g of ammonium 2,2'-azino-bis(3-ethylbenzothiazoline-6-sulfonate) in 1 L of 0.1 M citrate buffer (pH 4.2) followed by adding 1 μL/mL of aqueous hydrogen peroxide solution thereto immediately before use] was added thereto to effect color development and OD415 was measured using a plate reader Emax (manufactured by Molecular Devices). The result is shown in terms of a relative value (%) where the OD415 when antibody was added alone was defined as 100.

The result is shown in FIG. 9. As shown in FIG. 9, binding of KM 1468 to hIGF-I was dose-dependently inhibited by hIGF-I but, in the cases of various peptides, no inhibitory activity was noted regardless of sole or combined use thereof. The above result strongly suggests that KM 1468 is not a mere amino acid primary sequence of hIGF-I but recognizes a three-dimensional structure of hIGF-I.

(3) Verification of Cross Reactivity of Anti-hIGF Rat Antibody KM1468 by Competitive ELISA Cross reactivity of the purified anti-hIGF rat antibody KM1468 with hIGF-II and human insulin was examined by the competitive ELISA shown below. As the antigens, hIGF-I (manufactured by Pepro Tech), hIGF-II (manufactured by Pepro Tech) and human insulin (manufactured Wako Pure Chemical Industries) were used.

The methylated BSA-hIGF-I antigen prepared in Reference Example 1(1) or a methylated BSA-hIGF-II antigen prepared in the same manner as in Reference Example 1(1) was immobilized on a plate in accordance with the method shown in Reference Example 1(4), at a concentration of 0.1 μg/ml in the case of the methylated BSA-hIGF-I antigen, or at a concentration of 1.0 μg/ml in the case of the methylated BSA-hIGF-II antigen, KM1468 diluted to 0.6 μg/ml was dispensed at 25 μl/well, and then each of 4-fold serial dilutions of hIGF-I, hIGF-II or human insulin prepared by starting from 20 μg/ml was dispensed at 25 μl/well, mixed and left at room temperature for 1 hour. After the reaction and subsequent washing with Tween-PBS, 1000-fold diluted peroxidase-labeled rabbit anti-rat Ig antibody (manufactured by DAKO) was added at 50 μl/well as the secondary antibody in the case of the anti-hIGF antibody KM1468. After the reaction and subsequent washing with Tween-PBS, 50 μl/well of an ABTS substrate solution [a solution prepared by dissolving 0.55 g of 2,2'-azinobis(3-ethylbenzothiazoline-6-sulfonic acid) ammonium salt in 1 liter of 0.1 M citrate buffer (pH 4.2), and further adding thereto 1 μl/ml of hydrogen peroxide just before use] was added to effect color development, and then OD415 was measured using a plate reader Emax (manufactured by Molecular Devices). The results are represented by relative values (%) wherein OD415 when an antibody was added alone was defined as 100.

The results are shown in FIG. 10. As shown in FIG. 10A, binding of the anti-hIGF antibody KM1468 to hIGF-I was strongly inhibited by hIGF-I and hIGF-II. In the same manner, as shown in FIG. 10B, binding of the anti-hIGF antibody KM1468 to hIGF-II was strongly inhibited by hIGF-I and hIGF-II. In addition, these inhibitions by hIGF-I and hIGF-II were the same degree. That is, it is shown that the anti-hIGF antibody KM1468 can react with both of hIGF-I and hIGF-II by almost the same strength. On the other hand, binding of the anti-hIGF antibody KM1468 to hIGF-I or hIGF-II was not inhibited by human insulin.

Reference Example 3

Verification of Reactivity of Anti-hIGF Antibody with IGF

Comparison of the reactivity of KM1468 and 2 types of commercially available anti-hIGF antibodies with antigens was carried out in the following manner. As the antibodies, the anti-hIGF antibody KM1468, sm1.2 as a commercially available anti-hIGF-I antibody (manufactured by Upstate Biotechnology) and S1F2 as a commercially available anti-hIGF-II antibody (manufactured by Upstate Biotechnology) were used. As the antigens, hIGF-I (manufactured by Pepro Tech), hIGF-II (manufactured by Pepro Tech) and human insulin (manufactured by Wako Pure Chemical Industries) were used.

(1) Measurement of Binding Affinity Using Surface Plasmon Resonance

In order to analyze the binding activity of the anti-hIGF rat monoclonal KM1468 to an antigen hIGF-I or hIGF-II, the binding affinities of the anti-hIGF rat monoclonal KM1468, a commercially available anti-hIGF-I antibody sm1.2 and a commercially available anti-hIGF-II antibody S1F2 to hIGF-I and hIGF-II were assayed in the following manner using the biosensor Biacore 2000 (manufactured by Biacore) utilizing surface plasmon resonance. For the diluting samples and as the reaction buffers in measurement, HBS-EP (10 mM HEPES, 150 mM NaCl, 3 mM EDTA, 0.005% Tween 20, pH 7.4) (manufactured by Biacore) was used.

Using an amine coupling (manufactured by Biacore), hIGF-I or hIGF-II were immobilized at 36.0 pg/mm$^2$ or 41.7 pg/mm$^2$, respectively, on sensor tip CM-5 (manufactured by Biacore). After 3 types of the antibodies which were diluted in 6 steps in 2-fold serial dilutions starting from 20 μg/ml as analytes, were added at a flow rate of 20 μl/minute for 2 minutes, the dissociation of the analytes was subsequently observed over 5 minutes. The reaction was carried out at 25° C. Based on the reaction curves at various concentrations, association constant Kass and dissociation constant Kdiss were calculated, to calculate the binding constant $K_A$ (M$^{-1}$) of these various antibodies. The binding constant $K_A$ is calculated by $K_A$=Kass/Kdiss. The results are shown in Table 4.

TABLE 4

|  | KM1468 | Sm1.2 | S1F2 |
|---|---|---|---|
| $K_A$ (hIGF-I) | 7.86 × 10$^9$ | 1.86 × 10$^8$ | 4.62 × 10$^8$ |
| $K_A$ (hIGF-II) | 8.63 × 10$^9$ | 7.35 × 10$^7$ | 2.40 × 10$^9$ |

The $K_A$ of the anti-hIGF antibody KM1468 to hIGF-I was 7.86×10$^9$ M$^{-1}$, and the $K_A$ to hIGF-II was 8.63×10$^9$ M$^{-1}$. Since the $K_A$ ratio of KM1468 to hIGF-I and hIGF-II was almost 1:1, it was shown that KM1468 can bind strongly to both of hIGF-I and hIGF-II with an almost the same degree. On the other hand, the $K_A$ of the commercially available anti-hIGF-I monoclonal antibody sm1.2 to hIGF-I was 1.86× 10$^8$ M$^{-1}$, and the $K_A$ to hIGF-II was 7.35×10$^7$ M$^{-1}$. The $K_A$ of the anti-hIGF antibody KM1468 to hIGF-I and hIGF-II were about 42-fold higher to hIGF-I and about 120-fold higher to hIGF-II, in comparison with the $K_A$ of the commercially available anti-hIGF-I antibody sm1.2. Also, the $K_A$ of the commercially available anti-hIGF-II antibody S1F2 to hIGF-I was 4.62×10$^8$ M$^{-1}$, and the $K_A$ value to hIGF-II was 2.4×10$^9$ M$^{-1}$. The $K_A$ of the anti-hIGF antibody KM1468 to hIGF-I and hIGF-II were about 18-fold higher to hIGF-I and about 3.6-fold higher to hIGF-II, in comparison with the $K_A$ of the commercially available anti-hIGF-II antibody S1F2. That is, it was shown that the anti-hIGF antibody KM1468 has a strong binding activity to each of hIGF-I and hIGF-II, in comparison with the commercially available anti-hIGF-I antibody sm1.2 and the commercially available anti-hIGF-II antibody S1F2.

Reference Example 4

Influence of Anti-hIGF Rat Monoclonal KM1468 on the Proliferation of hIGF-I Expressing Cell (1) Construction of hIGF-I Expressing Cell A transformant in which hIGF-I gene was transferred into a human lung cancer cell line A549 (ATCC CCL-185) was prepared in the following manner.

(1-1) Cloning of hIGF-I Gene and Preparation of Expression Vector

A 45.6 μg portion of total RNA was prepared from 1×10$^7$ cells of a human lung cancer cell strain PC-9 (British Journal of Cancer, 39, 15, 1976) using an RNA preparation kit RNeasy (manufactured by QIAGEN) in accordance with the instructions attached thereto. Using a 5 μg portion of the prepared total RNA, cDNA was synthesized using Superscript II (manufactured by GIBCO-BRL) in accordance with the instructions attached thereto.

Using the synthesized cDNA as the template, the hIGF-I gene was cloned by PCR. As primers for hIGF-I gene amplification, synthetic DNAs respectively having the nucleotide sequences shown in SEQ ID NOS: 66 and 67 were designed. Each synthetic DNAs contains a restriction enzyme recognizing sequence in its 5'-terminal for cloning it into plasmids pBluescript II SK (−) (manufactured by Stratagene) and pKANTEX93 (WO 97/10354). Specifically, 20 ng of the cDNA synthesized from the human lung cancer cell line PC-9, obtained in the above, was added to a buffer solution containing 50 μl of KOD(+) DNA Polymerase-attached KOD (+) Buffer #1 (manufactured by TOYOBO), 0.2 mM dNTPs, 2 mM magnesium chloride and 1 μM of the synthetic DNA respectively having the nucleotide sequences shown in SEQ ID NOS: 27 and 28, and using a DNA thermal cycler Gene-Amp PCR System 9600 (manufactured by PERKIN ELMER), the mixture was heated at 94° C. for 1 minute, and then, by adding 2.5 units of KOD DNA Polymerase (manufactured by TOYOBO), a cycle of 30 seconds at 94° C., 30 seconds at 62° C. and 30 seconds at 72° C. was repeated 30 cycles. A 50 μl portion of each reaction solution was digested with restriction enzymes EcoRI (manufactured by Takara Shuzo) and SalI (manufactured by Takara Shuzo) and then subjected to an agarose gel electrophoresis, and a PCR product of a gene encoding hIGF-I of about 0.5 kb was recovered using QIAquick Gel Extraction Kit (manufactured By QIAGEN).

Next, 0.1 μg of DNA obtained by digesting the plasmid pBluescript II SK(−) (manufactured by Stratagene) with the restriction enzymes EcoRI and SalI and then dephosphorylating the termini with Calf Intestine Alkaline Phosphatase (manufactured By Takara Shuzo, hereinafter referred to as CIAP) and 0.1 μg of each PCR product obtained in the above were prepared into 7.5 μl by adding sterile water and then reacted at 16° C. overnight by adding 7.5 μl of Ligation High (manufactured by TOYOBO). Using the recombinant plasmid DNA solution obtained in this manner, an *Escherichia* coli DH5α (manufactured by TOYOBO) was transformed. Each plasmid DNA was prepared from the transformant, which subjected to the reaction using BigDye Terminator Cycle Sequencing FS Ready Reaction Kit (manufactured by Applied Biosystems) in accordance with the instructions attached thereto, and its nucleotide sequence was determined using a nucleotide sequence automatic analyzer ABI PRISM 377 (manufactured by Applied Biosystems). As a result, the plasmid of interest pBS(II)SK(−)/hIGF-I having a gene sequence encoding hIGF-I shown in FIG. 11 was obtained.

Next, the restriction enzyme fragment (EcoRI-KpnI) of the pBS(II)SK(−)/hIGF-I obtained in the above encoding hIGF-I ligated with the EcoRI-KpnI fragment of pKANTEX93, and a plasmid pKANTEX93/hIGF-I shown in FIG. 11 was constructed. Nucleotide sequence of the plasmid pKANTEX93/hIGF-I was determined in the same manner as described above using the nucleotide sequence automatic analyzer ABI PRISM 377. As a result, the plasmid of interest pKANTEX93/hIGF-I containing a gene encoding hIGF-I was obtained.

(1-2) Preparation of hIGF-I Transformant

An hIGF-I expressing cell was prepared in the following manner by introducing the plasmid pKANTEX93/hIGF-I obtained in above (1-1) into an animal cell.

The plasmid pKANTEX93/hIGF-I was digested with a restriction enzyme AatII (manufactured by TOYOBO) to linearize, and an 8 μg portion thereof was introduced into $4 \times 10^6$ cells of the human lung cancer cell line A 549 (ATCC CCL-185) by the electroporation method (Cytotechnology, 3, 133-140, 1990), and then the cells were suspended in 15 ml of RPMI medium [RPMI 1640 medium (manufactured by Invitrogen) containing 10% FCS and 50 μg/ml gentamicin (manufactured by Nakalai Tesque)] and transferred into a T75 flask (manufactured by Sumilon). After 24 hours of culturing at 37° C. in a 5% $CO_2$ incubator, G418 was added thereto to a concentration of 0.2 mg/ml and further cultured for 1 to 2 weeks. An A549/hIGF-I transformant having G418 resistance (hereinafter referred to as A549/hIGF-I) was obtained.

(2) Determination of hIGF-I Produced in a Culture Supernatant of A549/hIGF-I Cell The following test was carried out in order to verify whether the introduced hIGF-I gene is expressed in the A549/hIGF-I cell prepared in above (1) and said cell is producing hIGF-I.

The A549/hIGF-I cell or A549 cell was cultured in the RPMI medium, and then the culture supernatant was recovered to measure the amount of hIGF-I contained in the culture supernatant by ELISA method as follows.

The methylated BSA-hIGF-I-immobilized plate shown in Reference Example 1(4) was prepared, an hIGF-I solution prepared by 5-fold serial dilution starting from 2 μg/ml as the positive sample, or a culture supernatant of A549/hIGF-I or A549 cell, was dispensed at 25 μl/well, and then purified antibody of the anti-hIGF antibody KM1468 diluted to 0.6 μg/ml was dispensed, mixed and reacted at room temperature for 2 hours. After the reaction and subsequent washing with Tween-PBS, 1000 times-diluted peroxidase-labeled rabbit anti-rat Ig antibody (manufactured by DAKO) was dispensed at 50 μl/well and reacted at room temperature for 1 hour. After the reaction and subsequent washing with Tween-PBS, 1000 times-diluted anti-rat IgG-HRP (manufactured by DAKO) was dispensed at 50 μl/well and reacted at room temperature for 1 hour. After the reaction and subsequent 5 times of washing with Tween-PBS, an ABTS substrate solution [a solution prepared by dissolving 0.55 g of 2,2′-azinobis(3-ethylbenzothiazoline-6-sulfonic acid) ammonium salt in 1 liter of 0.1 M citrate buffer (pH 4.2), and further adding thereto 1 μl/ml of hydrogen peroxide just before use] was added at 50 μl/well to effect color development, and then OD415 was measured using the plate reader Emax.

The results are shown in FIG. 11. As shown in FIG. 11A, in comparison with the culture supernatant of A549 cell to which with the hIGF-I gene was not introduced, the binding activity was distinctively reduced in the culture supernatant of A549/hIGF-I cell to which the hIGF-I gene was introduced, thus showing that the A549/hIGF-I cell expresses hIGF-I.

(3) Influence of Anti-hIGF Rat Monoclonal KM1468 on the Proliferation of hIGF-I Expressing Cell Whether the KM1468 can inhibit a cell growth dependent on hIGF-I produced by the cell itself (hereinafter referred to as autocrine cell proliferation) was examined using the hIGF-I gene-introduced cell A549/hIGF-I cell prepared in above (1).

The A549/hIGF-I cell or A549 cell was cultured using RPMI 1640 medium (manufactured by Invitrogen) containing 10% FCS and 50 μg/ml gentamicin (manufactured by Nakalai Tesque) (hereinafter referred to as RPMI medium), and then respectively suspended in DMEM/F12 medium (-FCS, -Phenol red) (manufactured by Invitrogen) containing 10 μg/ml human transferrin (manufactured by GIBCO) and 200 μg/ml BSA (manufactured by Invitrogen) (hereinafter referred to as serum-free medium) to give a cell density of $2 \times 10^5$ cells/ml.

Cell suspension of the A549/hIGF-I cell or A549 cell was dispensed at 100 μl/well on a 96 well plate (manufactured by Sumilon), the anti-hIGF antibody KM1468 serially diluted with the serum-free medium by 5-fold dilution starting from 200 μg/ml was added at 100 μl/well to each well, and then the cells were cultured at 37° C. for 5 days in a 5% $CO_2$ incubator. After the culturing, a cell proliferation reagent WST-1 (manufactured by Roche) was dispensed at 20 μl/well, the cells were further cultured at 37° C. for 4 hours in the 5% $CO_2$ incubator, and then the absorbance at OD450 nm (hereinafter referred to as OD450) was measured using a plate reader Emax (manufactured by Molecular Devices).

The results are shown in FIG. 13. The abscissa shows concentration of the anti-hIGF antibody KM1468 in each well at the time of the culturing. Proliferation of the A549/hIGF-I cell in the absence of the anti-hIGF antibody KM1468 shown by broken line was evidently increased in comparison with the growth of A549 cell shown by solid line which does not produce hIGF-I. This shows an autocrine growth in which the A549/hIGF-I cell prompts growth of the A549/hIGF-I cell itself by the self-produced hIGF-I. Such an autocrine proliferation shown in FIG. 13 was dose-dependently inhibited when the antibody KM1468 was added at the time of the culturing of A549/hIGF-I cell. On the other hand, the antibody KM1468 did not exert influence upon the growth of A549 cell. That is, it was shown that the anti-hIGF antibody KM1468 can inhibit the autocrine cell proliferation by the hIGF-I produced by the cell itself.

(4) Influence of Anti-hIGF Antibody KM1468 Upon Anchorage Independent Proliferation of hIGF-I Expressing Cell Cells after malignant alteration have the ability to perform anchorage independent proliferation in which they can grow regardless of a suspended condition with no cell engraftment, such as in a soft agar. The ability to perform anchorage independent proliferation is very closely related to the tumorigenicity of cells, and it is considered that hIGF-I is concerned therein. Whether the KM1468 can inhibit anchorage independent proliferation of a cell was examined in the following manner using the A549/hIGF-I cell prepared in above (1).

RPMI medium containing warmed 0.3% agar noble (manufactured by Difco) (hereinafter referred to as agar-RPMI medium) was dispensed at 1 ml/well on a 12 well plate (manufactured by Costar), and left the medium at room temperature for scores of minutes to effect gelation. After culturing the A549/hIGF-I cell or A549 cell using the RPMI medium, the resulting cells were suspended in warmed agar-RPMI medium to give a cell density of $1 \times 10^3$ cells/ml.

The cell suspension of A549/hIGF-I cell or A549 cell was overlaid on each well at 1 ml/well. After leaving at room temperature for several minutes to effect gelation, the cells were cultured at 37° C. for 4 weeks in a 5% $CO_2$ incubator. After the culturing, the number of colonies formed in each well was counted under a microscope.

The results are shown in FIG. 14. As shown in FIG. 14, the anchorage independent cell proliferation of the A549/hIGF-I cell producing hIGF-I was increased in comparison with the anchorage independent cell proliferation of the A549 cell. In addition, when 10 μg/ml of the anti-hIGF antibody KM1468 was added during culturing of A549/hIGF-I cell in the soft agar, the anchorage independent cell proliferaton was completely inhibited by the addition of KM1468. That is, it was shown that hIGF-I is concerned in the anchorage independent cell proliferation, and the hIGF-dependent anchorage independent cell proliferation is inhibited by the anti-hIGF antibody KM1468.

(5) Tumor Growth Inhibitory Effect of Anti-hIGF Antibody KM1468 Upon hIGF-I Expressing Cell Using the A549/hIGF-I cell prepared in above (1), tumor growth inhibitory effect of the anti-hIGF antibody KM1468 was examined in the in vivo tumor formation in which hIGF-I takes a role according to the following manner.

The A549/hIGF-I cell or A549 cell was cultured using the RPMI medium and then respectively suspended in PBS to give a cell density of $1 \times 10^6$ cells/ml.

A 100 μl of the cell suspension of A549/hIGF-I cell or A549 cell was subcutaneously grafted into the right thoracic region of each nude mouse Balb/c Ajc-1 nu (female) of 6-weeks-old. The number of transplanted cells per one mouse becomes $1 \times 10^7$ cells. Starting just after the transplantation, 500 μg per one mouse of the anti-hIGF antibody KM1468 was administered through the tail vein twice a week, 8 times in total. As a negative control, PBS was simultaneously administered to on the same subcutaneous tumor transplantation mouse. Five days after the cell grafting, tumor volume was measured. The tumor volume (mm$^3$) was calculated from the length, breadth and height of the tumor using a formula of length×breadth×height×0.5236.

The results are shown in FIG. 15. When growth of the subcutaneous tumor in the mouse grafted with the A549 cell which does not produce hIGF-I was compared with that of the mouse grafted with the A549/hIGF-I cell which produces hIGF-I, growth of the tumor was increased in the case of the subcutaneous tumor in the mouse grafted with the A549/hIGF-I cell. In addition, in the mouse grafted with the A549/hIGF-I cell, growth of the subcutaneous tumor was significantly inhibited when the anti-hIGF antibody KM1468 was administered. This result distinctively shows that the anti-hIGF antibody KM1468 inhibits growth of tumor also in vivo due to inhibition of hIGF-I.

Reference Example 5

Gene Cloning of Anti-hIGF Antibody KM1468 cDNA encoding the V region of anti-hIGF rat monoclonal KM1468 was isolated and analyzed as follows.

(1) Preparation of mRNA from Anti-hIGF Antibody KM1468 Producing Hybridoma

A 27 μg of KM1468-derived mRNA was prepared from $5 \times 10^7$ cells of an anti-hIGF antibody KM1468 producing hybridoma KM1468 (FERM BP-7978) using an mRNA preparation kit Fast Track mRNA Isolation Kit (manufactured by Invitrogen) in accordance with the instructions attached thereto.

(2) Preparation of H Chain and L Chain cDNA Libraries of Anti-hIGF Antibody KM1468

A cDNA having an EcoRI-NotI adapter sequence on both terminal was synthesized from 5 μg of the KM1468 mRNA prepared in above (1) using TimeSaver cDNA Synthesis Kit (manufactured by Amersham Pharmacia) in accordance with the instructions attached thereto. Total amount of the synthesized cDNA was dissolved in 20 μl of sterile water and then fractionated by an agarose gel electrophoresis, and a cDNA fragment of about 1.5 kb corresponding to the H chain of an IgG class antibody and cDNA fragment of about 1.0 kb corresponding to the L chain of a κ class were recovered in an amount of about 1.0 μg respectively using QIAquick Gel Extraction Kit (manufactured by QIAGEN). Next, using λZAPII Predigested EcoRI/CIAP-Treated Vector Kit (manufactured by Stratagene), each of 0.1 μg of the cDNA fragment of about 1.5 kb and 0.1 μg of the cDNA fragment of about 1.0 kb was ligated to 1 μg of λZAPII vector whose termini had been dephosphorylated with Calf Intestine Alkaline Phosphatase after digestion with a restriction enzyme EcoRI attached to the kit, in accordance with the instructions attached thereto. After the ligation, a 2.5 μl of each reaction solution was packaged into λ phage using Gigapack III Gold Packaging Extracts (manufactured by Stratagene) in accordance with the instructions attached thereto to thereby obtaining $5.0 \times 10^4$ phage clones as an H chain cDNA library of KM1468, and $4.0 \times 10^4$ phage clones as an L chain cDNA library. Next, each phage was immobilized on a nylon membrane filter Hybond-N$^+$ (manufactured by Amersham Pharmacia) in accordance with a conventional method (Molecular Cloning: A Laboratory Manual, Cold Spring Harbor Lab. Press New York, 1989).

(3) cDNA Cloning for the H Chain and L Chain of Anti-hIGF Rat Monoclonal KM1468

The nylon membrane filters of H chain cDNA library and L chain cDNA library of KM1468 prepared in Example 5 (1-2) were detected using a cDNA of the C region of a mouse antibody [H chain is a fragment of mouse Cγ2b cDNA (Nature, 283, 786, 1980), and L chain is a fragment of mouse Cκ cDNA (Cell, 22, 197, 1980)] as the probe using ECL Direct Nucleic Acid Labeling and Detection Systems (manufactured by Amersham-Pharmacia) in accordance with the instructions attached thereto, and each 10 phage clones strongly hybridized to the probe were obtained for each of the H chain and L chain. Next, each phage clone was converted into plasmid by the in vivo excision method in accordance with the instructions of λZAPII Predigested EcoRI/CIAP-Treated Vector Kit (manufactured by Stratagene). Nucleotide sequence of cDNA contained in the obtained plasmid was determined by carrying out the reaction using BigDye Terminator Cycle Sequencing FS Ready Reaction Kit (manufactured by Applied Biosystems) in accordance with the instructions attached thereto, and using a nucleotide sequence automatic analyzer ABI PRISM 377 (manufactured by Applied Biosystems). As a result, a plasmid pKM1468H5-2 containing the full length of functional H chain cDNA and a plasmid pKM1468L5-1 containing the full length of functional L chain cDNA, in which an ATG sequence considered to be the initiation codon is present in the 5'-terminals of respective cDNA, were obtained.

(4) Analysis of V Region Amino Acid Sequences of Anti-hIGF Antibody KM1468

The full length nucleotide sequence of VH of KM1468 contained in the plasmid pKM1468H5-2 is shown in SEQ ID NO:1 and full length amino acid sequence of VH of KM1468 deduced therefrom is shown in SEQ ID NO:2, and full length nucleotide sequence of VL of KM1468 contained in the plasmid pKM1468L5-1 is shown in SEQ ID NO:3 and full length amino acid sequence of VL of KM1468 deduced therefrom is shown in SEQ ID NO:4, respectively. In this connection, there are a large number of nucleotide sequences respectively corresponding to the amino acid sequences shown by SEQ ID NOS:2 and 4, other than those shown by SEQ ID NOS:1 and 3, and all of them are included in the scope of the present invention. Based on the comparison with known sequence data of antibodies (Sequences of Proteins of Immunological Interest, US Dept. Health and Human Services, 1991) and or the comparison with results of the analysis of N-terminal amino acid sequences of VH and VL of the purified anti-hIGF antibody KM1468 using a protein sequencer PPSQ-10 (manufactured by Shimadzu), it was revealed that the isolated respective cDNA is a secretion signal sequence-containing full length cDNA encoding the H chain or L chain of the anti-hIGF antibody KM1468, and a sequence of from the 1st to 19th positions of the amino acid sequence shown by SEQ ID NO:2 is the secretion signal sequence of VH, and a sequence of from the 1st to 22nd positions of the amino acid sequence shown by SEQ ID NO:4 is the secration signal sequense of VL.

Next, novelty of the VH and VL amino acid sequences of the anti-hIGF antibody KM1468 was examined. Using GCG Package (version 10.0, manufactured by Genetics Computer Group) as a sequence analyzing system, the existing protein amino acid sequence data bases [SWISS-PROT (Release 39.0), PIR-Protein (Release 65.0)] were searched by the BLAST method (Journal of Molecular Biology, 215, 403-410, 1990). As a result, completely coincided sequences were not found for both VH and VL, and it was confirmed that the VH and VL of the anti-hIGF antibody KM1468 are novel amino acid sequences.

In addition, CDRs of the VH and VL of the anti-hIGF antibody KM1468 were identified by comparing with amino acid sequences of known antibodies. Amino acid sequences of CDR1, 2 and 3 of the VH of KM1468 are shown in SEQ ID NOS: 5, 6 and 7, and amino acid sequences of CDR1, 2 and 3 of the VL in SEQ ID NOS: 8, 9 and 10, respectively.

Reference Example 6

Preparation of Anti-hIGF Human Chimeric Antibody (2) Construction of Human Chimeric Antibody Expression Vector An anti-hIGF-I chimeric antibody expression vector derived from the anti-hIGF antibody KM1468 was constructed in the following manner using the vector for expression of humanized antibody pKANTEX93 described in WO 97/10354 which can express the human IgG1, κ class antibodies and the plasmids obtained in Reference Example 5 (3) containing cDNAs for the H chain and L chain of KM1468.

Firstly, in order to insert the cDNAs for the VH and VL of KM1468 into the expression vector pKANTEX93 such that the amino acid sequences are not changed, cDNAs for the VH and VL of KM1468 were reconstructed by PCR. As the primers, synthetic DNAs respectively having the nucleotide sequences of SEQ ID NOS:68 and 69 were designed for the VH cDNA, and synthetic DNAs respectively having the nucleotide sequences of SEQ ID NOS:70 and 71 were designed for the VL cDNA. Each of the synthetic DNAs contains a restriction enzyme recognizing sequence in the 5'-terminal for its cloning into pKANTEX93. Specifically, 20 ng of the plasmid pKM1468H5-2 obtained in Reference Example 5 (3) was added to a buffer solution containing 50 µl of KOD DNA Polymerase-attached PCR Buffer #1 (manufactured by TOYOBO), 0.2 mM dNTPs, 1 mM magnesium chloride and 0.5 µM of the synthetic DNAs having the nucleotide sequences shown in SEQ ID NOS:68 and 69, and using a DNA thermal cycler GeneAmp PCR System 9600 (manufactured by PERKIN ELMER), the mixture was heated at 94° C. for 3 minutes, to which 2.5 units of KOD DNA Polymerase (manufactured by TOYOBO) was added, and a cycle of 15 seconds at 98° C., 2 seconds at 65° C. and 30 seconds at 74° C. was repeated 25 cycles. In the same manner, another PCR was carried out by the same method described in the above, by adding 20 ng of the plasmid pKM1468L5-1 obtained in Reference Example 5 (3) to a buffer solution containing 50 µl of KOD DNA Polymerase-attached PCR Buffer #1 (manufactured by TOYOBO), 0.2 mM dNTPs, 1 mM magnesium chloride and 0.5 µM of the synthetic DNA fragments having the nucleotide sequences shown in SEQ ID NOS:70 and 71. A 10 µl portion of each reaction solution was subjected to an agarose gel electrophoresis, and then a PCR product of about 0.5 kb for VH or a PCR product of about 0.43 kb for VL was recovered using QIAquick Gel Extraction Kit (manufactured By QIAGEN).

Next, 0.1 µg of DNA obtained by digesting the plasmid pBluescript II SK(−) (manufactured by Stratagene) with the restriction enzyme SmaI (manufactured by Takara Shuzo) and then dephosphorylating the termini with Calf Intestine Alkaline Phosphatase (hereinafter referred to as CIAP hereinafter; manufactured by Takara Shuzo) and 0.1 µg of each PCR product obtained in the above were prepared into 7.5 µl by adding sterile water and then left at 22° C. overnight after adding 7.5 µl of the solution I of TaKaRa DNA Ligation Kit Ver. 2 (manufactured by Takara Shuzo) and 0.3 µl of the restriction enzyme SmaI (manufactured by Takara Shuzo). Using the recombinant plasmid DNA solution obtained in this manner, an *Escherichia coli* DH5α (manufactured by TOYOBO) was transformed. Each plasmid DNA was prepared from the transformants, its nucleotide sequence was determined by carrying out the reaction using BigDye Terminator Cycle Sequencing FS Ready Reaction Kit (manufactured by Applied Biosystems) in accordance with the instructions attached thereto and using a nucleotide sequence automatic analyzer ABI PRISM 377 (manufactured by Applied Biosystems). In this manner, plasmids pKM1468VH and pKM1468VL having the nucleotide sequences of interest shown in FIG. 16 were obtained.

Next, a plasmid pKANTEX1468H shown in FIG. 17 was constructed by inserting the restriction enzyme fragment (NotI-ApaI) containing the VH cDNA of pKM1468VH obtained in the above into the NotI-ApaI site of the vector pKANTEX93 for expression of humanized antibody. Also, a plasmid pKANTEX1468Chi shown in FIG. 17 was constructed by inserting the restriction enzyme fragment (EcoRI- BsiWI) containing the VL cDNA of pKM1468VL obtained in the above into the EcoRI-BsiWI site of the plasmid pKANTEX1468H. Using the plasmid pKANTEX1468Chi, nucleotide sequences of the VH and VL cDNA molecules were determined by carrying out the reaction using BigDye Terminator Cycle Sequencing FS Ready Reaction Kit (manufactured by Applied Biosystems) in accordance with the instructions attached thereto and using the nucleotide sequence automatic analyzer ABI PRISM 377 (manufactured by Applied Biosystems), and it was confirmed as a result that plasmids cloned with the VH and VL cDNAs of interest were obtained.

(3) Stable expression of Anti-hIGF Human Chimeric Antibody Using Animal Cell

Using the anti-hIGF chimeric antibody expression vector pKANTEX1468Chi obtained in above (2), expression of the anti-hIGF human chimeric antibody in an animal cell was carried out in the following manner.

The plasmid pKANTEX1468Chi was digested with a restriction enzyme AatII (manufactured by TOYOBO) to linearize, a 10 μg portion thereof was introduced into $4 \times 10^6$ cells of a rat myeloma cell line YB2/0 (ATCC CRL 1581) by the electroporation method (Cytotechnology, 3, 133-140, 1990), and then the cells were suspended in 40 ml of H-SFM (5) medium [H-SFM medium (manufactured by Gibco BRL) containing 5% FCS] and dispensed at 200 μl/well on a 96 well culture plate (manufactured by Sumitomo Bakelite). After 24 hours of culturing at 37° C. in a 5% $CO_2$ incubator, G418 was added thereto to a concentration of 0.5 mg/ml and further cultured for 1 to 2 weeks. Culture supernatants were recovered from the wells in which transformant colonies showing G418-resistance were formed and became confluent, and concentration of the anti-hIGF chimeric antibody in the supernatants was measured by the binding ELISA shown in the present Reference Example (5).

Regarding each of the transformants in wells in which expression of the anti-hIGF chimeric antibody was found in the culture supernatants, in order to increase antigen expression using of a dhfr gene amplification system, each of the transformants was suspended to give a density of 1 to $2 \times 10^5$ cells/ml in H-SFM(5) containing 0.5 mg/ml of G418 and 50 nM of methotrexate (hereinafter referred to as MTX, manufactured by SIGMA) which is an inhibitor of a dhfr gene product dihydrofolate reductase (hereinafter referred to as DHFR), and the suspension was dispensed at 1 ml on a 24 well culture plate (manufactured by Greiner). By culturing at 37° C. for 1 to 2 weeks in a 5% $CO_2$ incubator, transformants showing a resistance to 50 mM MTX were induced. When the transformants became confluent in wells, concentration of the anti-hIGF chimeric antibody in the culture supernatants was measured by the binding ELISA shown in the present Reference Example (5). The transformants in wells in which expression of the anti-hIGF chimeric antibody was found in the culture supernatants were then cultured in a medium containing 100 nM MTX by the same method described in the above, and the transformants obtained in the same manner were further cultured in a medium containing 200 nM to thereby finally obtain a transformant which can grow in the H-SFM(5) containing 0.5 mg/ml of G418 and 200 nM of MTX and can highly express the anti-hIGF chimeric antibody. By subjecting the transformant thus obtained to single cell cloning by limiting dilution method twice, a transformant having the highest expression of the anti-hIGF chimeric antibody was obtained. As the transformant producing the anti-hIGF chimeric antibody derived from KM1468, KM3002 can be cited. The transformant KM3002 was deposited on Apr. 2, 2002, as FERM BP-7996 in International Patent Organism Depositary, National Institute of Advanced Industrial Science and Technology (postal code 305-8566; Central 6, 1-1-1 Higashi, Tsukuba, Ibaraki, Japan).

(4) Purification of Anti-hIGF Chimeric Antibody from Culture Supernatant

The transformant KM3002 obtained in Reference Example 5(3) which expresses the anti-hIGF chimeric antibody was suspended in the H-SFM containing 0.5 mg/ml of G418, 200 nM of MTX and 5% of Daigo's GF21 (manufactured by Wako Pure Chemical Industries) to give a density of 1 to $2 \times 10^5$ cells/ml, and dispensed at 100 ml portions in 175 cm² flasks (manufactured by Greiner). The cells were cultured at 37° C. for 5 to 7 days in a 5% $CO_2$ incubator, and the culture supernatant was recovered when they became confluent. By purifying the anti-hIGF chimeric antibody KM3002 from about 1 liter of the culture supernatant using Prosep-A (manufactured by Bioprocessing) column in accordance with the instructions attached thereto, about 10.2 mg of purified protein was obtained. About 4 μg of the obtained anti-hIGF chimeric antibody KM3002 was subjected to an electrophoresis in accordance with a known method (Nature, 227, 680-685, 1970) to examine its molecular weight and purification degree. The results are shown in FIG. 18. From the purified anti-hIGF chimeric antibody KM3002, one band corresponding to a molecular weight of about 150 kilodaltons (hereinafter referred to as Kd) was observed under non-reducing condition, and two bands corresponding to about 50 Kd and about 25 Kd was obtained under reducing condition. These molecular weights coincided with the reports that the IgG class antibody has a molecular weight of about 150 Kd under non-reducing condition, and is degraded into the H chain having a molecular weight of about 50 Kd and the L chain having a molecular weight of about 25 Kd under reducing condition due to cutting of the intramolecular S—S bond (Antibodies: A Laboratory Manual, Cold Spring Harbor Laboratory, Chapter 14, 1988; Monoclonal Antibodies: Principles and Practice, Academic Press Limited, 1996), thus confirming that the anti-hIGF chimeric antibody KM3002 is expressed as an antibody molecule having proper structure. In addition, as a result of the analysis of N-terminal amino acid sequences of the H chain and L chain of the purified anti-hIGF chimeric antibody KM3002 using a protein sequencer PPSQ-10 (manufactured by Shimadzu), it was confirmed that they coincide with the N-terminal amino acid sequences of the H chain and L chain of the anti-hIGF antibody KM1468, (5) Reactivity of Anti-hIGF Chimeric Antibody KM3002 to hIGF Reactivity of the anti-hIGF rat antibody KM1468 and the anti-hIGF chimeric antibody KM3002 to hIGF-I was examined by the ELISA shown in Reference Example 1(4). In this case, however, concentration of the methylated BSA-hIGF-I immobilized on the ELISA plate was changed to 0.5 μg/ml, and 4000 fold-diluted peroxidase-labeled rabbit anti-rat Ig antibody (manufactured by DAKO) was used as the secondary antibody in the case of the rat antibody, and 1000 fold-diluted peroxidase-labeled mouse anti-human IgG1 antibody (manufactured by Southern Biotechnology) in the case of the chimeric antibody. As shown in FIG. 19, the anti-hIGF chimeric antibody KM3002 showed an antibody concentration-dependent binding activity to hIGF-I. In addition, it was suggested that its activity is equivalent to the anti-hIGF rat antibody KM1468, though it is difficult to compare directly because of the different secondary antibodies.

INDUSTRIAL APPLICABILITY

An object of the present invention is to provide a recombinant antibody or an antibody fragment thereof which specifically binds to human insulin-like growth factor-I (hereinafter referred to as hIGF-I) and human insulin-like growth factor-II (hereinafter referred to as hIGF-II) at the same degree to inhibit the biological activities of hIGF-I and hIGF-II, a transformant producing the antibody or the antibody fragment thereof, a process for producing the antibody or the antibody fragment thereof, and a medicament comprising the antibody or the antibody fragment thereof as the active ingredient therein.

BRIEF DESCRIPTION OF THE DRAWINGS

FIG. 3a shows the results of the anti-hIGF human chimeric antibody KM3002 as expressed in □; the results of the anti-hIGF CDR-grafted antibody CamHV0/LV0 as expressed in ○; the results of the anti-hIGF CDR-grafted antibody QAR/LV0 as expressed in Δ; the results of the anti-hIGF CDR-grafted antibody QGAR/LV0 as expressed in ■; and the results of the anti-hIGF CDR-grafted antibody CamHV0/NYPLL3A11 as expressed in ●, respectively; and FIG. 3b shows the results of the anti-hIGF human chimeric antibody KM3002 as expressed in □; the results of the anti-hIGF CDR-grafted antibody CamHV0/LV0 as expressed in ○; the results of the anti-hIGF CDR-grafted antibody QGAR/LV0 as expressed in ◊; the results of the anti-hIGF CDR-grafted antibody QGAR/NYPLL3A11 as expressed in Δ; the results of the anti-hIGF CDR-grafted antibody QGAR/PLDFT as expressed in ●; and the results of the anti-hIGF CDR-grafted antibody QGAR/PLLDFT as expressed in ■, respectively.

FIG. 4a shows the results in the presence of 10 ng/ml hIGF-I, and FIG. 4b shows the results in the presence of 20 ng/ml hIGF-II, respectively. The abscissa shows antibody concentration (μg/ml), and the ordinate shows the value of cell proliferation as absorbance (OD450 nm), respectively. In the drawings, solid line shows the baseline of cell proliferation in the presence of hIGF-I or hIGF-II and in the absence of antibody, and dotted line shows the baseline of cell proliferation in the absence of hIGF-I or hIGF-II and in the absence of antibody, respectively. The symbol □ shows the results of anti-hIGF human chimeric antibody KM3002; ○ shows the results of anti-hIGF CDR-grafted antibody CamHV0/LV0; Δ shows the results of anti-hIGF CDR-grafted antibody QAR/LV0; and ■ shows the results of anti-hIGF CDR-grafted antibody QGAR/LV0, respectively.

FIG. 5a shows the results in the presence of 10 ng/ml hIGF-I, and FIG. 5b shows the results in the presence of 20 ng/ml hIGF-II, respectively. The abscissa shows antibody concentration (μg/ml), and the ordinate shows the value of cell proliferation as absorbance (OD450 nm), respectively. In the drawings, solid line shows the baseline of cell proliferation in the presence of hIGF-I or hIGF-II and in the absence of antibody, and dotted line shows the baseline of cell proliferation in the absence of hIGF-I or hIGF-II and in the absence of antibody, respectively. The symbol □ shows the results of anti-hIGF human chimeric antibody KM3002; ○ shows the results of anti-hIGF CDR-grafted antibody CamHV0/LV0; Δ shows the results of anti-hIGF CDR-grafted antibody QGAR/LV0; ◊ shows the results of anti-hIGF CDR-grafted antibody CamHV0/NYPLL3A11; and ■ shows the results of anti-hIGF CDR-grafted antibody QGAR/NYPLL3A11, respectively.

FIG. 6a shows the results in the presence of 10 ng/ml hIGF-I, and FIG. 6b shows the results in the presence of 20 ng/ml hIGF-II), respectively. The abscissa shows antibody concentration (μg/ml), and the ordinate shows the value of cell proliferation as absorbance (OD450 nm), respectively. In the drawings, solid line shows the baseline of cell proliferation in the presence of hIGF-I or hIGF-II and in the absence of antibody, and dotted line shows the baseline of cell proliferation in the absence of hIGF-I or hIGF-II and in the absence of antibody, respectively. The symbol □ shows the results of anti-hIGF human chimeric antibody KM3002; ◊ shows the results of anti-hIGF CDR-grafted antibody QGAR/LV0; ■ shows the results of anti-hIGF CDR-grafted antibody QGAR/PLDFT: ● shows the results of anti-hIGF CDR-grafted antibody QGAR/PLLDFT; and ▲ shows the results of anti-hIGF CDR-grafted antibody QGAR/NYPLL3A11, respectively.

FIG. 9A shows the results of p1-18 as expressed in ●; the results of p24-35 as expressed in □; the results of p29-41 as expressed in ■; the results with p36-47 as expressed in Δ; the results of p61-70 as expressed in ◊; the results of p14-30 as expressed in ♦; and the results of p41-56 as expressed in X, respectively. FIG. 9B shows the results of hIGF-I as expressed in ○; the results of p41-56C as expressed in ●; the results of p52-70 as expressed in □; the results of p1-18 and p41-56C as expressed in ■; the results of p1-18 and p52-70 as expressed in Δ; the results of p41-56c and p52-70 as expressed in ▲; and the results of p1-18, p41-56C and p52-70 as expressed in ◊, respectively.

FIG. 10A shows inhibition by each factor upon binding of KM1468 to hIGF-I, and FIG. 10B shows upon binding of KM1468 to hIGF-II. The abscissa shows concentration of respective factors (μg/ml), and the ordinate shows binding activity (%) wherein the value with no addition of factors is defined as 100%. The symbol ■ shows the results of hIGF-I; ○ shows the results of hIGF-II; and Δ shows the results of human insulin, respectively.

FIG. 12A shows the inhibition by a recombinant hIGF-I protein. The abscissa shows the concentration of the added recombinant hIGF-I protein, and the ordinate shows the binding activity (OD415). Dotted line shows the results in the absence of the recombinant hIGF-I protein. FIG. 12B shows hIGF-I contained in the culture supernatant of A549 cell and A549/hIGF-I cell. Blank shows A549 cell, and mesh shows A549/hIGF-I cell, respectively.

Sequence Listing Free Text

Figure 1:
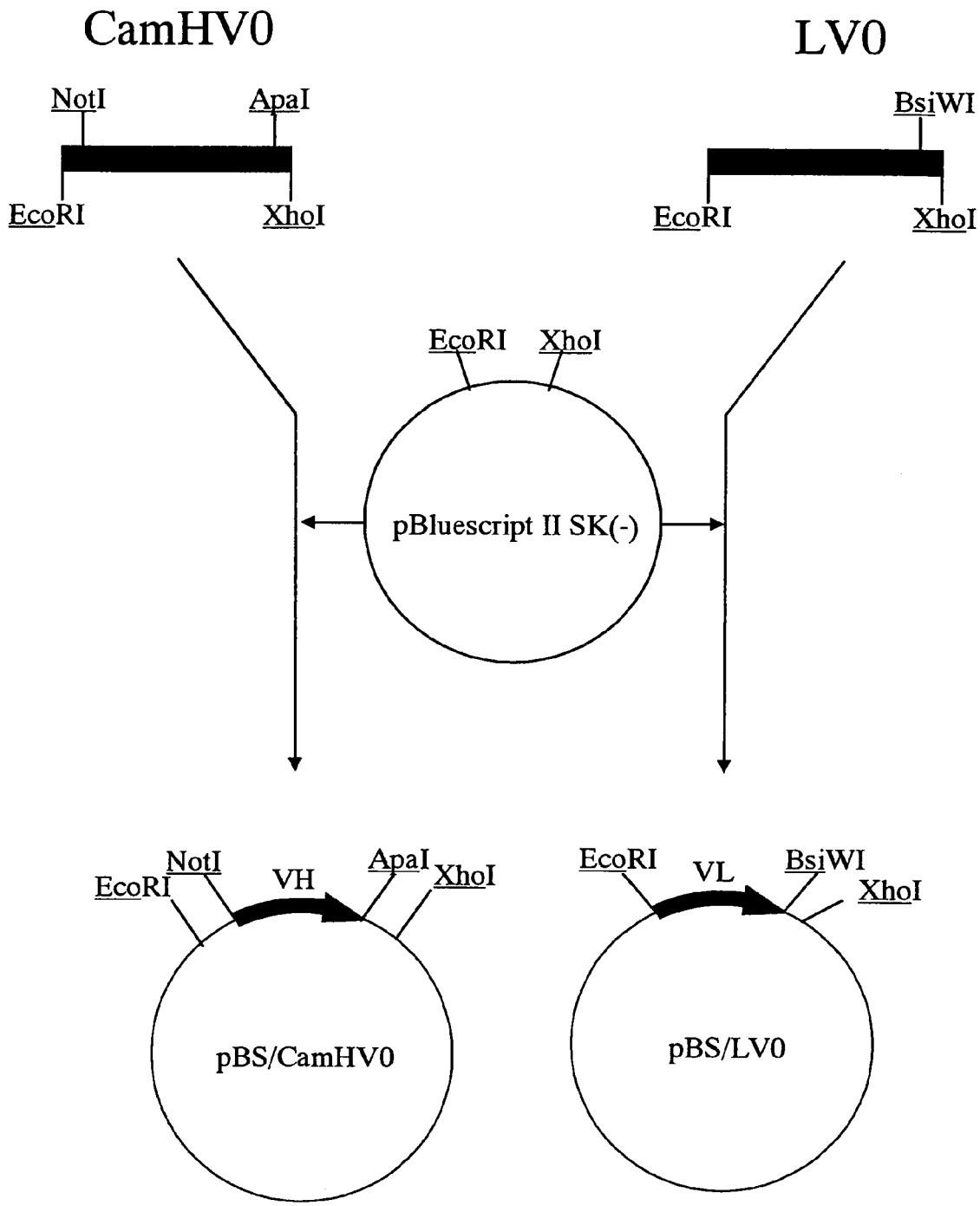
FIG. 1 shows the construction steps of plasmids pBS/CamHV0 and pBS/LV0.
Figure 2:
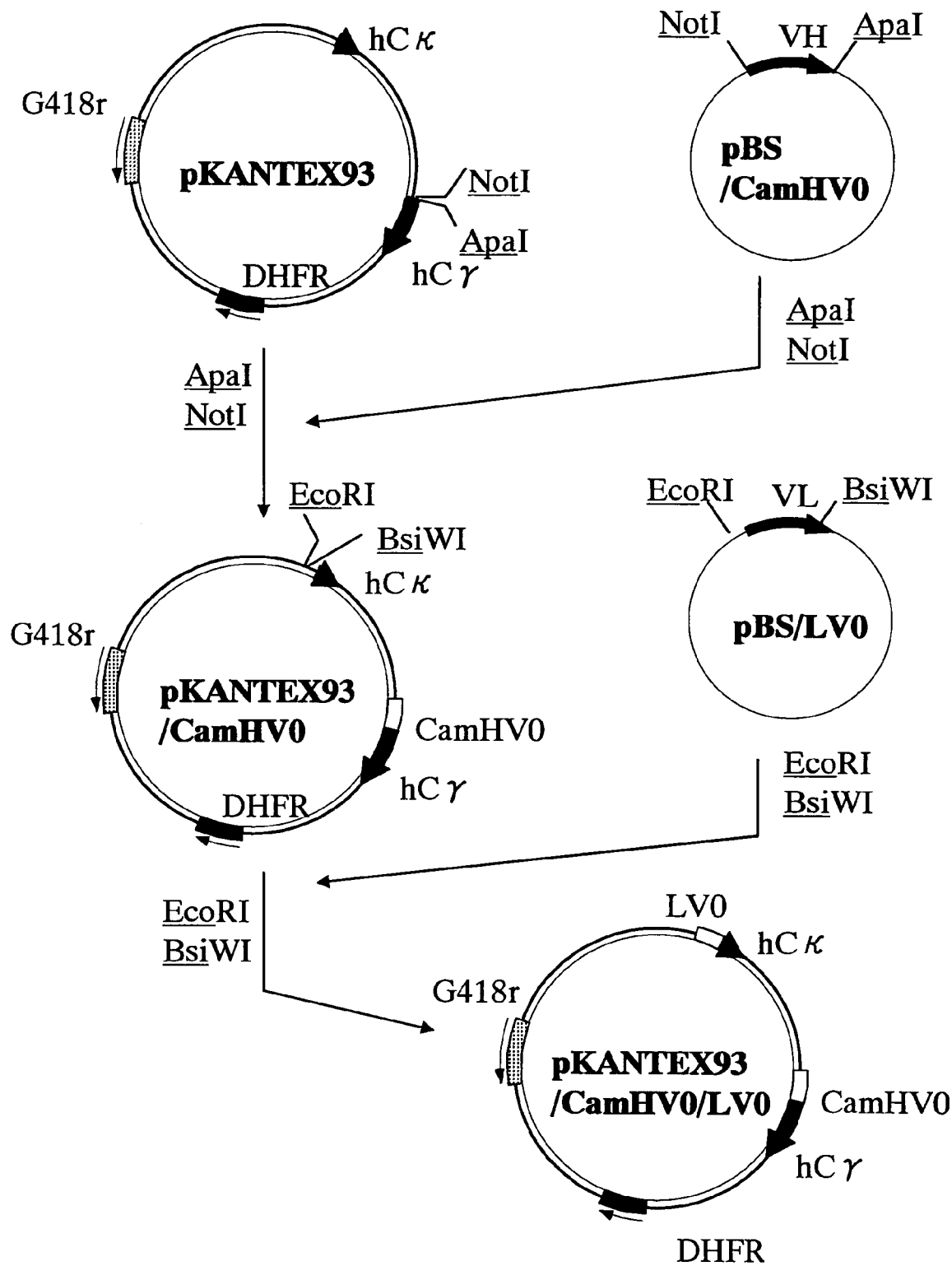
FIG. 2 shows the construction steps of a plasmid pKANTEX93/CamHV0/LV0.
Figure 3:
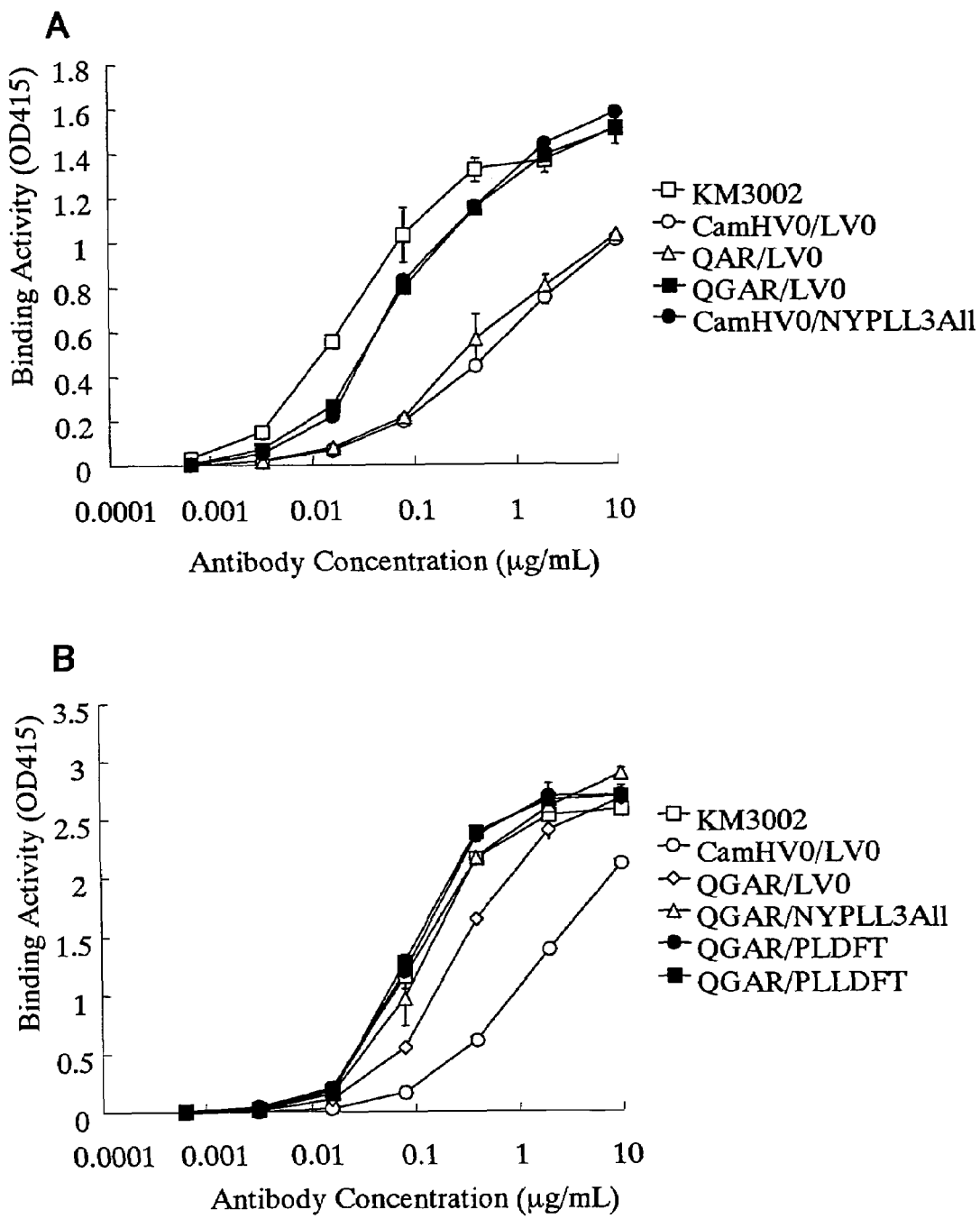
FIG. 3A-B shows the specific reactivity of anti-hIGF CDR-grafted antibody for hIGF-I (binding ELISA). The abscissa shows antibody concentration, and the ordinate shows binding activity as absorbance (415 nm).
Figure 4:
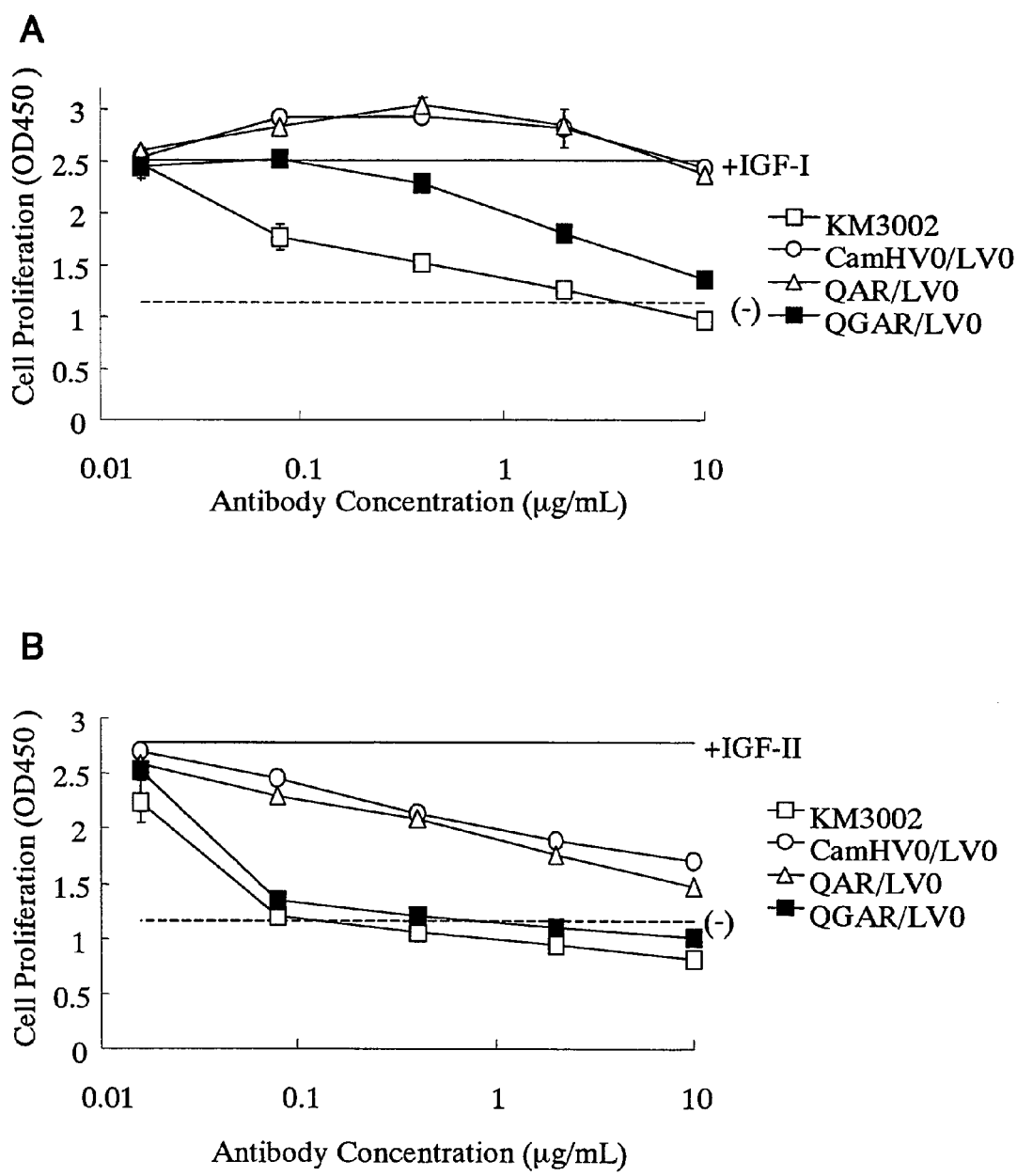
FIG. 4A-B shows the hIGF-I- or hIGF-II-dependent cell proliferation inhibitory effect of anti-hIGF CDR-grafted antibody.
Figure 5:
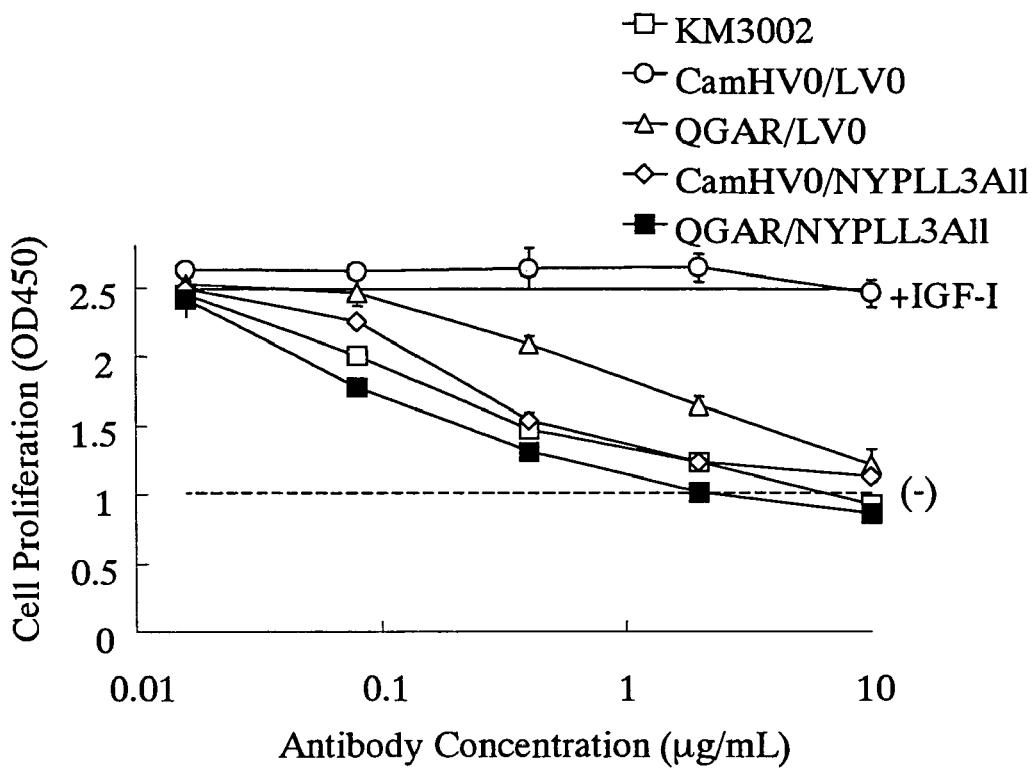
FIG. 5A-B shows the hIGF-I- or hIGF-II-dependent cell proliferation inhibitory effect of anti-hIGF CDR-grafted antibody.
Figure 5:
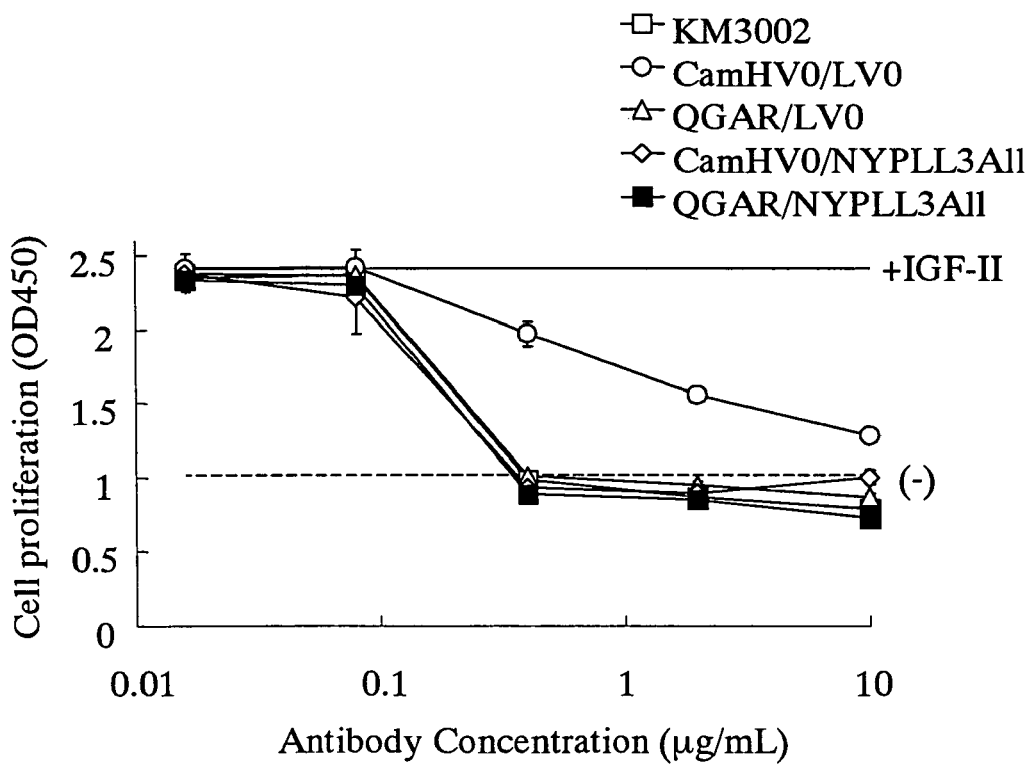
Figure 6:
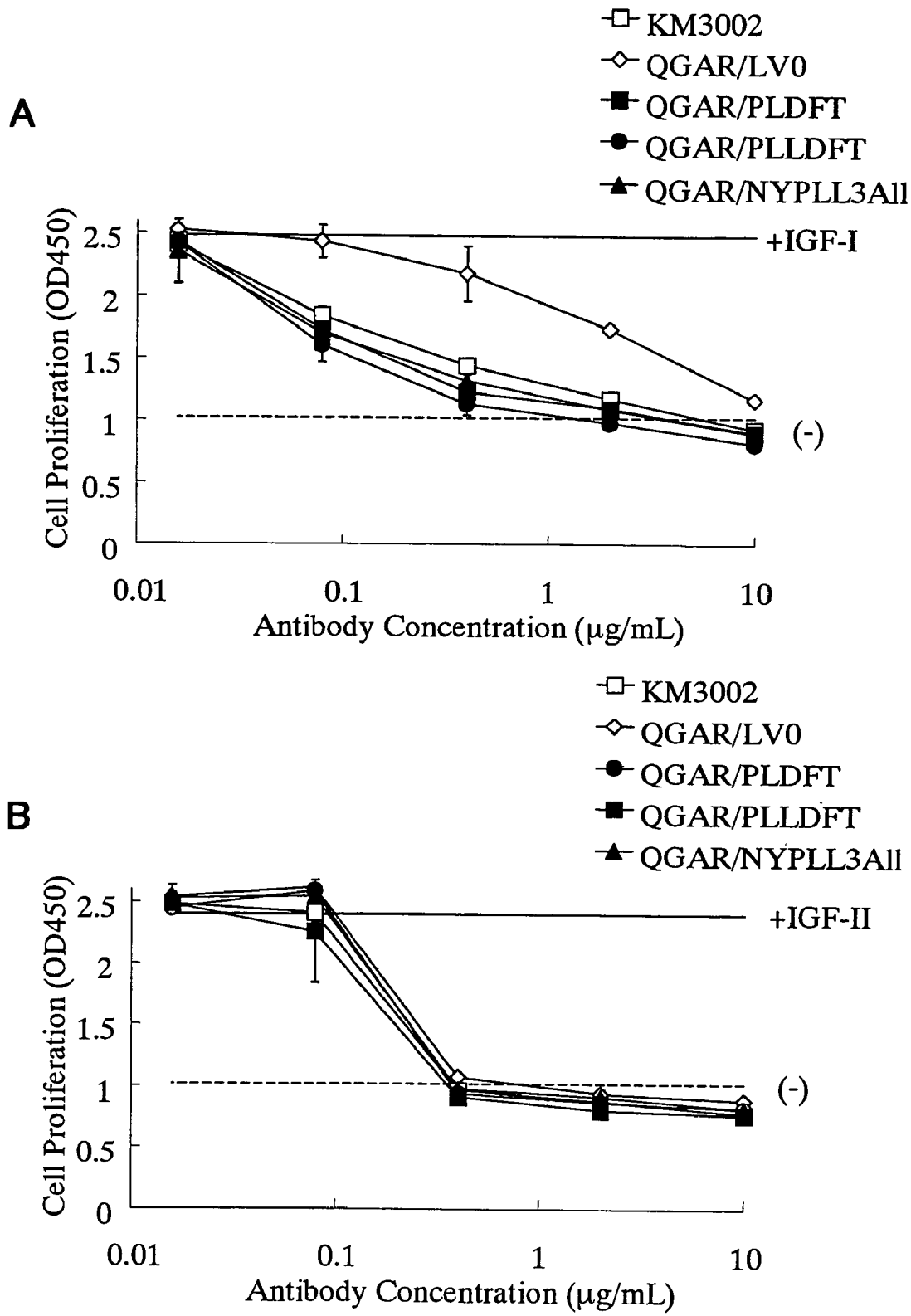
FIG. 6A-B shows the hIGF-I- or hIGF-II-dependent cell proliferation inhibitory effect of anti-hIGF CDR-grafted antibody.
Figure 7:
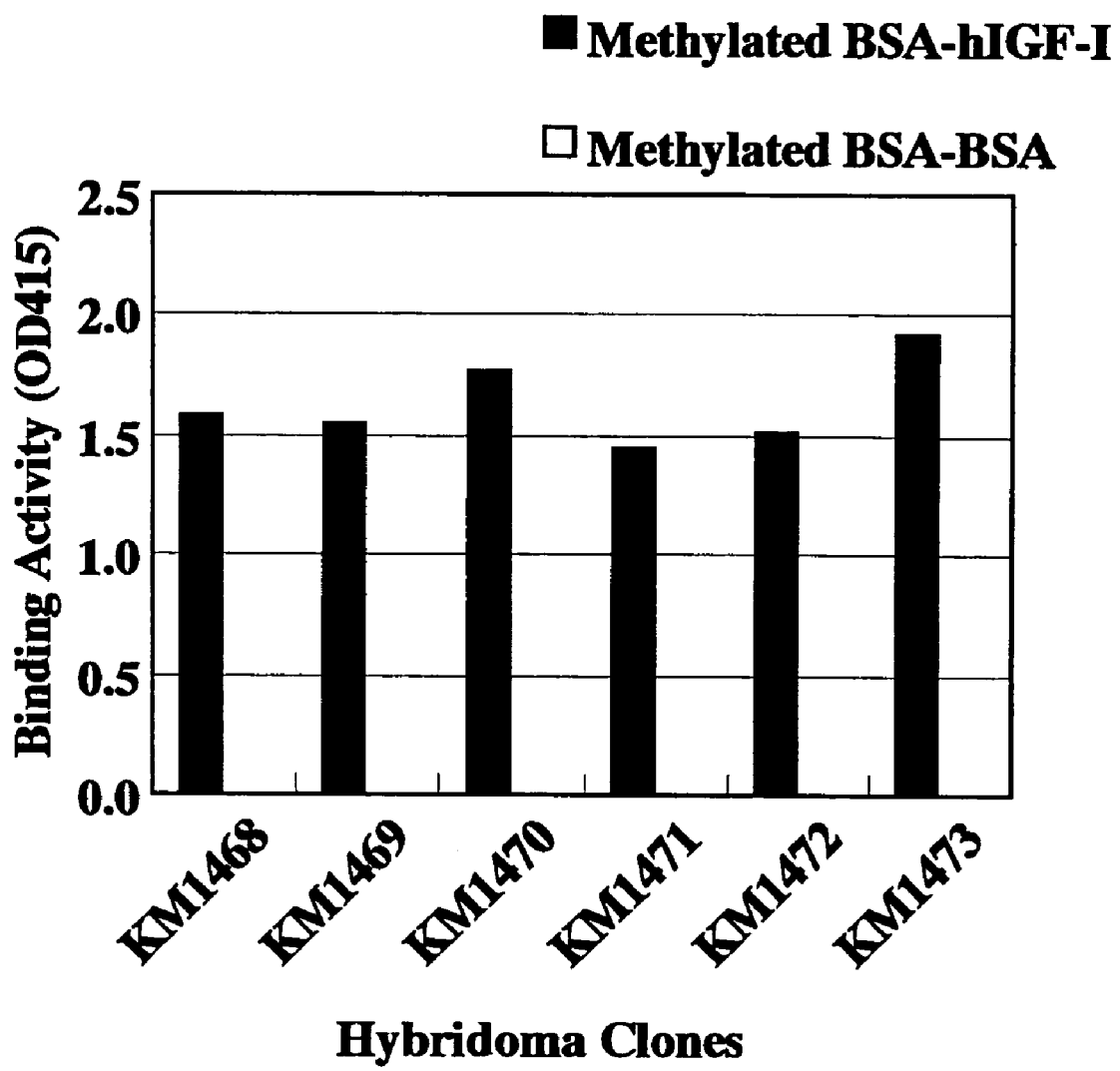
FIG. 7 shows specific reactivity of anti-hIGF rat monoclonal antibody for hIGF-I (binding ELISA). In the graph, solid bar shows the results of methylated BSA-hIGF-I as an antigen, and blank bar shows the results of methylated BSA-BSA as an antigen.
Figure 8:
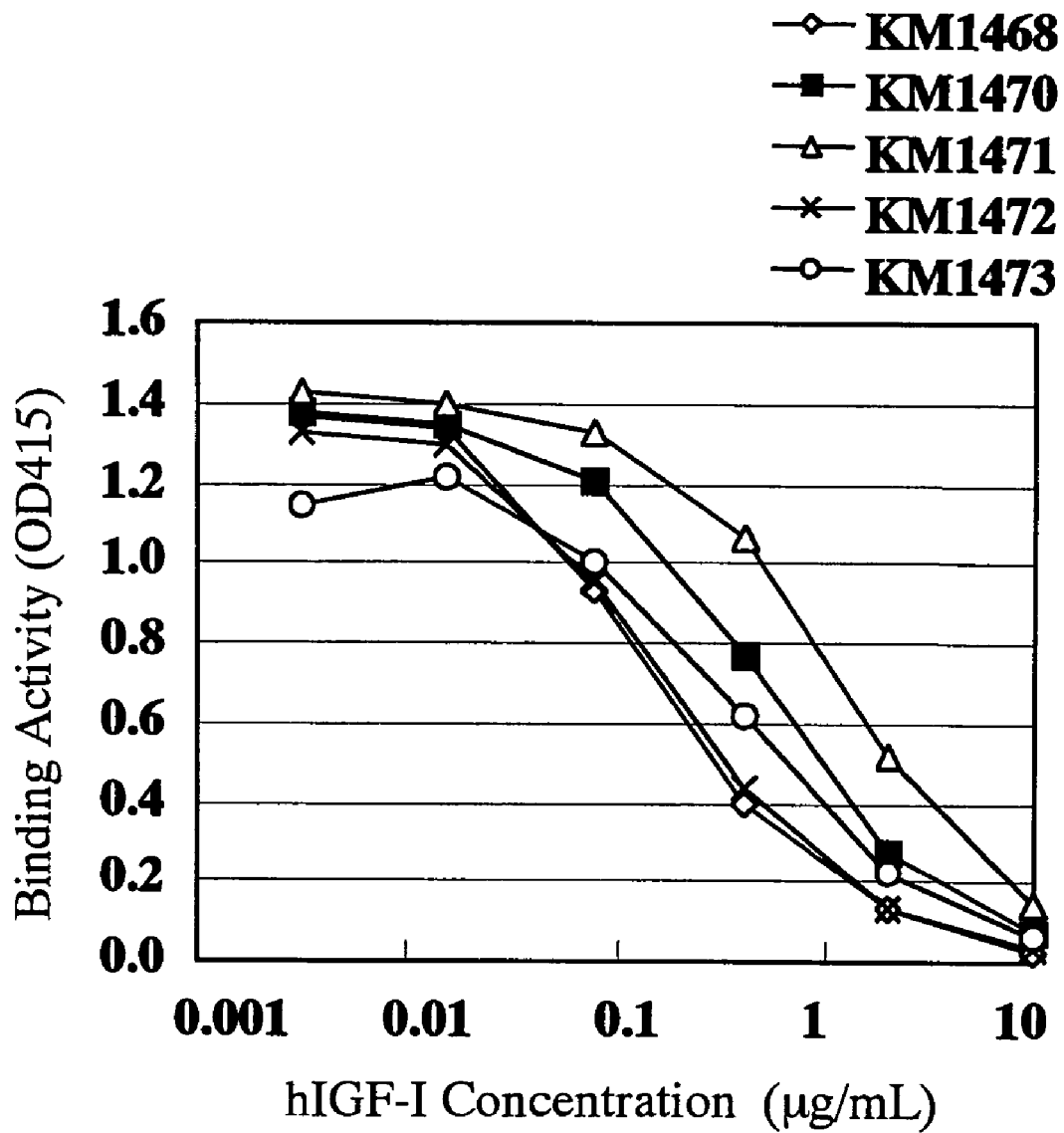
FIG. 8 shows reactivity of anti-hIGF rat monoclonal antibody for hIGF-I having authentic three-dimensional structure in a liquid system (competitive ELISA). The symbol ◊ shows the results with anti-hIGF rat monoclonal antibody KM1468; ■ shows the results of anti-hIGF rat monoclonal antibody KM1470; Δ shows the results of anti-hIGF rat monoclonal antibody KM1471; X shows the results of anti-hIGF rat monoclonal antibody KM1472; and ○ shows the results of anti-hIGF rat monoclonal antibody KM1473, respectively.
Figure 9:
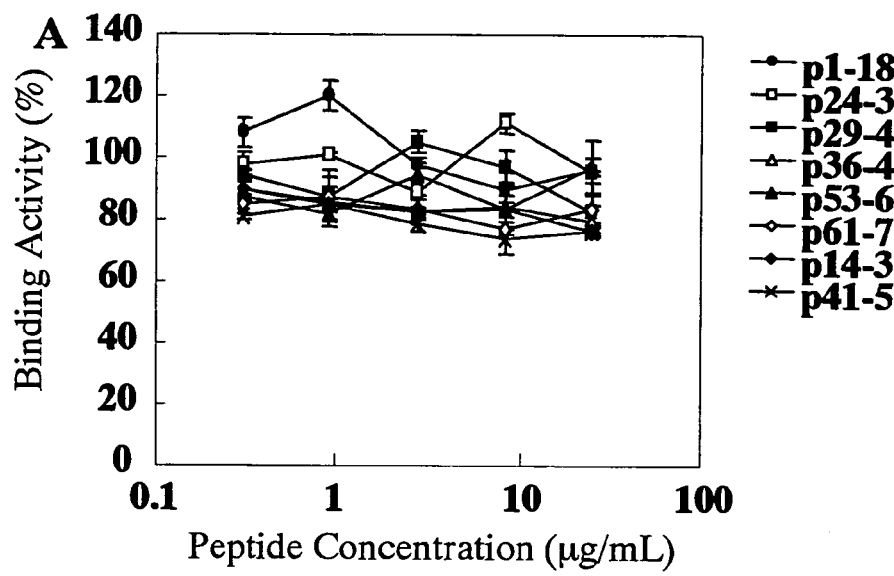
FIG. 9A-B shows activity of various peptides to inhibit binding of anti-hIGF rat monoclonal antibody KM1468 to hIGF-I. The abscissa shows concentration of each peptide (μg/ml), and the ordinate shows binding activity (%), respectively.
Figure 9:
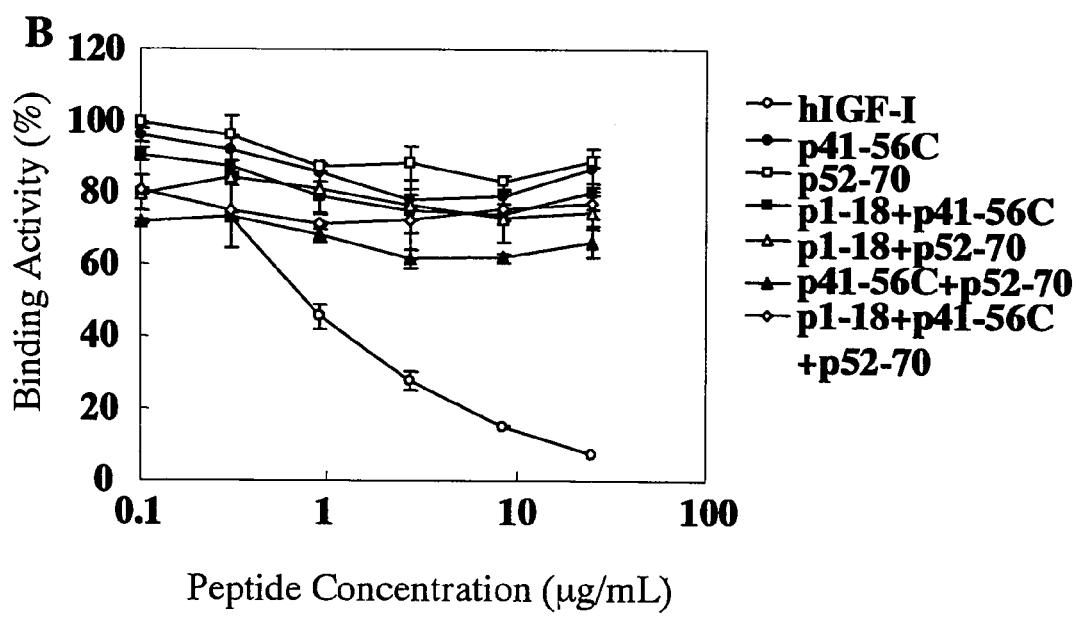
Figure 10:
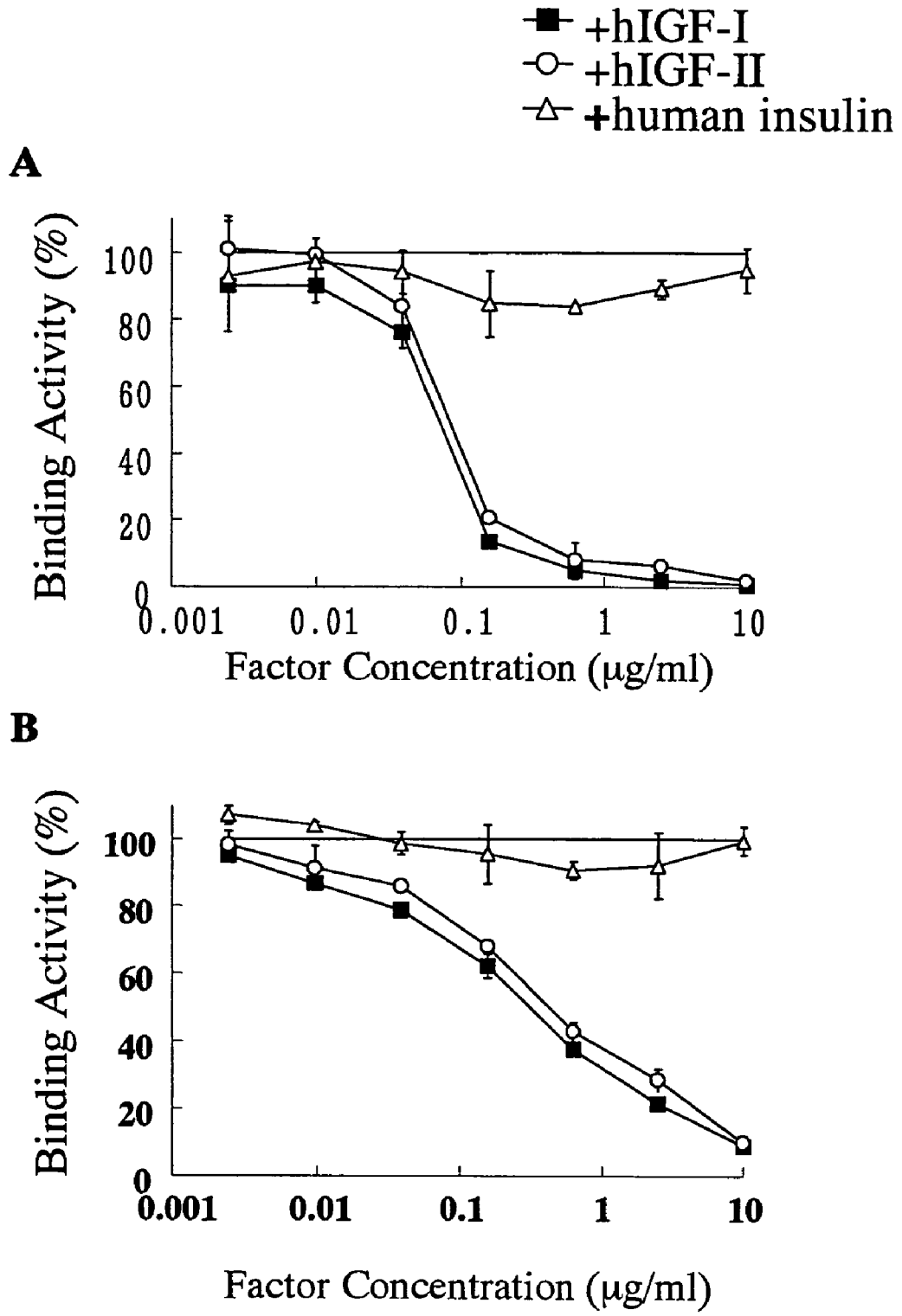
FIG. 10A-B shows activities of hIGF-I, hIGF-II and human insulin to inhibit binding of anti-hIGF antibody KM1468 to hIGF-I and hIGF-II.
Figure 11:
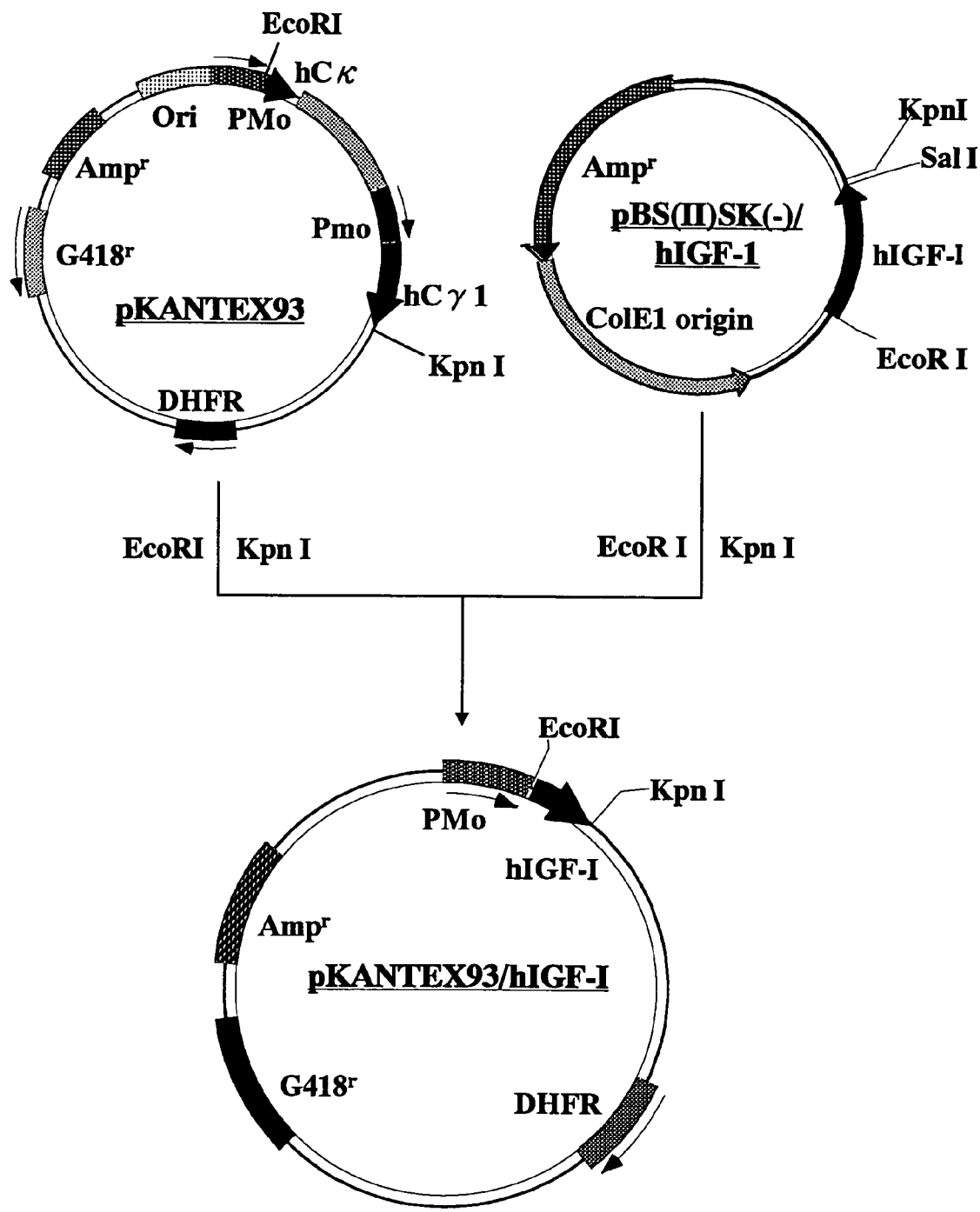
FIG. 11 shows the construction steps of plasmids pBS(II) SK(−)/hIGF-I and pKANTEX93/hIGF-I.
Figure 12:
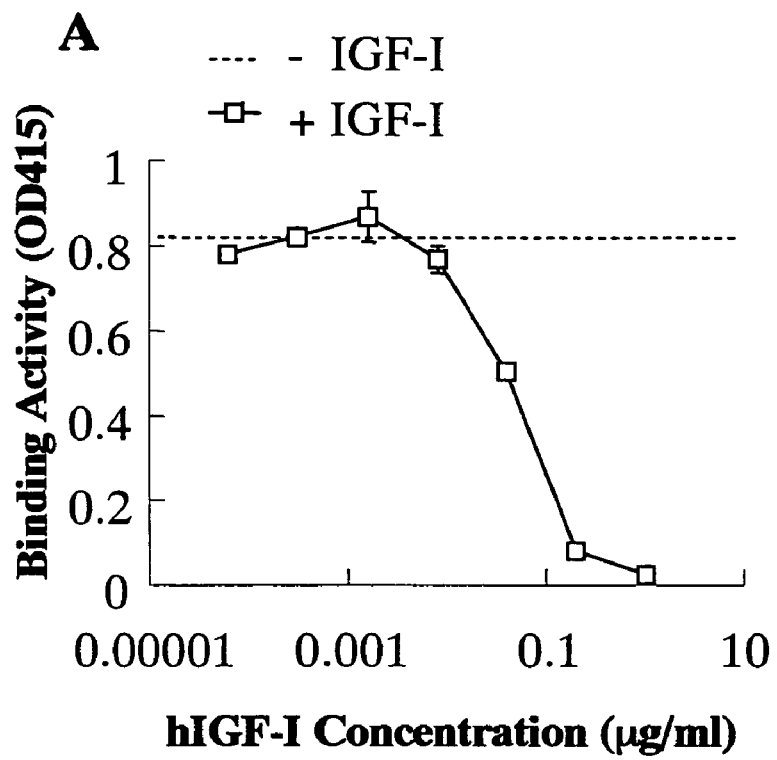
FIG. 12A-B shows the expression of hIGF-I in A549/hIGF-I cell.
Figure 12:
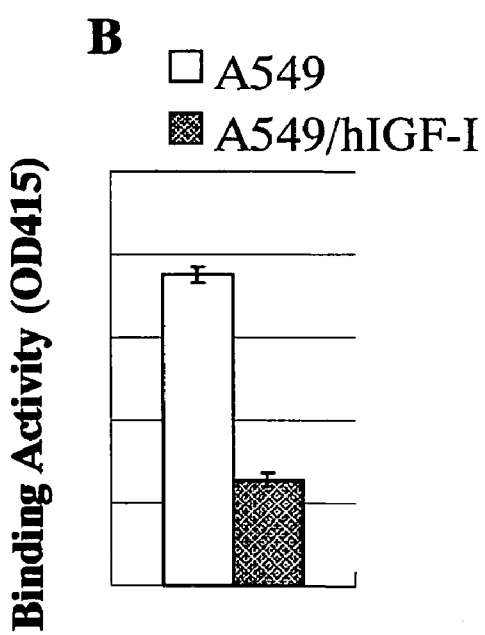
Figure 13:
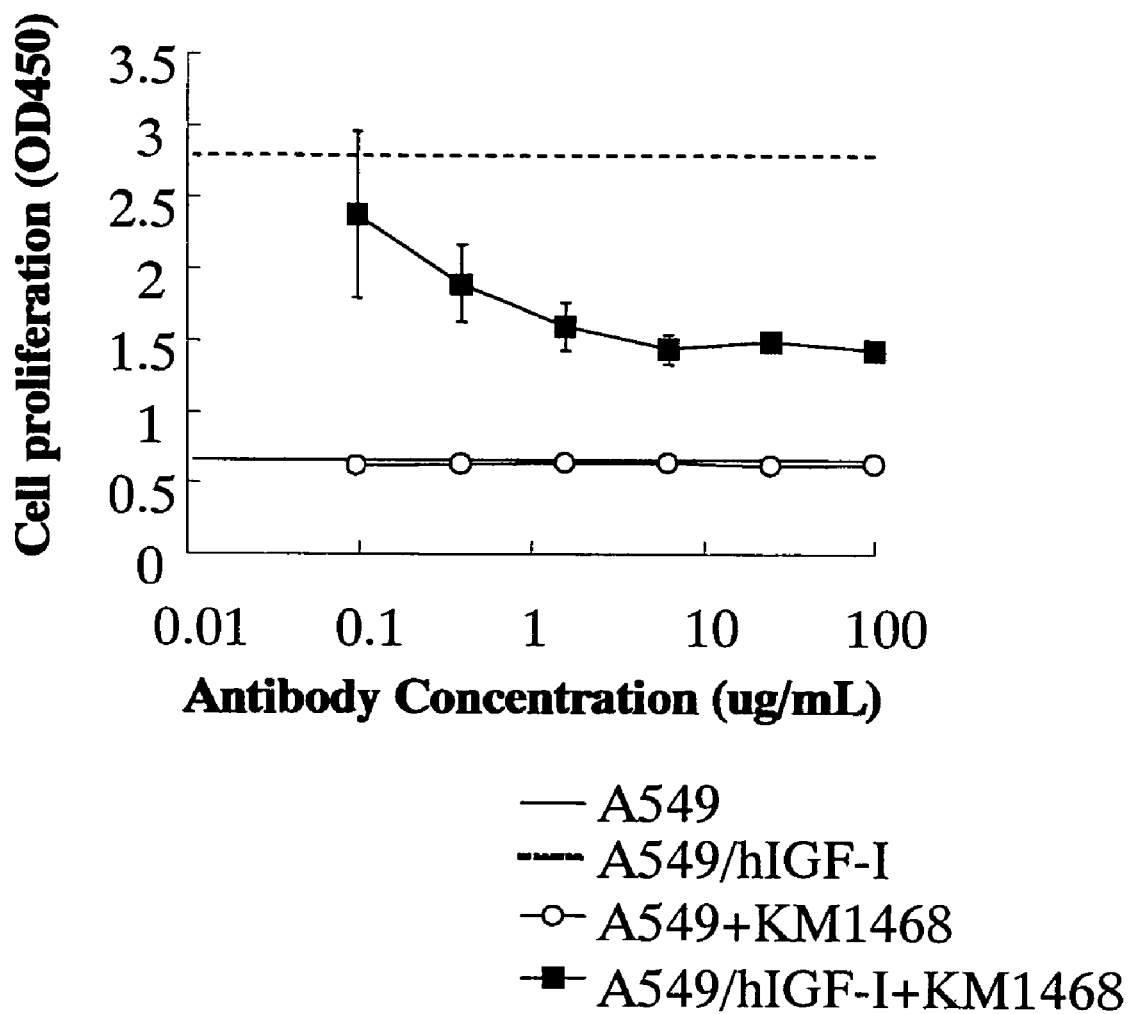
FIG. 13 shows cell proliferation inhibitory effect of KM1468 upon hIGF-I expressing cells. Dotted line shows the growth of A549/hIGF-I cell in the absence of anti-hIGF rat monoclonal KM1468, and solid line shows the proliferation of A549 cell in the absence of anti-hIGF rat monoclonal KM1468. The symbol ■ shows the proliferation of A549/hIGF-I cell in the presence of anti-hIGF antibody KM1468; and ○ shows the proliferation of A549 cell in the presence of anti-hIGF antibody KM1468, respectively.
Figure 14:
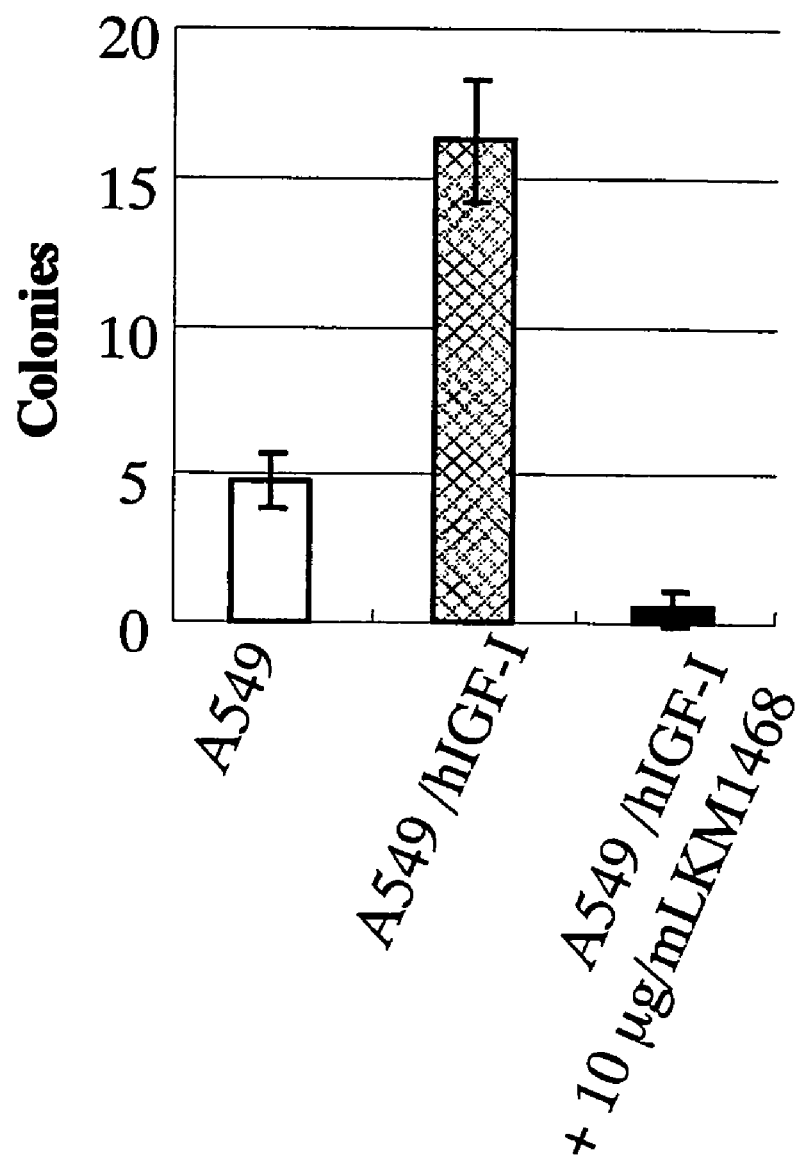
FIG. 14 shows the anchorage independent proliferation inhibitory effect of KM1468. In the drawing, Blank column shows the number of formed colonies of A549 cell, net column shows the number of formed A549/hIGF-I cells, and black-finished column shows the number of formed A549/hIGF-I cells in the presence of anti-hIGF antibody KM1468, respectively.
Figure 15:
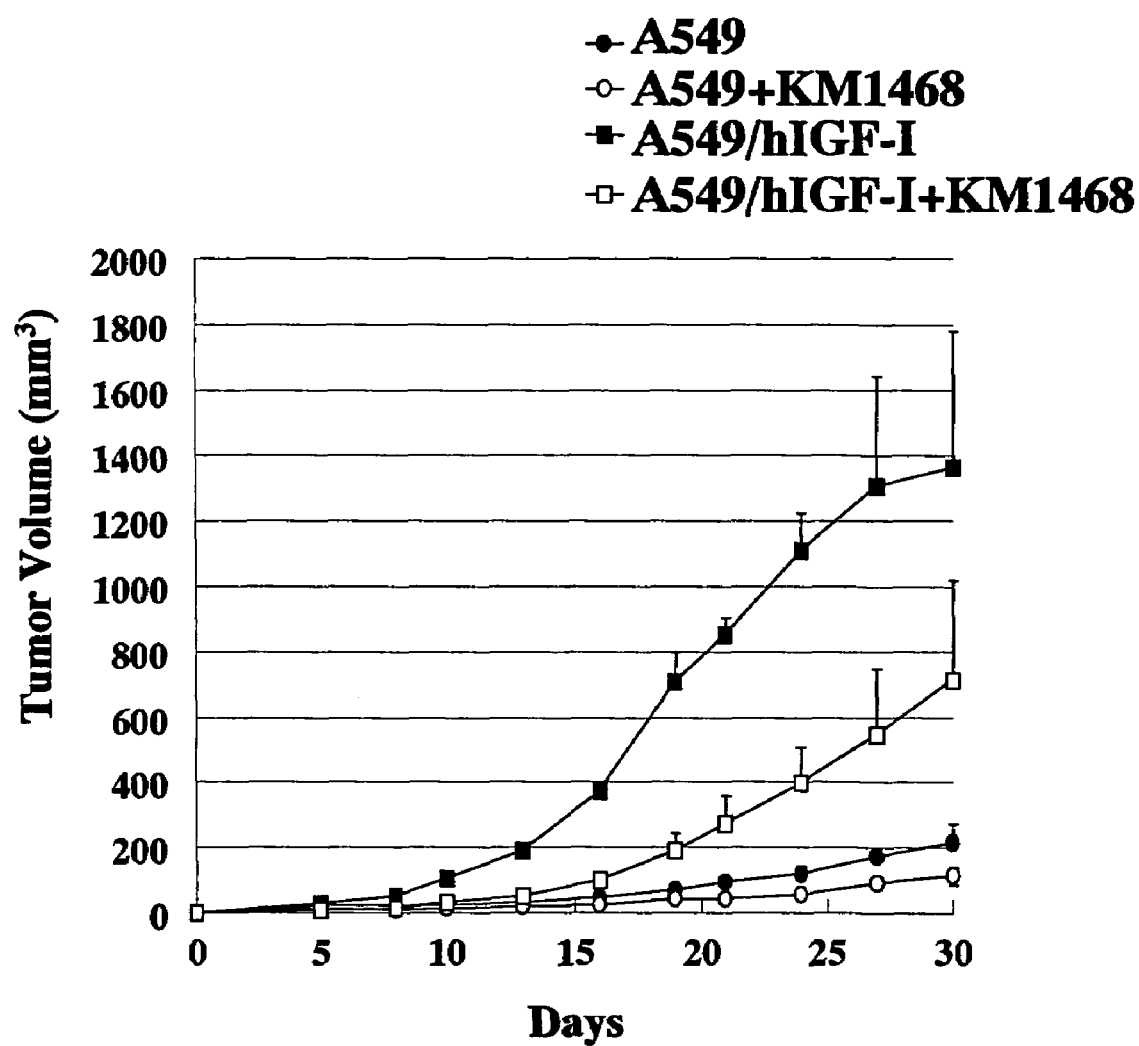
FIG. 15 shows the anti-tumor effect of anti-hIGF rat monoclonal KM1468. The abscissa shows the number of elapsed days after tumor grafting, and the ordinate shows tumor volume. Among the mice grafted with A549 cell, ● shows effect in the absence of anti-hIGF antibody KM1468, and ○ shows effect in the presence of anti-hIGF antibody KM1468, respectively. Among the mice grafted with A549/hIGF-I cell, ■ shows effect in the absence of anti-hIGF antibody KM1468, and ■ shows effect in the presence of anti-hIGF antibody KM1468, respectively.
Figure 16:
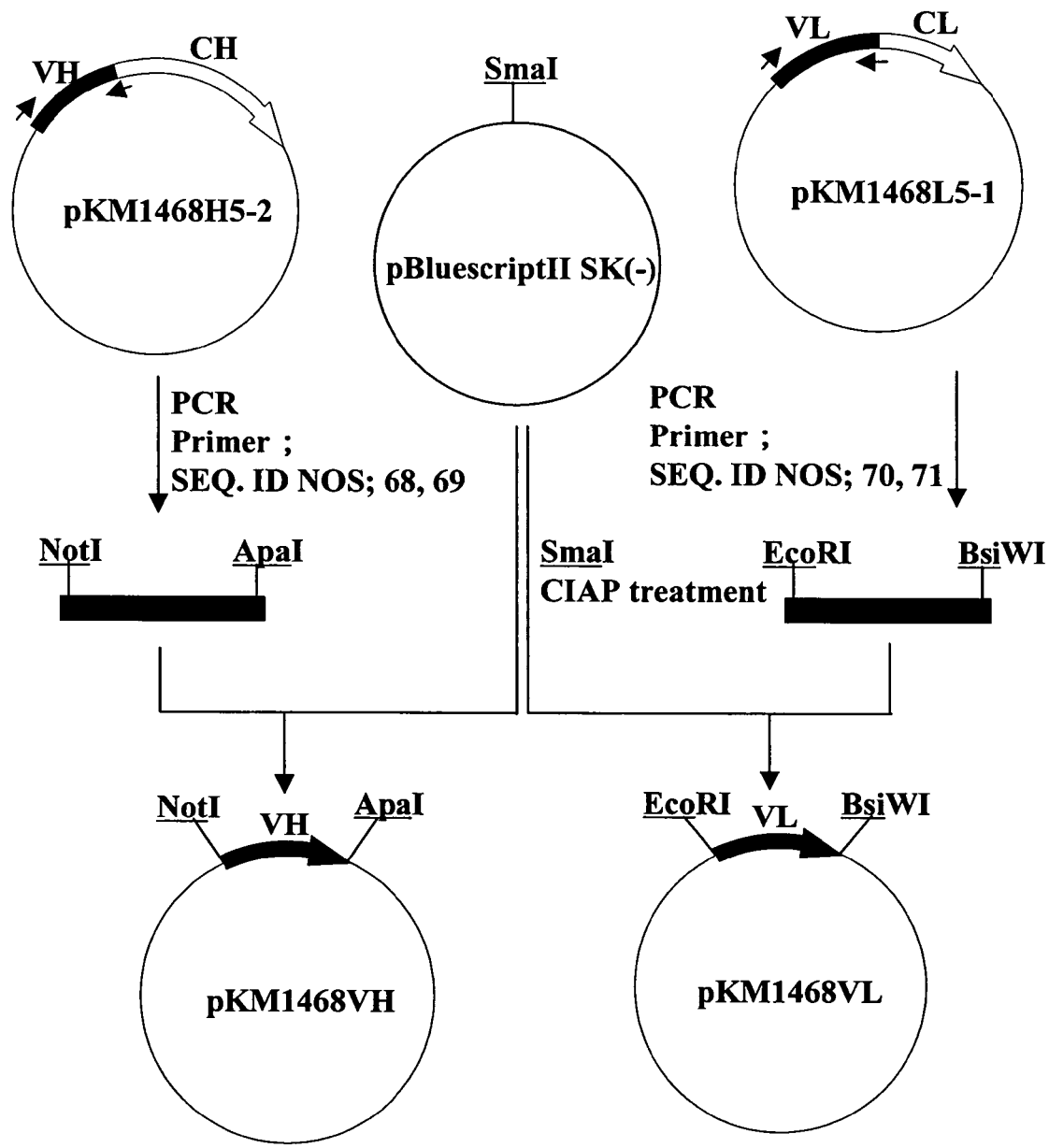
FIG. 16 shows the construction steps of plasmids pKM1468VH and pKM1468VL.
Figure 17:
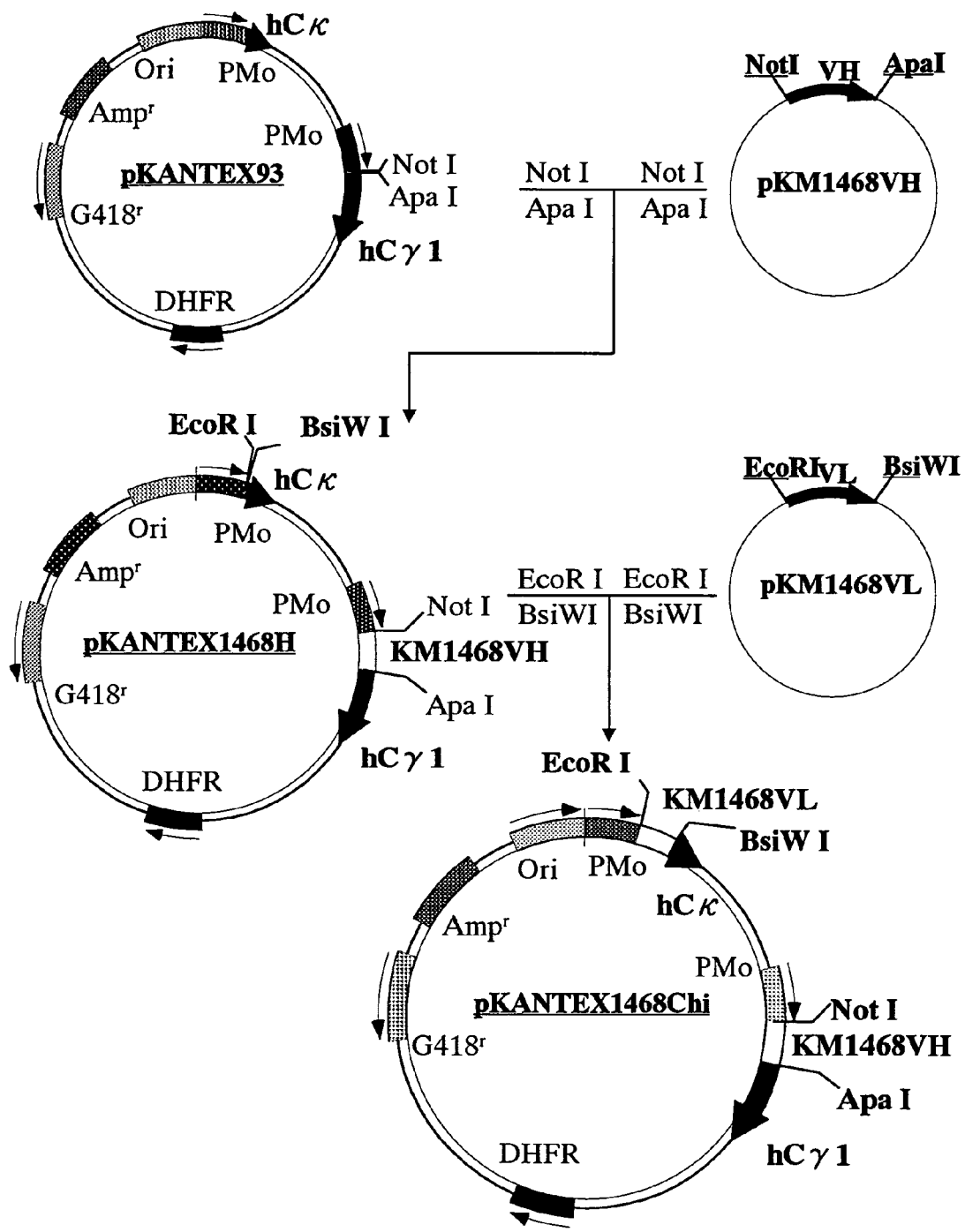
FIG. 17 shows the construction steps of a plasmid pKANTEX1468Chi.
Figure 18:
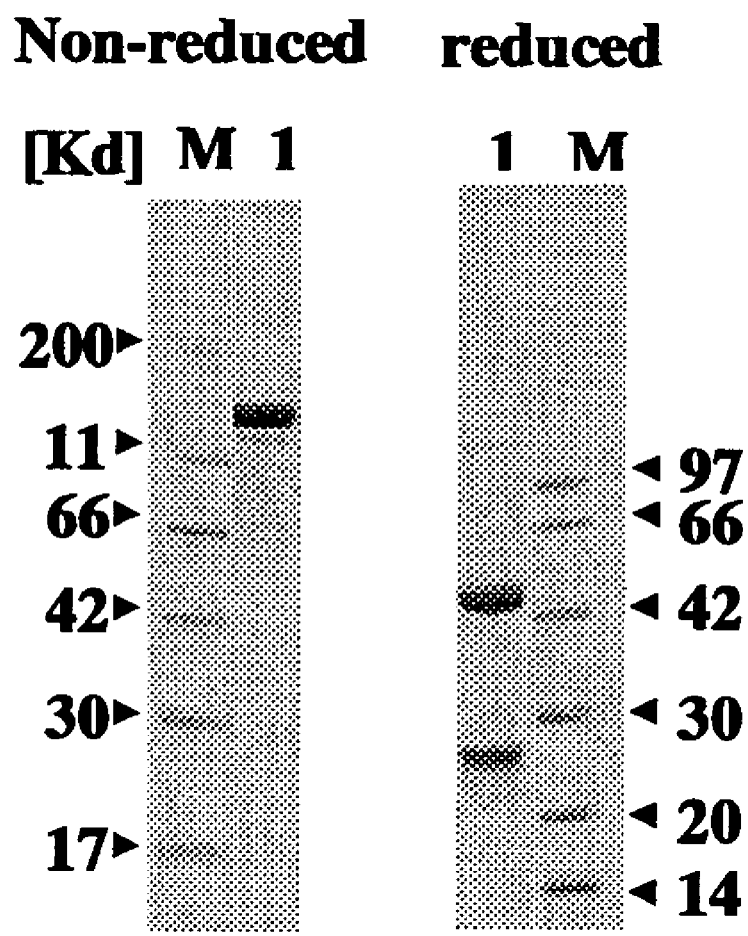
FIG. 18 shows SDS-PAGE (using a 4 to 15% gradient gel) electrophoresis pattern of purified anti-hIGF chimeric antibody KM3002. The left side is the electrophoresis pattern under non-reducing condition, and the right side is the electrophoresis pattern under reducing condition. Lane M shows high molecular weight markers under non-reducing condition or low molecular weight markers under reducing condition, and lane 1 shows electrophoresis pattern of KM3002, respectively.
Figure 19:
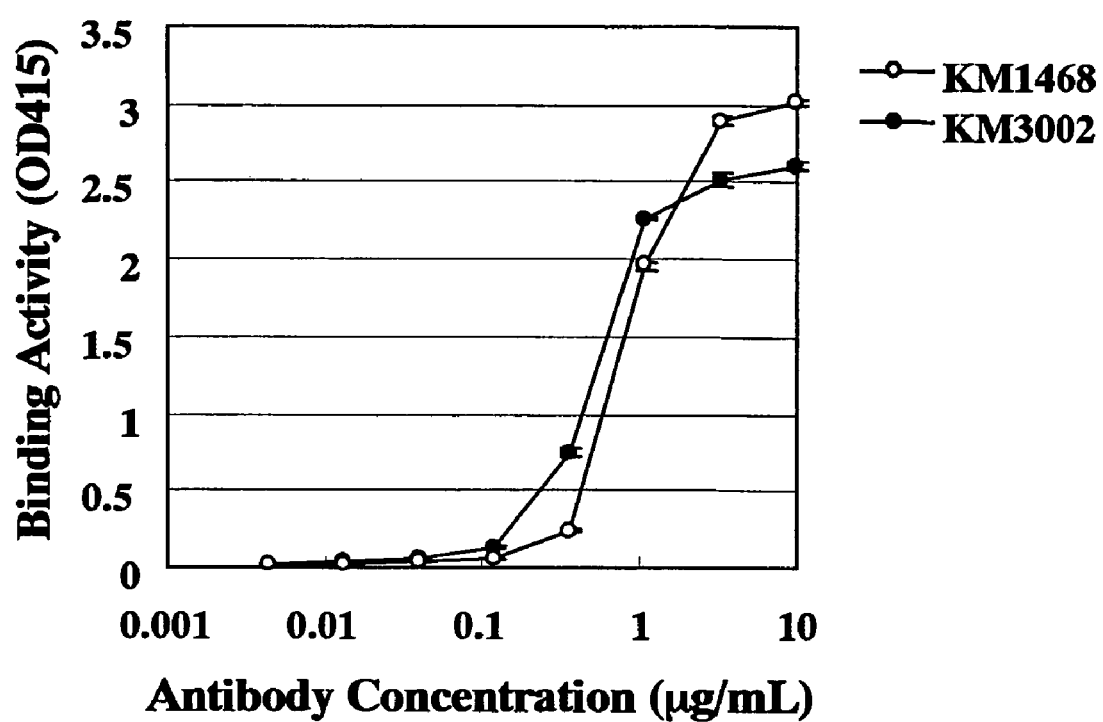
FIG. 19 shows reaction of anti-hIGF rat antibody KM1468 and anti-hIGF chimeric antibody KM3002 upon hIGF-I. The abscissa shows antibody concentration (μg/ml), and the ordinate shows binding activity (OD415), respectively. ○ shows reactivity of KM1468, and ● shows reactivity of KM3002, respectively.

SEQ ID NO:13—Description of artificial sequence, synthetic DNA
SEQ ID NO:16—Description of artificial sequence, synthetic DNA
SEQ ID NO:17—Description of artificial sequence, synthetic DNA
SEQ ID NO:18—Description of artificial sequence, synthetic DNA
SEQ ID NO:19—Description of artificial sequence, synthetic DNA
SEQ ID NO:20—Description of artificial sequence, synthetic DNA
SEQ ID NO:21—Description of artificial sequence, synthetic DNA
SEQ ID NO:22—Description of artificial sequence, synthetic DNA
SEQ ID NO:23—Description of artificial sequence, synthetic DNA
SEQ ID NO:24—Description of artificial sequence, synthetic DNA
SEQ ID NO:25—Description of artificial sequence, synthetic DNA
SEQ ID NO:30—Description of artificial sequence, synthetic DNA
SEQ ID NO:31—Description of artificial sequence, synthetic DNA
SEQ ID NO:32—Description of artificial sequence, synthetic DNA
SEQ ID NO:33—Description of artificial sequence, synthetic DNA
SEQ ID NO:34—Description of artificial sequence, synthetic DNA
SEQ ID NO:35—Description of artificial sequence, synthetic DNA
SEQ ID NO:36—Description of artificial sequence, synthetic DNA
SEQ ID NO:37—Description of artificial sequence, synthetic DNA
SEQ ID NO:38—Description of artificial sequence, synthetic DNA
SEQ ID NO:39—Description of artificial sequence, synthetic DNA
SEQ ID NO:40—Description of artificial sequence, synthetic DNA
SEQ ID NO:41—Description of artificial sequence, synthetic DNA
SEQ ID NO:42—Description of artificial sequence, synthetic DNA
SEQ ID NO:43—Description of artificial sequence, synthetic DNA
SEQ ID NO:44—Description of artificial sequence, synthetic DNA
SEQ ID NO:45—Description of artificial sequence, synthetic DNA
SEQ ID NO:46—Description of artificial sequence, synthetic DNA
SEQ ID NO:47—Description of artificial sequence, synthetic DNA
SEQ ID NO:48—Description of artificial sequence, synthetic DNA
SEQ ID NO:49—Description of artificial sequence, synthetic DNA
SEQ ID NO:50—Description of artificial sequence, synthetic DNA
SEQ ID NO:51—Description of artificial sequence, synthetic DNA
SEQ ID NO:52—Description of artificial sequence, synthetic DNA
SEQ ID NO:53—Description of artificial sequence, synthetic DNA SEQ ID NO:66—Description of artificial sequence, synthetic DNA
SEQ ID NO:67—Description of artificial sequence, synthetic DNA
SEQ ID NO:68—Description of artificial sequence, synthetic DNA
SEQ ID NO:69—Description of artificial sequence, synthetic DNA
SEQ ID NO:70—Description of artificial sequence, synthetic DNA
SEQ ID NO:71—Description of artificial sequence, synthetic DNA

The invention claimed is:

1. A recombinant antibody or an antibody fragment thereof, which specifically binds to human insulin-like growth factor-I (IGF-I) and human insulin-like growth factor-II (IGF-II) to inhibit control of proliferation, differentiation or apoptosis of epithelial cells of both human IGF-I and human IGF-II, wherein the VH of the recombinant antibody or the antibody fragment thereof comprises an amino acid sequence of SEQ ID NO:26 and the VL comprises an amino acid sequence of SEQ ID NO:27, 28 or 29.

2. The recombinant antibody or the antibody fragment thereof according to claim 1, wherein the VL comprises an amino acid sequence of SEQ ID NO:27.

3. The recombinant antibody or the antibody fragment thereof according to claim 1, wherein the VL comprises an amino acid sequence of SEQ ID NO:28.

4. The recombinant antibody or the antibody fragment thereof according to claim 1, wherein the VL comprises an amino acid sequence of SEQ ID NO:29.

5. The recombinant antibody or the antibody fragment thereof according to any one of claims 1 or 2-4, wherein the recombinant antibody is a human CDR-grafted antibody.

6. The recombinant antibody or the antibody fragment thereof according to any one of claims 1 or 2-4, wherein the antibody fragment is an antibody fragment selected from the group consisting of Fab, Fab', F(ab')$_2$, single-stranded antibody (scFv), dimerized variable region (diabody), disulfide-stabilized variable region (dsFv), and CDR-containing peptide.

7. The recombinant antibody or the antibody fragment thereof according to claim 5, wherein the antibody fragment is an antibody fragment selected from the group consisting of Fab, Fab', F(ab')$_2$, single-stranded antibody (scFv), dimerized variable region (diabody), disulfide-stabilized variable region (dsFv), and CDR-containing peptide.

8. A process for producing a recombinant antibody or the antibody fragment thereof according to any one of claims 1, 2-4, which comprises a step of culturing a transformant obtained by introducing into a host cell an expression vector carrying DNA encoding said recombinant antibody or antibody fragment thereof in a medium to produce the recombinant antibody or the antibody fragment thereof in a culture, and isolating and purifying the recombinant antibody or the antibody fragment thereof from the culture.

9. A process for producing a recombinant antibody or the antibody fragment thereof according to claim 5, which comprises a step of culturing a transformant obtained by introducing into a host cell an expression vector carrying DNA encoding said recombinant antibody or antibody fragment thereof in a medium to produce the recombinant antibody or the antibody fragment thereof in a culture, and isolating and purifying the recombinant antibody or the antibody fragment thereof from the culture.

10. A process for producing a recombinant antibody or the antibody fragment thereof according to claim 6, which comprises a step of culturing a transformant obtained by introducing into a host cell an expression vector carrying DNA encoding said recombinant antibody or antibody fragment thereof in a medium to produce the recombinant antibody or the antibody fragment thereof in a culture, and isolating and purifying the recombinant antibody or the antibody fragment thereof from the culture.

11. A process for producing a recombinant antibody or the antibody fragment thereof according to claim 7, which comprises a step of culturing a transformant obtained by introducing into a host cell an expression vector carrying DNA encoding said recombinant antibody or antibody fragment thereof in a medium to produce the recombinant antibody or the antibody fragment thereof in a culture, and isolating and purifying the recombinant antibody or the antibody fragment thereof from the culture.

* * * * *